(12) United States Patent
Breuning et al.

(10) Patent No.: US 9,593,087 B2
(45) Date of Patent: Mar. 14, 2017

(54) MATERIALS FOR ORGANIC ELECTROLUMINESCENT DEVICES

(75) Inventors: Esther Breuning, Ober-Ramstadt (DE); Heinrich Becker, Ober-Ramstadt (DE); Junyou Pan, Frankfurt am Main (DE); Herwig Buchholz, Frankfurt am Main (DE); Teresa Mujica-Fernaud, Darmstadt (DE); Irina Martynova, Griesheim (DE)

(73) Assignee: Merck Patent GmbH (DE)

( * ) Notice: Subject to any disclaimer, the term of this patent is extended or adjusted under 35 U.S.C. 154(b) by 339 days.

(21) Appl. No.: 13/805,943

(22) PCT Filed: May 30, 2011

(86) PCT No.: PCT/EP2011/002669
§ 371 (c)(1),
(2), (4) Date: Dec. 20, 2012

(87) PCT Pub. No.: WO2011/160758
PCT Pub. Date: Dec. 29, 2011

(65) Prior Publication Data
US 2013/0099171 A1 Apr. 25, 2013

(30) Foreign Application Priority Data
Jun. 24, 2010 (DE) .................. 10 2010 024 897

(51) Int. Cl.
| | | |
|---|---|---|
| *H01L 51/50* | (2006.01) | |
| *C07D 251/22* | (2006.01) | |
| *C07D 251/24* | (2006.01) | |
| *C07D 251/42* | (2006.01) | |
| *C07D 403/12* | (2006.01) | |
| *C07D 409/12* | (2006.01) | |
| *C07D 409/14* | (2006.01) | |
| *C07D 487/04* | (2006.01) | |
| *C07D 487/16* | (2006.01) | |
| *C09K 11/06* | (2006.01) | |
| *H01L 51/00* | (2006.01) | |
| *H05B 33/10* | (2006.01) | |
| *H05B 33/14* | (2006.01) | |
| *C07D 403/14* | (2006.01) | |
| *C07F 7/10* | (2006.01) | |

(52) U.S. Cl.
CPC ......... *C07D 251/22* (2013.01); *C07D 251/24* (2013.01); *C07D 251/42* (2013.01); *C07D 403/12* (2013.01); *C07D 403/14* (2013.01); *C07D 409/12* (2013.01); *C07D 409/14* (2013.01); *C07D 487/04* (2013.01); *C07D 487/16* (2013.01); *C07F 7/10* (2013.01); *C09K 11/06* (2013.01); *H01L 51/0067* (2013.01); *H01L 51/5072* (2013.01); *H01L 51/5088* (2013.01); *H05B 33/10* (2013.01); *H05B 33/14* (2013.01); *C09K 2211/1007* (2013.01); *C09K 2211/1011* (2013.01); *C09K 2211/1014* (2013.01); *C09K 2211/1044* (2013.01); *C09K 2211/1059* (2013.01); *Y02E 10/549* (2013.01)

(58) Field of Classification Search
None
See application file for complete search history.

(56) References Cited

U.S. PATENT DOCUMENTS

| | | | |
|---|---|---|---|
| 4,116,700 A | 9/1978 | Himmelmann | |
| 2007/0007882 A1* | 1/2007 | Fukuoka | H01L 51/0051 313/503 |
| 2010/0072888 A1 | 3/2010 | Kim et al. | |
| 2010/0108997 A1* | 5/2010 | Kim | C07C 211/54 257/40 |

FOREIGN PATENT DOCUMENTS

| | | | | |
|---|---|---|---|---|
| DE | 2616376 A1 | | 10/1977 | |
| EP | 2175005 A1 | | 4/2010 | |
| JP | 47006620 | * | 2/1972 | .......... C07D 333/76 |
| JP | 2002-175883 A | | 6/2002 | |
| JP | 2004-206893 | * | 7/2004 | ............. C09K 11/06 |
| JP | 2010-065033 A | | 3/2010 | |
| WO | WO-2010/050779 A1 | | 5/2010 | |

OTHER PUBLICATIONS

Funushima et al., Derivatives of Ditriazinylamine; 1971, Bulletin of the Chemical Society of Japan, 44(3); STN Abstract.*
Prashad, Mahavir, et al., "A New Reaction of N-Aryl-2-Pyrimidinamines with Triphosgene", Tetrahedron Letters, vol. 48, (2007), pp. 2087-2089.
Prashad, M., et al., "A New Reaction of N-Aryl-2-Pyrimidinamines with Triphosgene", XP55006267, (2007).
Nohara, N., et al., "Derivatives of Ditraizinylamine and Tritriazinylamine", Journal of Heterocyclic Chemistry, Bd. 7, No. 3, (1970), pp. 519-525.
Pang, Jun, et al., "Syntheses, Structures, and Electroluminescence of New Blue Luminescent Star-Shaped Compounds Based on 1,3,5-Triazine and 1,3,5-Trisubstituted Benzene", J. Mater. Chem., vol. 12, (2002), pp. 206-212.
Wong, Elizabeth, et al., "Cu(I) and Ag(I) Complexes of 7-Azaindolyl and 2,2'-Dipyridylamino Substituted 1,3,5-Triazine and Benzene: the Central Core Impact on Structure, Solution Dynamics and Fluorescence of the Complexes", Dalton Transactions,, No. 1, (2009), pp. 1776-1785.
International Search Report for PCT/EP2011/002669 mailed Sep. 23, 2011.
Norman et al., "Novel Vanilloid Receptor-1 Antagonists: 1. Conformationally Restricted Analogues of trans-Cinnamidest†", J. Med. Chem., vol. 50, pp. 3497-3514 (2007).
Authors et al., Disclosed Anonymously, "2-[Bis(6-chloro-2-methlpyrimidin-4-yl)-amino]-thiazole-5-carboxylic acid (2-chloro-6-methyl-phenyl)-amide", IP.com, Electronic Publication No. IPCOM000176077D (Nov. 4, 2008).

\* cited by examiner

*Primary Examiner* — Gregory Clark
(74) *Attorney, Agent, or Firm* — Drinker Biddle & Reath LLP

(57) ABSTRACT

The present invention relates to compounds of the formula (1) which are suitable for use in electronic devices, in particular organic electroluminescent devices, and to electronic devices which comprise these compounds.

20 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2011/002669, filed May 30, 2011, which claims benefit of German application 10 2010 024 897.5, filed Jun. 24, 2010 which are both incorporated by reference.

The present invention relates to materials for use in electronic devices, in particular in organic electroluminescent devices, and to electronic devices comprising these materials.

The structure of organic electroluminescent devices (OLEDs, in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, there is still a need for improvement in the case of OLEDs, in particular also in the case of OLEDs which exhibit triplet emission (phosphorescence), for example with respect to efficiency, operating voltage and in particular lifetime. This applies, in particular, to OLEDs which emit in the relatively short-wave region, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in these materials for fluorescent OLEDs.

In accordance with the prior art, ketones (for example in accordance with WO 2004/093207 or WO 2010/006680) or phosphine oxides (for example in accordance with WO 2005/003253), inter alia, are used as matrix materials for phosphorescent emitters. Furthermore, triazine derivatives are used as matrix materials for phosphorescent emitters (for example in accordance with WO 2007/063754, WO 2008/056746 or WO 2010/015306). However, there is still a need for improvement on use of these matrix materials just as in the case of other matrix materials, in particular with respect to the efficiency and lifetime of the device.

The object of the present invention is the provision of compounds which are suitable for use in a fluorescent or phosphorescent OLED, in particular a phosphorescent OLED, for example as matrix material or as electron-transport or hole-blocking material. In particular, the object of the present invention is to provide matrix materials which are also suitable for green- and blue-phosphorescent OLEDs. It is furthermore the object of the present invention to provide improved electron-transport materials.

Surprisingly, it has been found that certain compounds described below in greater detail achieve this object and result in significant improvements in the organic electroluminescent device, in particular with respect to the life-time, efficiency and operating voltage. This applies to red-, green- and blue-phosphorescent and -fluorescent electroluminescent devices, especially on use of the compounds according to the invention as matrix material or as electron-transport material. The present invention therefore relates to these materials and to organic electroluminescent devices which comprise compounds of this type.

The present invention therefore relates to a compound of the following formula (1),

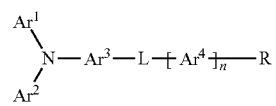

formula (1)

where the following applies to the symbols and indices used:

Ar$^1$, Ar$^2$ is, identically or differently on each occurrence, a group of the following formula (2),

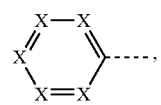

formula (2)

where the dashed bond indicates the bond to the nitrogen;

Ar$^3$, Ar$^4$ is on each occurrence, identically or differently, an aromatic or heteroaromatic ring system having 5 to 30 aromatic ring atoms, which may be substituted by one or more radicals R; with the proviso that Ar$^3$ and Ar$^4$ contain no amino groups and no carbazole groups bonded via N;

X is on each occurrence, identically or differently, CR$^1$ or N, with the proviso that at least two groups X and a maximum of three groups X in each group of the formula (2) stand for N;

L is a single bond or a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which may be substituted by in each case one or more radicals R, where one or more CH$_2$ groups, which are preferably not adjacent, may be replaced by Si(R)$_2$, Ge(R)$_2$, Sn(R)$_2$, C=O, C=S, C=Se, C=NR, P(=O)R, S=O, SO$_2$, —O—, —S— or —CONR— and where one or more H atoms may be replaced by D, F, Cl, Br, I, CN or NO$_2$, or a divalent aromatic or heteroaromatic ring system having 5 to 30 aromatic ring atoms, which may be substituted by one or more radicals R and which contains no amino groups and no carbazole groups bonded via N, or Si(R)$_2$, Ge(R)$_2$, O, S, C(=O), S(=O), SO$_2$, PR, P(=O)(R), P(=S)(R) or a combination of two, three, four or five of these systems;

R, R$^1$ is selected on each occurrence, identically or differently, from the group consisting of H, D, F, Cl, Br, I, CN, NO$_2$, C(=O)Ar, C(=O)R$^2$, P(=O)(AR)$_2$, B(R$^2$)$_2$, B(OR$^2$)$_2$, Si(R$^2$)$_3$, a straight-chain alkyl, alkoxy or thio-alkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R$^2$, where one or more non-adjacent CH$_2$ groups may be replaced by R$^2$C=CR$^2$, C≡C, Si(R$^2$)$_2$, Ge(R$^2$)$_2$, Sn(R$^2$)$_2$, C=O, C=S, C=Se, C=NR$^2$, P(=O)(R$^2$), SO, SO$_2$, NR$^2$, O, S or CONR$^2$ and where one or more H atoms may be replaced by D, F, Cl, Br, I, CN or NO$_2$, an aromatic or heteroaromatic ring system having 5 to 60 aromatic ring atoms, which may in each case be substituted by one or more radicals R² and which contains no amino groups and no carbazole groups bonded via N, an aryloxy or heteroaryloxy group having 5 to 60 aromatic ring atoms, which may be substituted by one or more radicals R², or an aralkyl or heteroaralkyl group having 5 to 60 aromatic ring atoms, which may in each case be substituted by one or more radicals R², where two or more adjacent substituents R may optionally form a mono- or polycyclic, aliphatic, aromatic or heteroaromatic ring system, which may be substituted by one or more radicals R²; with the proviso that R¹ contains no condensed aryl groups;

R² is selected on each occurrence, identically or differently, from the group consisting of H, D, F, Cl, Br, I, CN, NO₂, C(=O)Ar, C(=O)R³, P(=O)(Ar)₂, B(R³)₂, B(OR³)₂, Si(R³)₃, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals R³, where one or more non-adjacent CH₂ groups may be replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms may be replaced by D, F, Cl, Br, I, CN or NO₂, an aromatic or heteroaromatic ring system having 5 to 60 aromatic ring atoms, which may in each case be substituted by one or more radicals R³ and which contains no amino groups and no carbazole groups bonded via N, an aryloxy or heteroaryloxy group having 5 to 60 aromatic ring atoms, which may be substituted by one or more radicals R³, or an aralkyl or heteroaralkyl group having 5 to 60 aromatic ring atoms, which may be substituted by one or more radicals R³, where two or more adjacent substituents R² may optionally form a mono- or polycyclic, aliphatic, aromatic or heteroaromatic ring system, which may be substituted by one or more radicals R³;

Ar is on each occurrence, identically or differently, an aromatic or heteroaromatic ring system having 5-30 aromatic ring atoms, which may be substituted by one or more non-aromatic radicals R³; two radicals Ar which are bonded to the same P atom may also be bridged to one another here by a single bond or a bridge selected from N(R³), C(R³)₂, O or S;

R³ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents R³ may form a mono- or polycyclic, aliphatic, aromatic or heteroaromatic ring system with one another;

n is 0 or 1;

characterised in that at least one radical R¹ stands for an aromatic or heteroaromatic ring system and/or in that Ar³ represents an aromatic or heteroaromatic ring system having at least two aryl or heteroaryl groups and/or in that n=1 and thus one group Ar⁴ is present;

the following compounds are excluded from the invention:

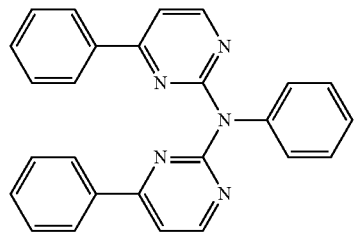

-continued

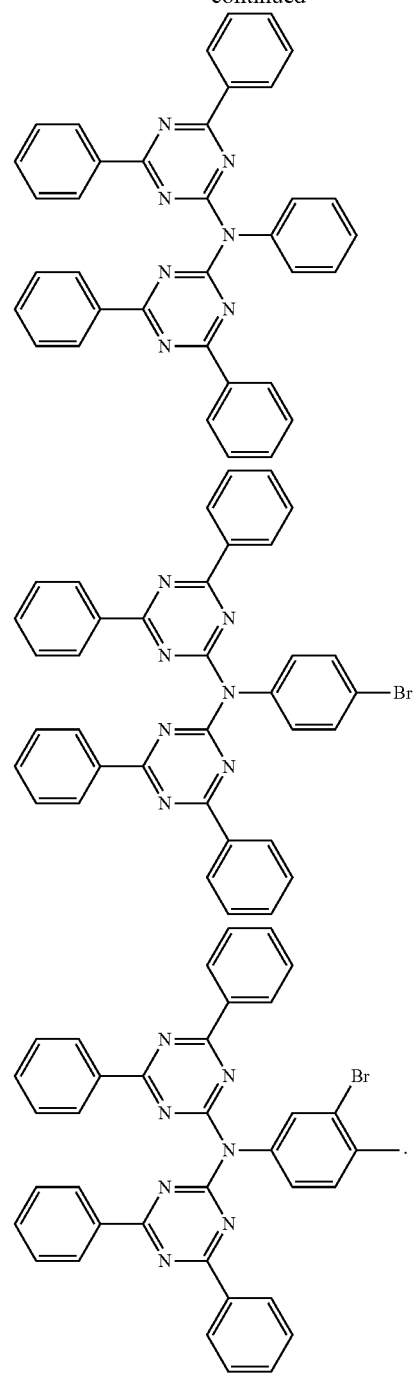

An aryl group in the sense of this invention contains 6 to 60 C atoms; a heteroaryl group in the sense of this invention contains 1 to 59 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl or bipyridine, are, by contrast, not referred to as an aryl or heteroaryl group, but instead as an aromatic or heteroaromatic ring system.

An aromatic ring system in the sense of this invention contains 6 to 60 C atoms in the ring system. A heteroaromatic ring system in the sense of this invention contains 1 to 59 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is also intended to be taken to mean, in particular, a system in which, in addition, a plurality of aryl and/or heteroaryl groups are linked to one another directly or via a carbon atom. Thus, for example, systems such as biphenyl, terphenyl, fluorene, indenofluorene, 9,9'-spirobifluorene, 9,9-di-arylfluorene, etc., in particular, are also intended to be taken to be aromatic ring systems in the sense of this invention. The aromatic or heteroaramatic ring system here contains no amino groups, in accordance with the definition. Triarylamino groups or corresponding heteroaromatic groups are thus not encompassed by the definition of an aromatic or heteroaromatic ring system.

An aromatic or heteroaromatic ring system which contains no condensed aryl groups is, in the sense of the present invention, taken to mean an aromatic ring system which either contains only non-condensed aryl or heteroaryl groups, such as, for example, phenyl or pyridine, or which, if it contains condensed aryl groups, then only contains condensed aryl groups or partially saturated rings. By contrast, groups in which two or more benzene rings are condensed directly onto one another via a common edge are excluded. Thus, for example, naphthalene, anthracene, phenanthrene, pyrene, perylene, etc. are excluded from the definition of $R^1$, since benzene rings in these groups are condensed directly onto one another; by contrast, quinoline, fluorene, spirobifluorene, indenofluorene, carbazole, indenocarbazole or indolocarbazole, for example, are encompassed by the definition of $R^1$, since no benzene rings in these groups are condensed directly onto one another, but instead only saturated (aliphatic) five-membered rings or heteroaryl groups, i.e. they are condensed heteroaryl groups and not condensed aryl groups.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl and octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals and which may be linked via any desired positions on the aromatic or heteroaromatic ring system, is taken to mean, in particular, groups derived from benzene, naphthalene, anthracene, benzanthracene, phenanthrene, benzphenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

Preferred embodiments of the groups of the formula (2) are selected from the group consisting of 1,3,5-triazine, 1,2,4-triazine, pyrazine, pyrimidine and pyridazine, where these groups may each be substituted by one or more radicals $R^1$. The radical $R^1$ here is as defined above and contains, in accordance with the definition, no condensed aryl groups.

Preferred embodiments of the groups of the formula (2) are therefore selected, identically or differently on each occurrence, from the groups of the following formulae (3) to (12),

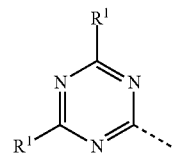

formula (3)

-continued formula (4)
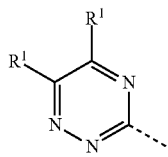

formula (5)
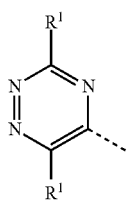

formula (6)
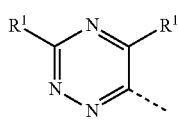

formula (7)
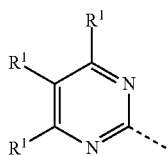

formula (8)
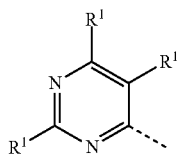

formula (9)
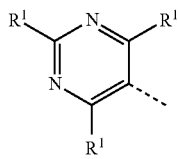

formula (10)
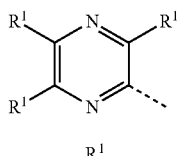

formula (11)
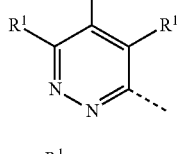

formula (12)
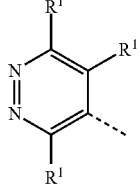

where the symbols used have the meanings given above and the dashed bond indicates the position of the bond from the group to the nitrogen.

The two groups of the above-mentioned formulae (3) to (12) which are bonded to the nitrogen may be combined with one another as desired here. The groups of the formulae (3), (7), (8) and (9) and combinations of these groups are particularly preferred.

Preferred groups —NAr$^1$Ar$^2$ in compounds of the formula (1) are the groups of the following formulae (13) to (17):

formula (13)

formula (14)

formula (15)

formula (16)

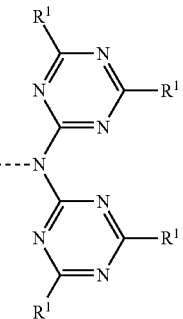

formula (17)

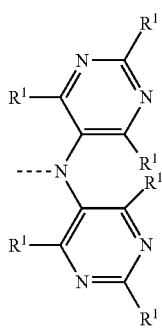

where the symbols used have the meanings given above and the dashed bond indicates the bond from this group to Ar³.

In a further preferred embodiment of the invention, L is a single bond, a divalent straight-chain alkylene or alkylidene group having 1 to 10 C atoms, in particular having 1 to 5 C atoms, or a branched or cyclic alkylene or alkylidene group having 3 to 10 C atoms, in particular having 3 to 6 C atoms, which may be substituted by in each case one or more radicals R, where one or more CH₂ groups, which are preferably not bonded directly to N and are preferably not adjacent, may be replaced by Si(R)₂, C═O, P(═O)R, S═O, SO₂, —O—, —S— or —CONR— and where one or more H atoms may be replaced by D or F, or a divalent aromatic or heteroaromatic ring system having 5 to 24 aromatic ring atoms, which may also be substituted by one or more radicals R, or Si(R)₂, C(═O), S(═O), SO₂, P(═O)R, O or S. L here preferably contains no aryl groups having more than two aromatic six-membered rings condensed directly onto one another if L is employed as matrix material for a phosphorescent emitter. L then particularly preferably also contains no aryl groups having two aromatic six-membered rings condensed directly onto one another.

In a particularly preferred embodiment of the invention, L is a single bond, a divalent aromatic or heteroaromatic ring system having 6 to 24 aromatic ring atoms, which may be substituted by one or more radicals R, or Si(R)₂ or C(═O). L here preferably contains only non-condensed aryl groups if the compound of the formula (1) is employed as matrix material for phosphorescent emitters. If the compound of the formula (1) is employed as electron-transport material, the use of condensed aryl groups, for example anthracene, may also be preferred.

If L stands for an aromatic or heteroaromatic ring system which contains no condensed aryl groups, L is then preferably selected from structures of the following formulae (18) to (112), formula (18)

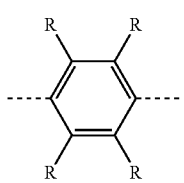

formula (19)

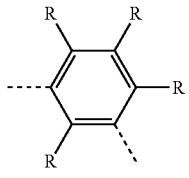

formula (20)

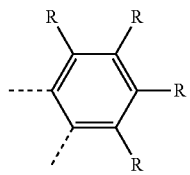

formula (21)

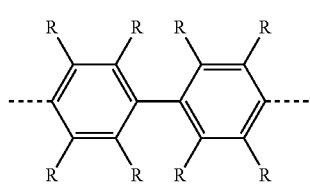

formula (22)

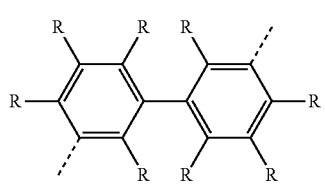

formula (23)

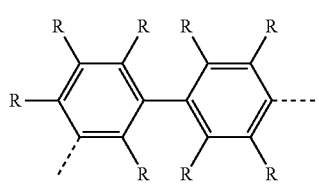

formula (24)

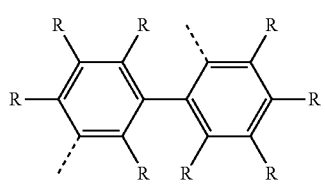

formula (25)

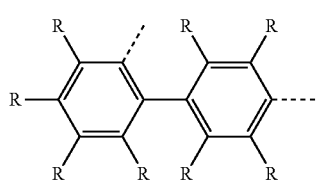

formula (26)

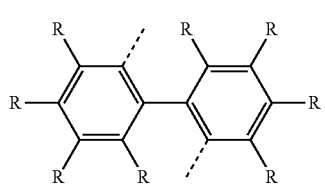

formula (27)

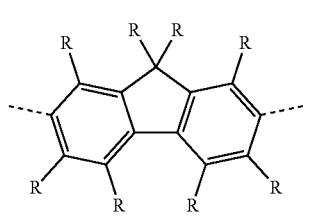

formula (28)
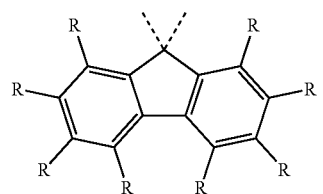
formula (29)
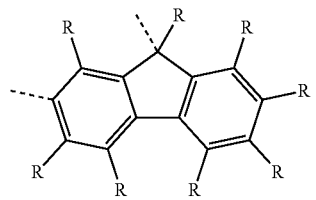
formula (30)
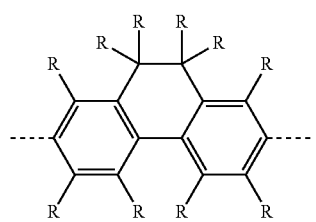
formula (31)
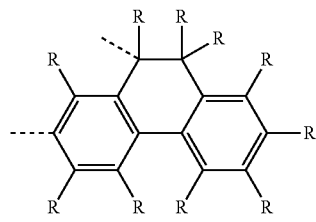
formula (32)
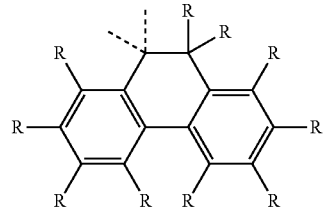
formula (33)
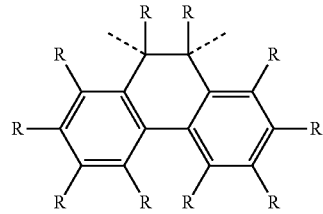
formula (34)
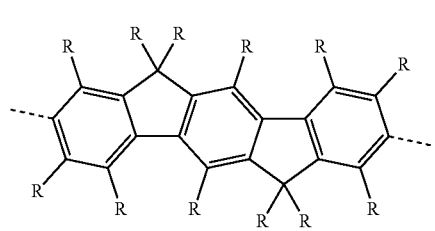
formula (35)
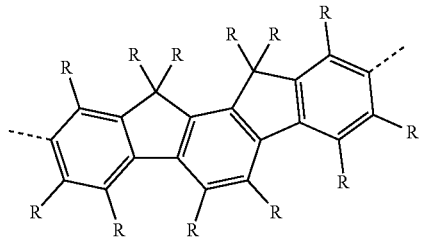
formula (36)
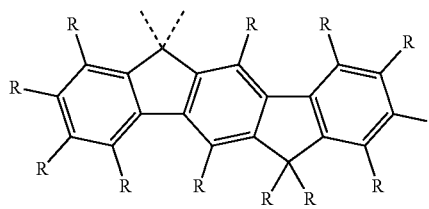
formula (37)
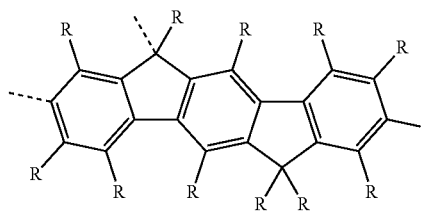
formula (38)
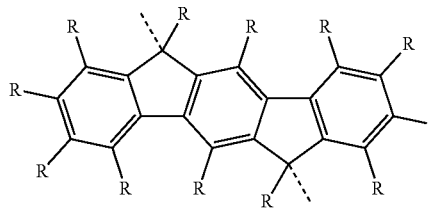
formula (39)
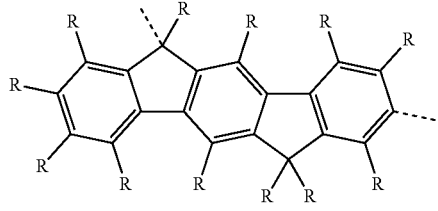
formula (40)
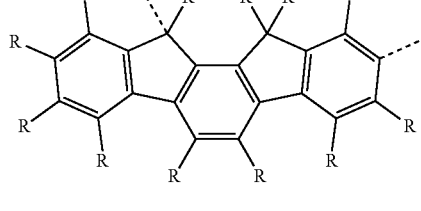
formula (41)
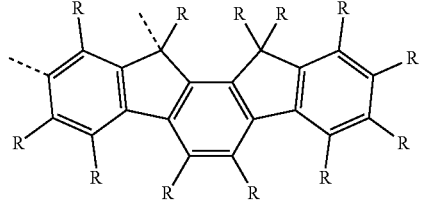

-continued
formula (42)
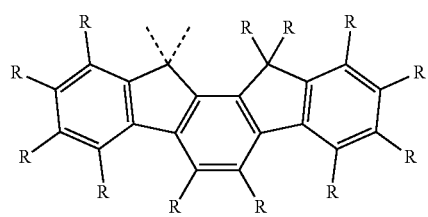
formula (43)
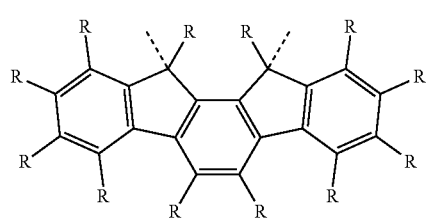
formula (44)
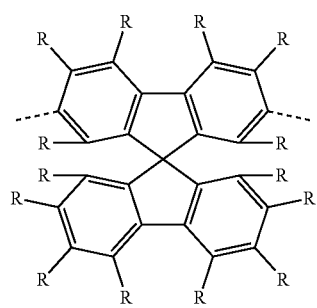
formula (45)
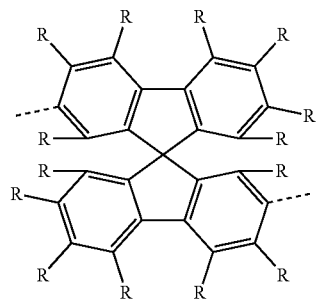
formula (46)
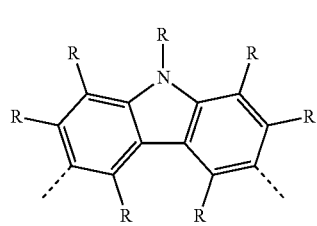
formula (47)
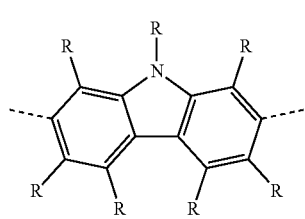
formula (48)
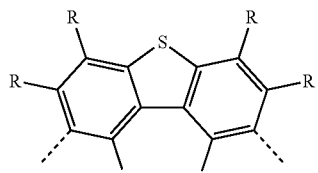
formula (49)
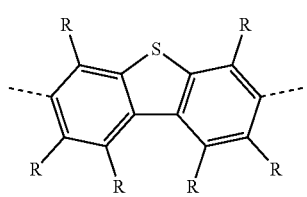
formula (50)
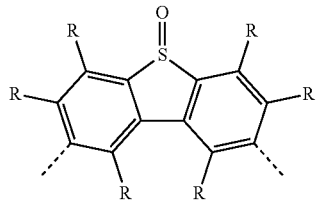
formula (51)
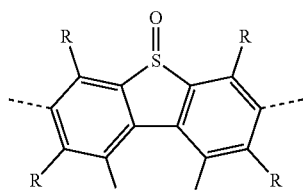
formula (52)
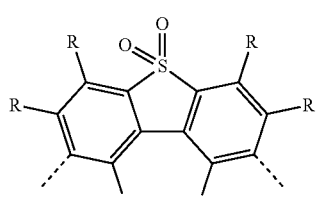
formula (53)
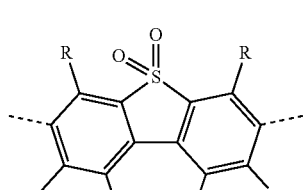
formula (54)
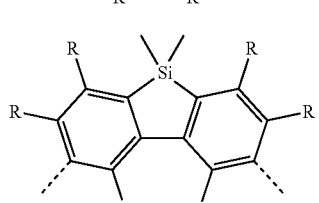
formula (55)
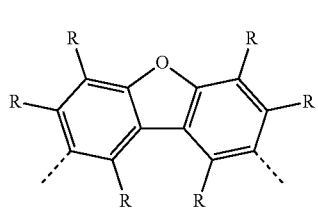

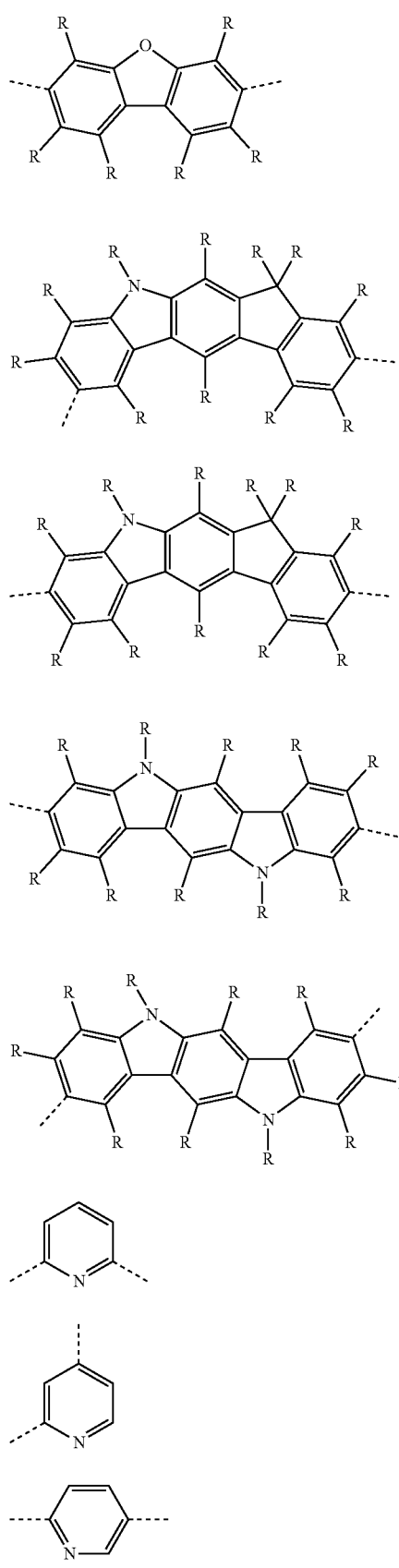
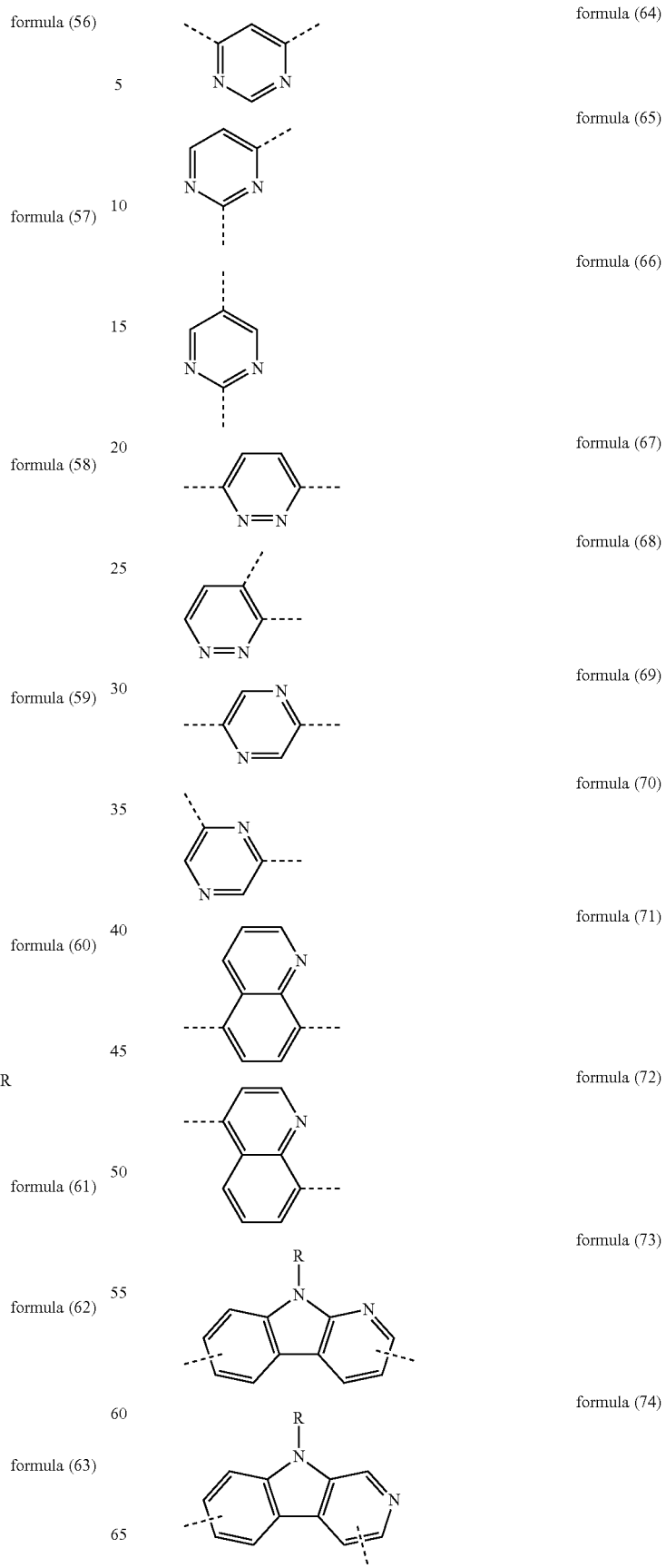

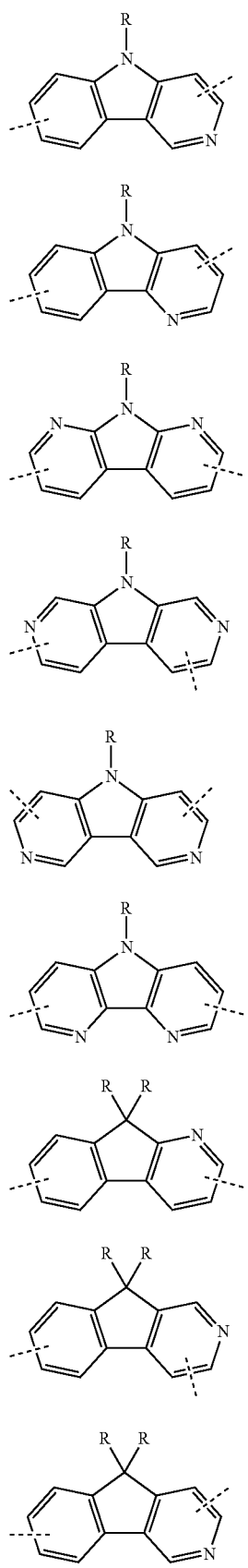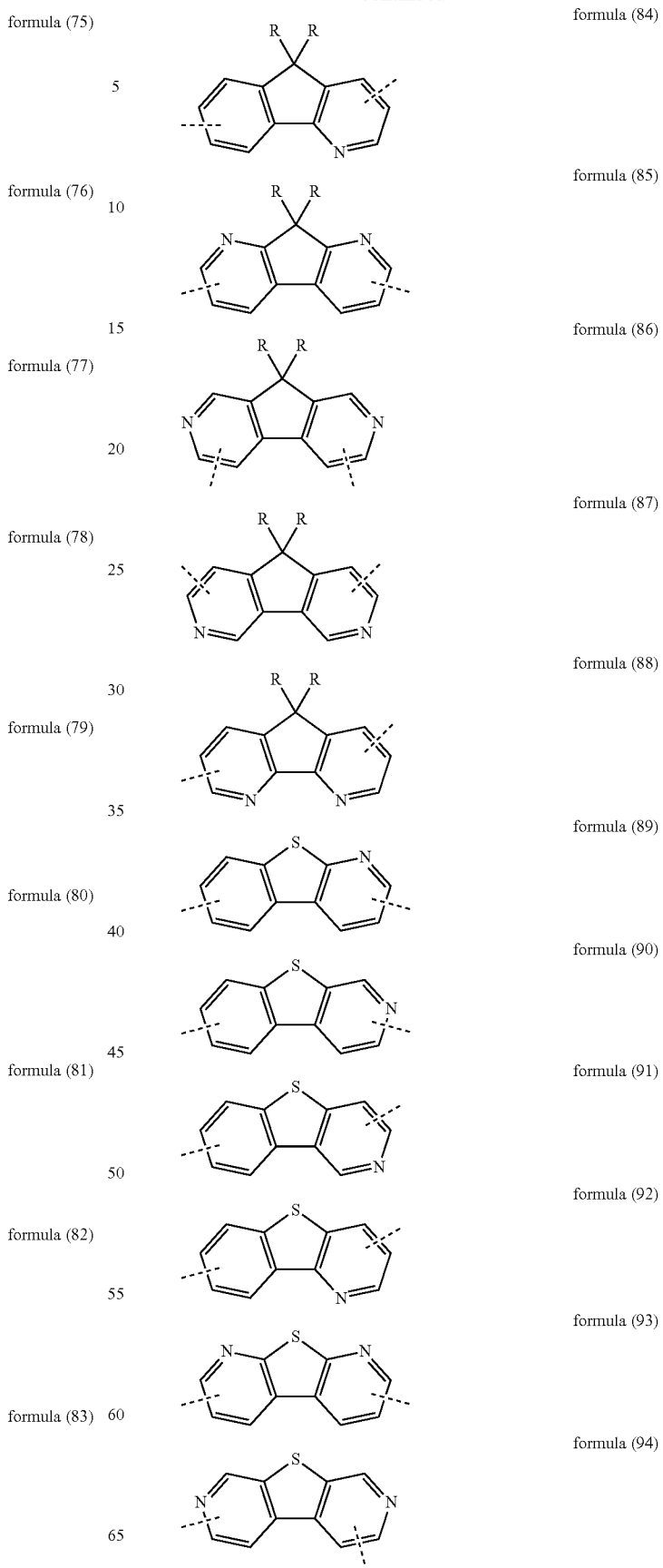

-continued formula (95)
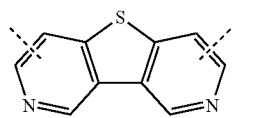

formula (96)
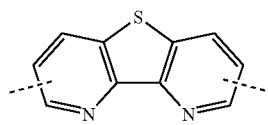

formula (97)
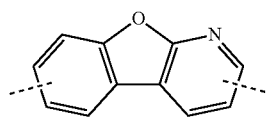

formula (98)
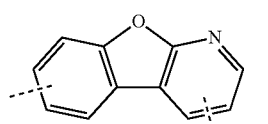

formula (99)
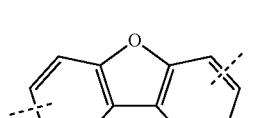

formula (100)
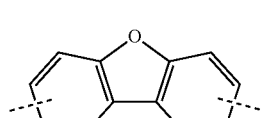

formula (101)
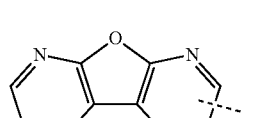

formula (102)
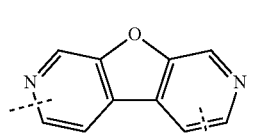

formula (103)
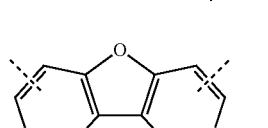

formula (104)
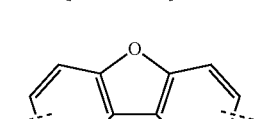

formula (105)
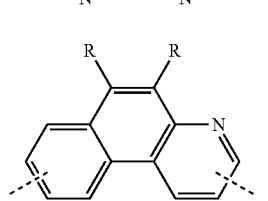

formula (106)
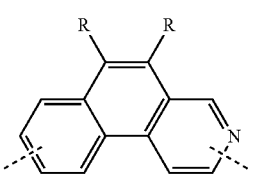

formula (107)
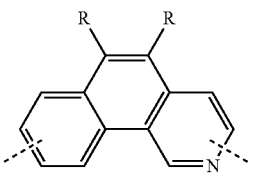

formula (108)
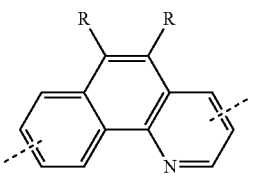

formula (109)
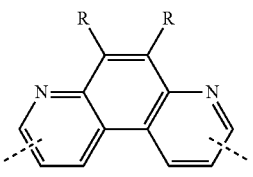

formula (110)
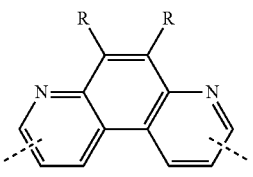

formula (111)
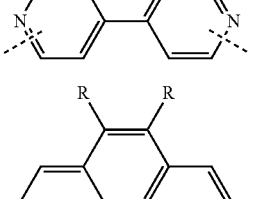

formula (112)
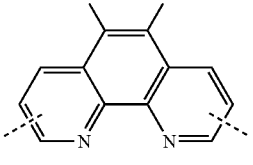

where the symbols used have the meanings given above and the dashed bonds indicate the positions at which the groups are bonded to the adjacent groups $Ar^3$ and $Ar^4$ or R. If a precise position of the bond is not indicated, this means that the bond can be in any position on this ring.

If L stands for an aromatic or heteroaromatic ring system which contains condensed aryl groups, L is then preferably selected from structures of the following formulae (113) to (116),

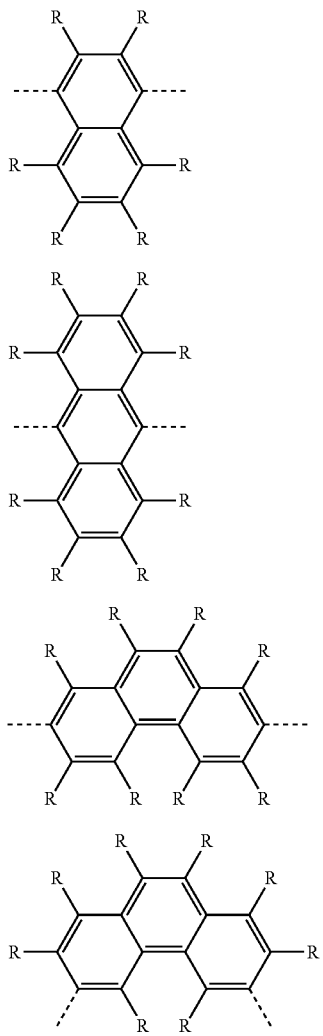

formula (113)

formula (114)

formula (115)

formula (116)

where the symbols used have the meanings given above and the dashed bonds indicate the positions at which the groups are bonded to the adjacent groups.

In a further preferred embodiment of the invention, $Ar^3$ and $Ar^4$ are selected, identically or differently on each occurrence, from structures of the above-mentioned formulae (18) to (116). If the compound is employed as triplet matrix material, $Ar^3$ and $Ar^4$ are preferably selected, identically or differently, from the above-mentioned formulae (18) to (112), in particular from the formulae (18) to (104).

In a further preferred embodiment of the invention, the index n=1, i.e. the bridging unit has the structure —$Ar^3$-L-$Ar^4$—. The bridging unit L here preferably has a structure of the following formula (117):

formula (117)

where:
Y is, identically or differently on each occurrence, $CR_2$, $SiR_2$, $GeR_2$, S or O;
p is 0, 1, 2, 3, 4, 5 or 6, preferably 0, 1 or 2;
q is 0, 1, 2, 3 or 4, preferably 0, 1 or 2;
p+q>0;
with the proviso that a plurality of heteroatoms are not bonded directly to one another.

Examples of suitable groups $Ar^3$-L-$Ar^4$ are the following groups:

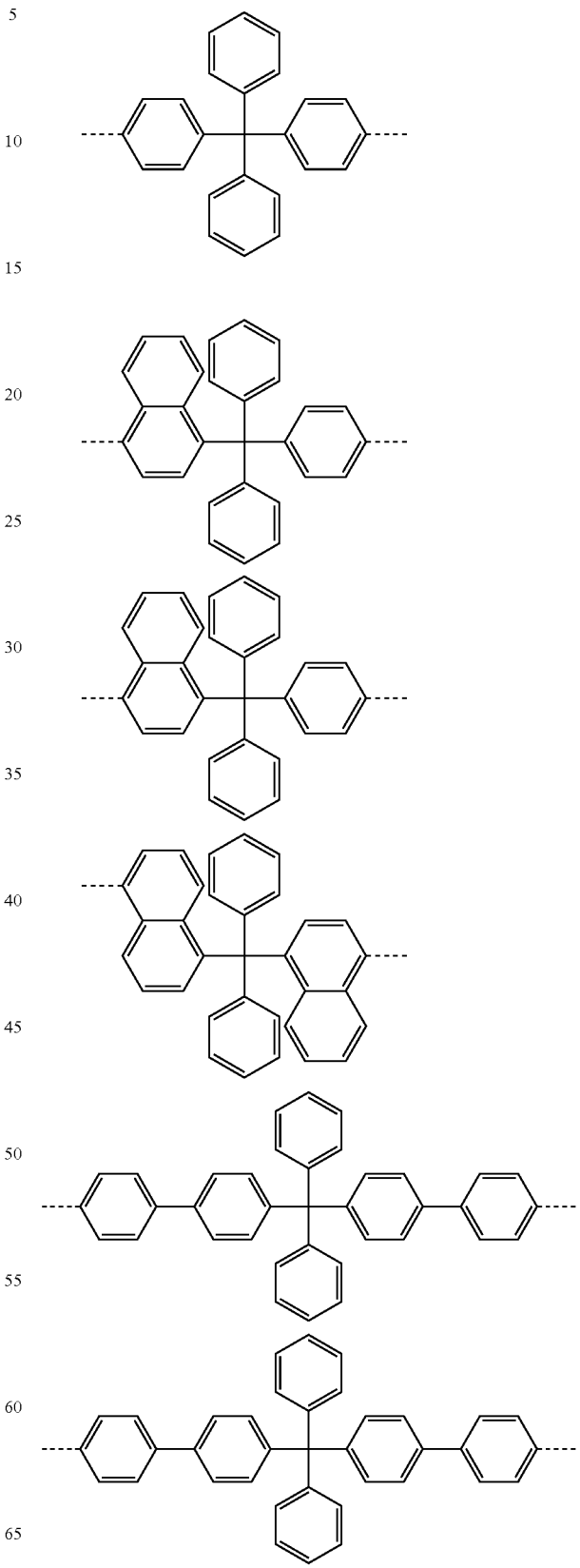

23
-continued
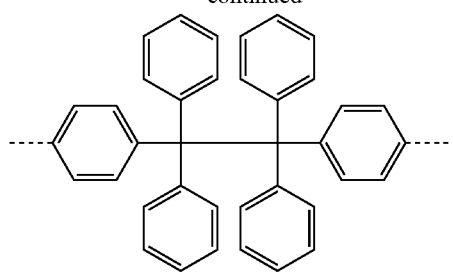
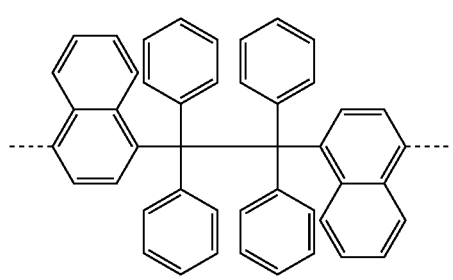
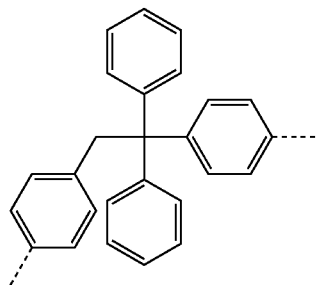
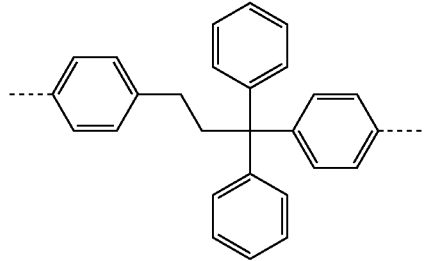
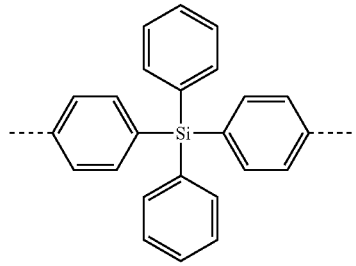
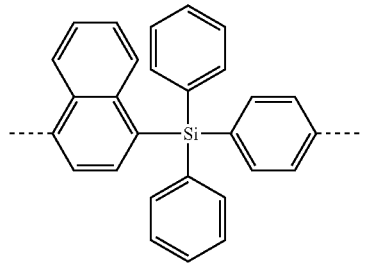
24
-continued
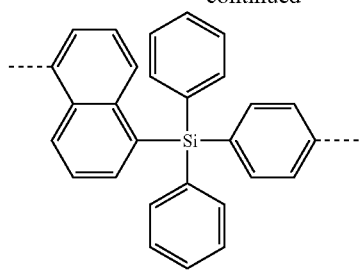
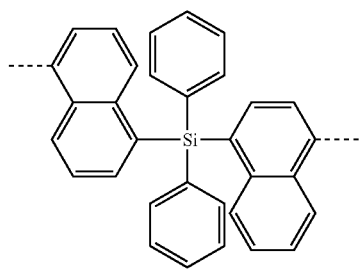
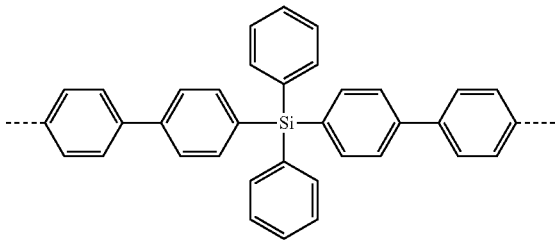
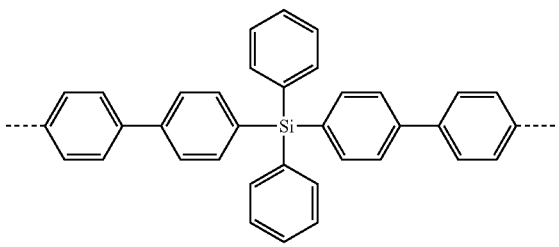
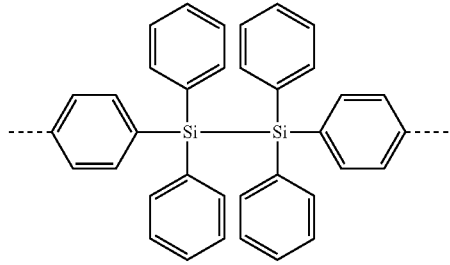
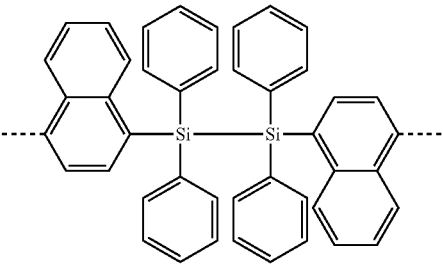

25
-continued
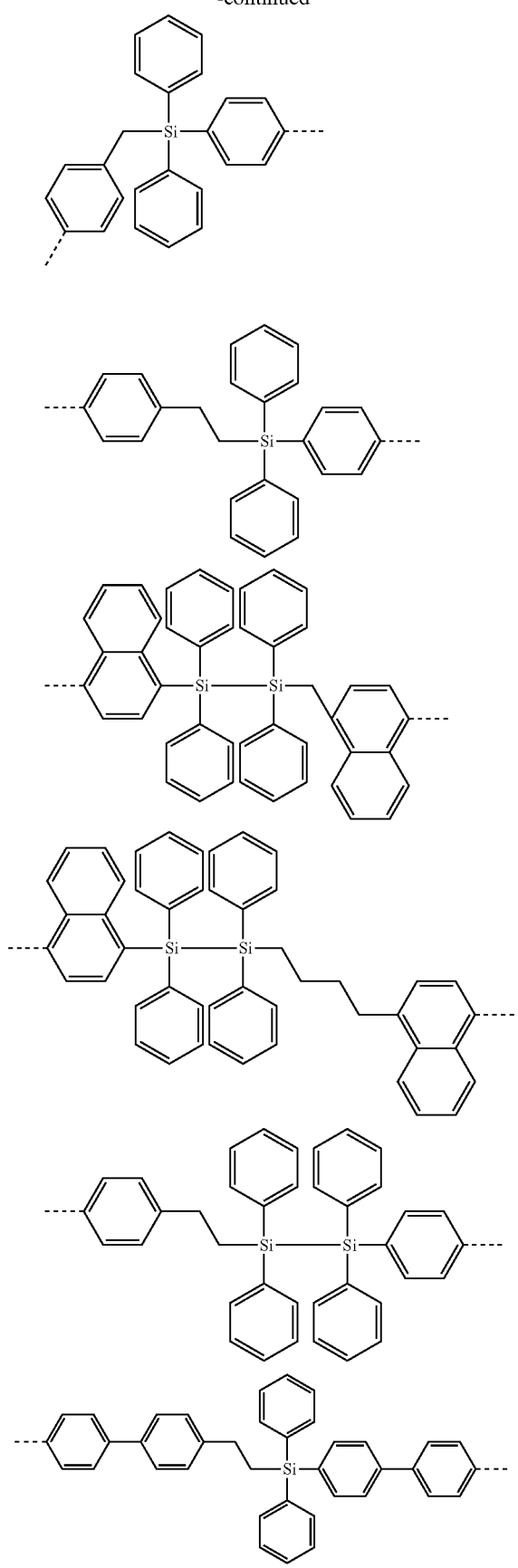
26
-continued
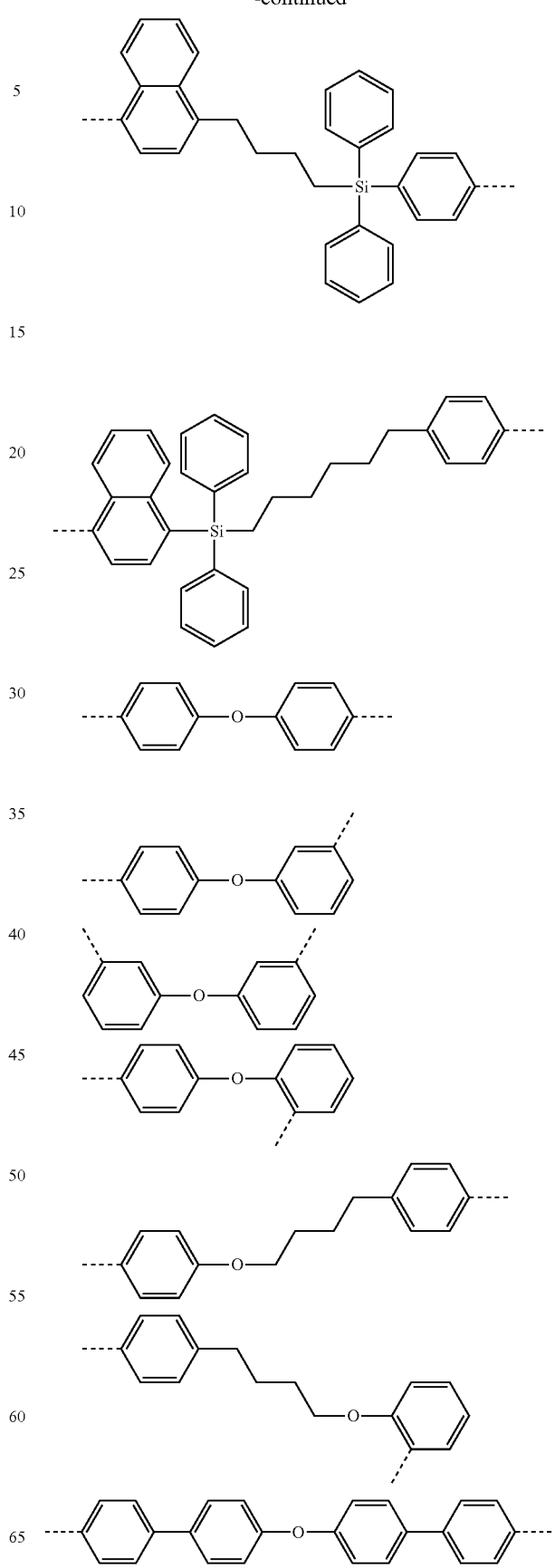

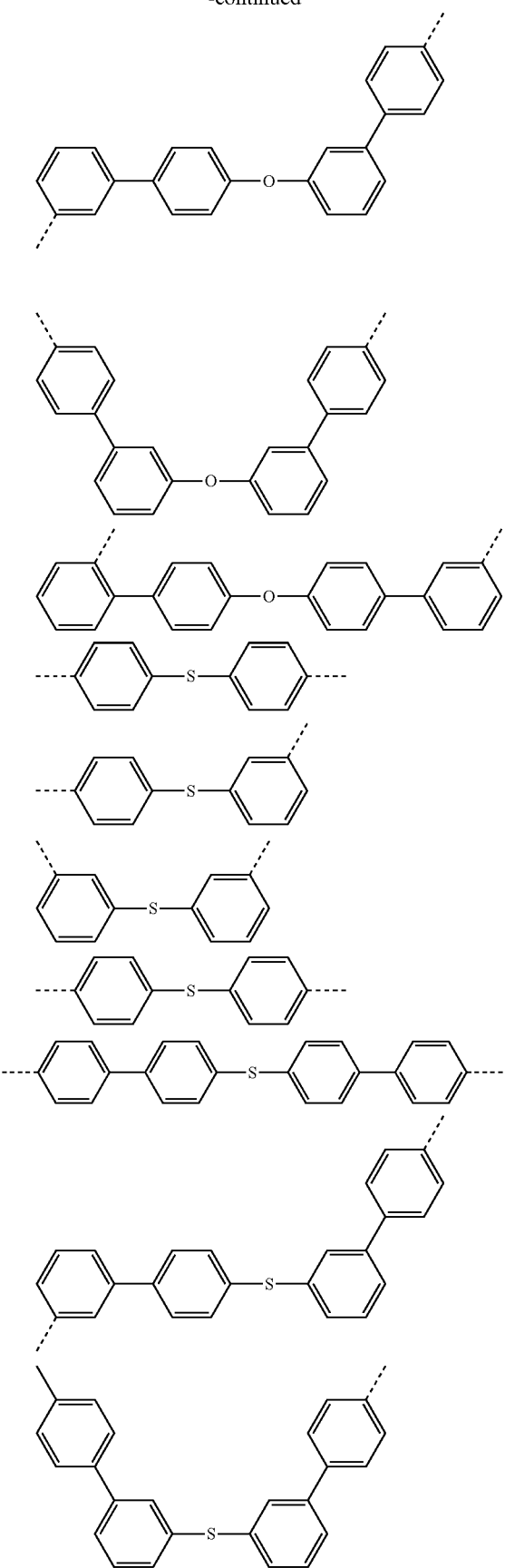

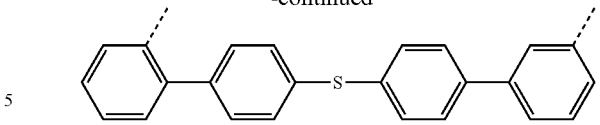

In a preferred embodiment of the invention, R is selected, identically or differently on each occurrence, from the group consisting of H, D, F, Cl, Br, CN, C(=O)Ar, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by O and where one or more H atoms may be replaced by D or F, an aromatic or heteroaromatic ring system having 5 to 30 aromatic ring atoms, which may in each case be substituted by one or more radicals $R^2$, or an aryloxy or heteroaryloxy group having 5 to 30 aromatic ring atoms, which may be substituted by one or more radicals $R^2$.

In a particularly preferred embodiment of the invention, R is selected, identically or differently on each occurrence, from the group consisting of H, D, F, CN, a straight-chain alkyl group having 1 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 18 aromatic ring atoms, which may in each case be substituted by one or more radicals $R^2$.

In a further preferred embodiment of the invention, the radical $R^1$ which is bonded to $Ar^1$ or $Ar^3$ is selected, identically or differently on each occurrence, from the group consisting of H, D or an aromatic or heteroaromatic ring system having 6 to 18 aromatic ring atoms which contains no condensed aryl groups, where the aromatic or heteroaromatic ring system is, in particular, selected from the group consisting of phenyl, ortho-, meta- or para-biphenyl, ortho-, meta-, para- or branched terphenyl and quaterphenyl.

For compounds which are processed by vacuum evaporation, the alkyl groups preferably have not more than four C atoms, particularly preferably not more than 1 C atom. For compounds which are processed from solution, suitable compounds are also those which are substituted by linear, branched or cyclic alkyl groups having up to 10 C atoms or which are substituted by oligoarylene groups, for example ortho-, meta-, para- or branched terphenyl or quaterphenyl groups.

In a preferred embodiment of the invention, $R^2$ is selected, identically or differently on each occurrence, from the group consisting of H, D, F, CN, a straight-chain alkyl group having 1 to 10 C atoms or a branched or cyclic alkyl group having 3 to 10 C atoms, where one or more H atoms may be replaced by D or F, or an aromatic or heteroaromatic ring system having 5 to 30 aromatic ring atoms, which may in each case be substituted by one or more radicals $R^3$.

In a particularly preferred embodiment of the invention, $R^2$ is selected, identically or differently on each occurrence, from the group consisting of H, D, F, CN, a straight-chain alkyl group having 1 to 5 C atoms or a branched or cyclic alkyl group having 3 to 5 C atoms, or an aromatic or heteroaromatic ring system having 5 to 18 aromatic ring atoms.

Particular preference is given to compounds of the formula (1) in which the preferred embodiments mentioned above occur simultaneously. Particular preference is therefore given to compounds of the formula (1) for which:

Ar¹, Ar² is selected, identically or differently on each occurrence, from the groups of the above-mentioned formulae (3) to (12);

L is a single bond, a divalent straight-chain alkylene or alkylidene group having 1 to 10 C atoms, in particular having 1 to 5 C atoms, or a branched or cyclic alkylene or alkylidene group having 3 to 10 C atoms, in particular having 3 to 6 C atoms, which may be substituted by in each case one or more radicals R, where one or more $CH_2$ groups, which are preferably not bonded directly to N and are preferably not adjacent, may be replaced by $Si(R)_2$, C=O, P(=O)R, S=O, $SO_2$, —O—, —S— or —CONR— and where one or more H atoms may be replaced by D or F, or a divalent aromatic or heteroaromatic ring system having 5 to 24 aromatic ring atoms, which may also be substituted by one or more radicals R, or $Si(R)_2$, C(=O), S(=O), $SO_2$, P(=O)R, O or S;

R is selected, identically or differently on each occurrence, from the group consisting of H, D, F, Cl, Br, CN, C(=O)Ar, a straight-chain alkyl or alkoxy group having 1 to 10 C atoms or a branched or cyclic alkyl or alkoxy group having 3 to 10 C atoms, each of which may be substituted by one or more radicals $R^2$, where one or more non-adjacent $CH_2$ groups may be replaced by O and where one or more H atoms may be replaced by D or F, an aromatic or heteroaromatic ring system having 5 to 30 aromatic ring atoms, which may in each case be substituted by one or more radicals $R^2$, or an aryloxy or heteroaryloxy group having 5 to 30 aromatic ring atoms, which may be substituted by one or more radicals $R^2$;

$R^1$ is selected, identically or differently on each occurrence, from the group consisting of H, D or an aromatic or heteroaromatic ring system having 6 to 18 aromatic ring atoms which contains no condensed aryl groups;

$R^2$ is selected, identically or differently on each occurrence, from the group consisting of H, D, F, CN, a straight-chain alkyl group having 1 to 10 C atoms or a branched or cyclic alkyl group having 3 to 10 C atoms, where one or more H atoms may be replaced by D or F, or an aromatic or heteroaromatic ring system having 5 to 30 aromatic ring atoms, which may in each case be substituted by one or more radicals $R^3$;

the other symbols and indices have the meanings given above.

Very particular preference is given to compounds of the formula (1) for which:

—NAr¹Ar² is selected from the groups of the above-mentioned formulae (13) to (17);

L is a single bond, a divalent aromatic or heteroaromatic ring system having 6 to 24 aromatic ring atoms, which may be substituted by one or more radicals R, or $Si(R)_2$ or C(=O); L here, if L stands for an aromatic or heteroaromatic ring system, is preferably selected from the above-mentioned formulae (18) to (116);

Ar³, Ar⁴ is selected, identically or differently on each occurrence, from structures of the above-mentioned formulae (18) to (116);

R is selected, identically or differently on each occurrence, from the group consisting of H, D, F, CN, a straight-chain alkyl group having 1 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 18 aromatic ring atoms, which may in each case be substituted by one or more radicals $R^2$;

$R^1$ is selected, identically or differently on each occurrence, from the group consisting of H, D, phenyl, ortho-, meta- or para-biphenyl, ortho-, meta-, para- or branched terphenyl and quaterphenyl;

$R^2$ is selected, identically or differently on each occurrence, from the group consisting of H, D, F, CN, a straight-chain alkyl group having 1 to 5 C atoms or a branched or cyclic alkyl group having 3 to 5 C atoms, or an aromatic or heteroaromatic ring system having 5 to 18 aromatic ring atoms;

the other symbols and indices have the meanings given above.

Examples of preferred compounds in accordance with the above-mentioned embodiments are the compounds of the following structures.

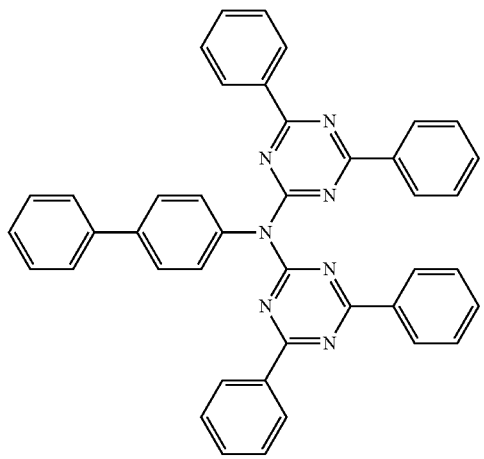
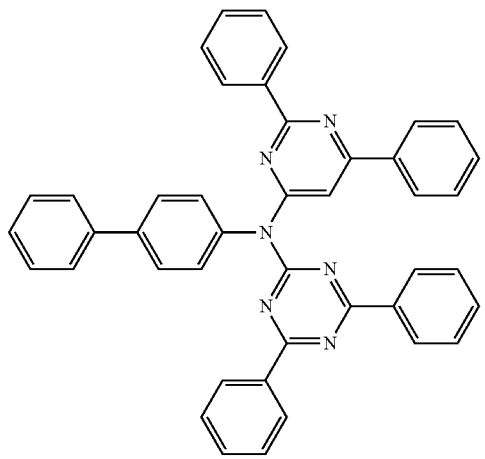

31
32
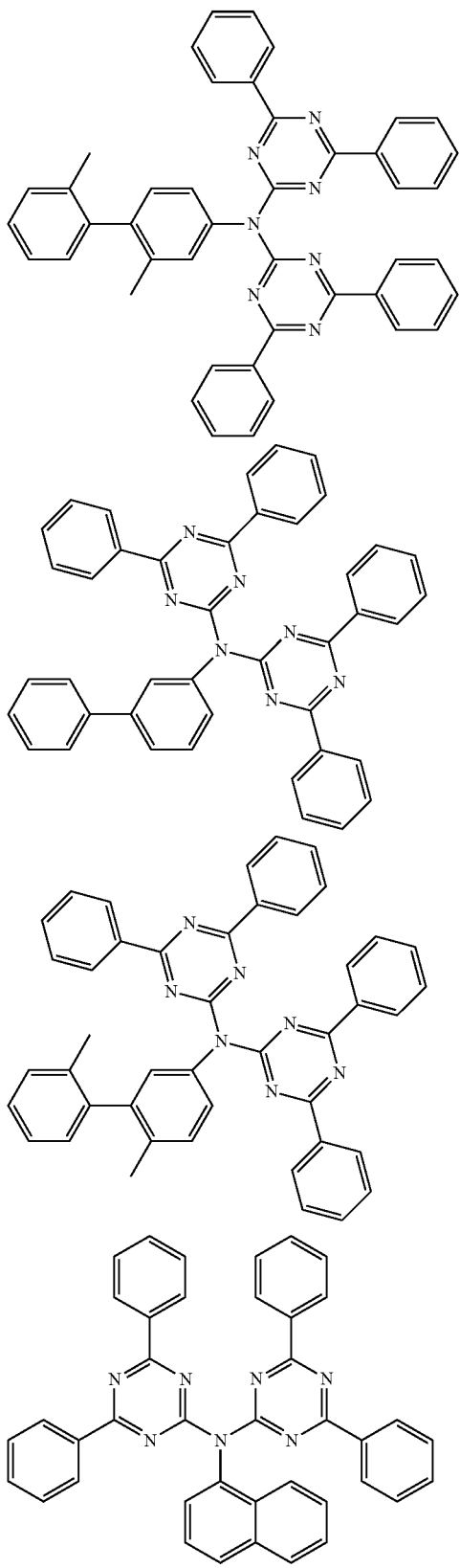
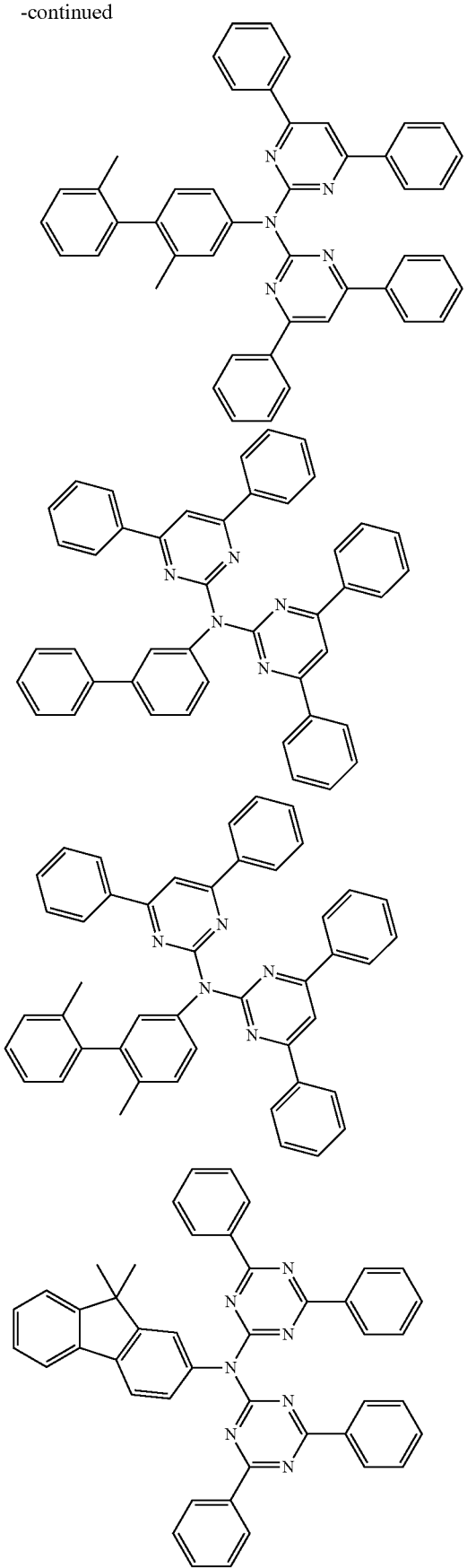

-continued
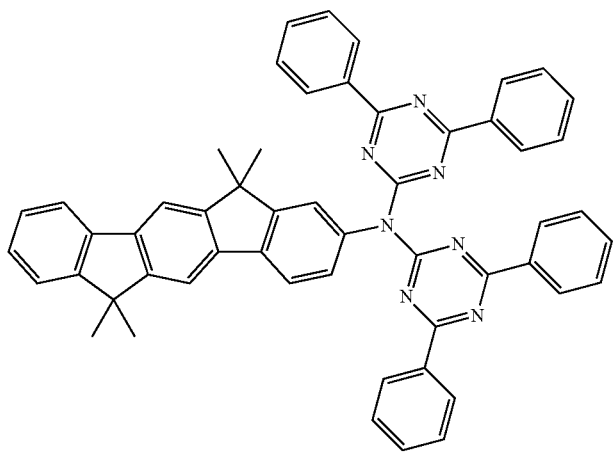
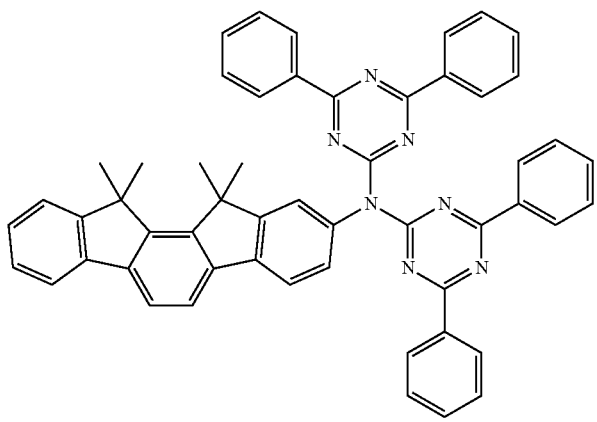
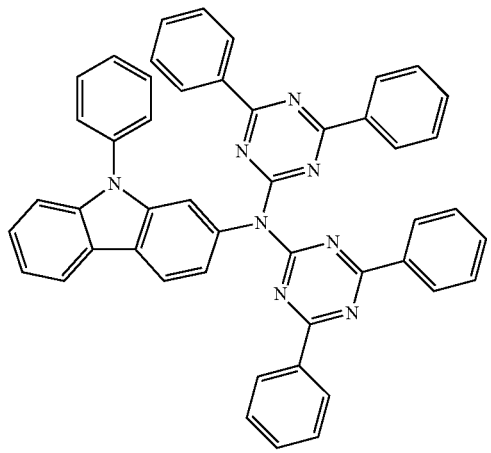
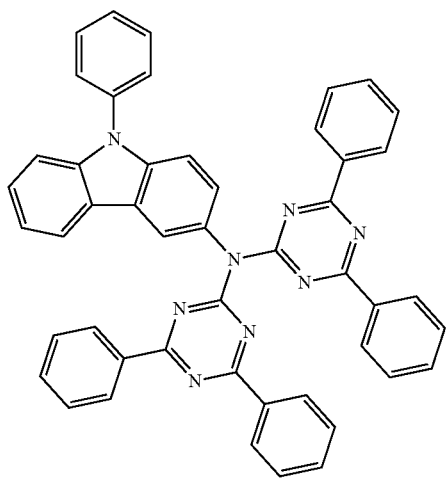
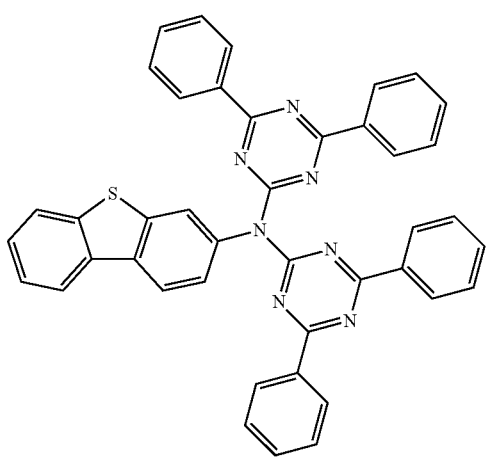

-continued
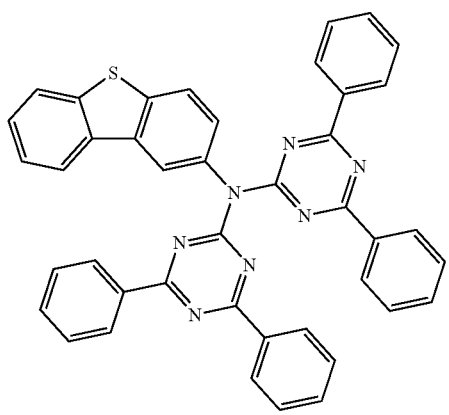
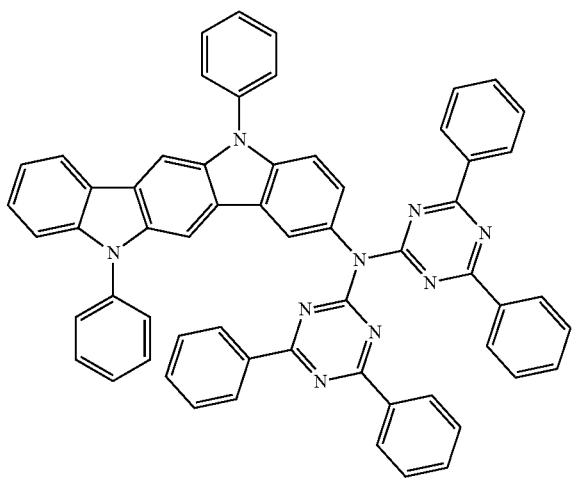
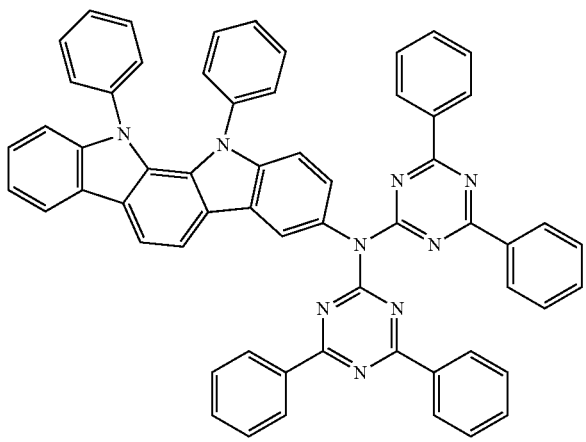
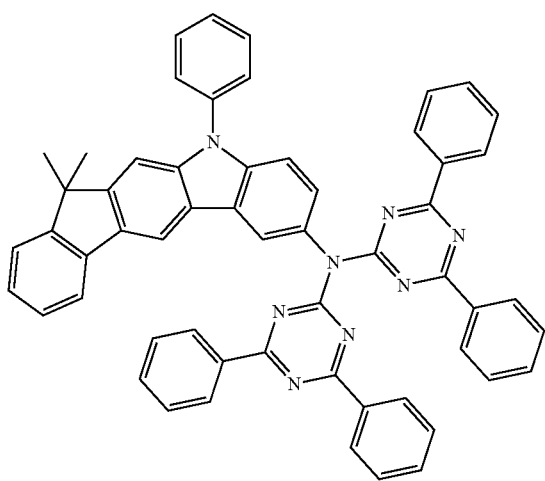

37
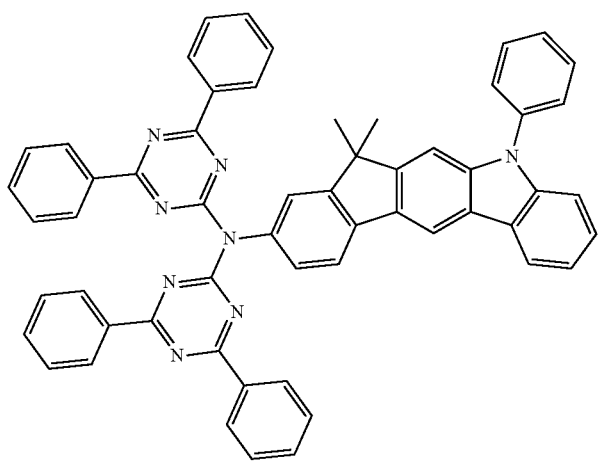
38
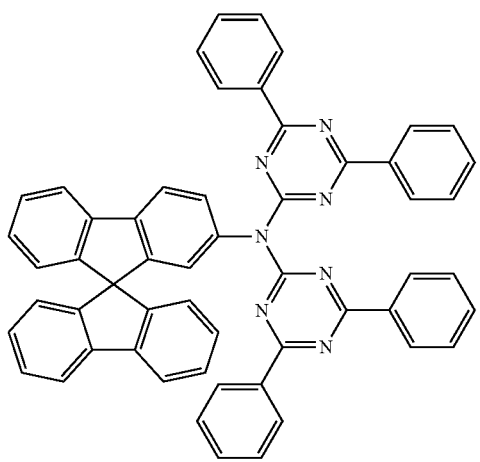
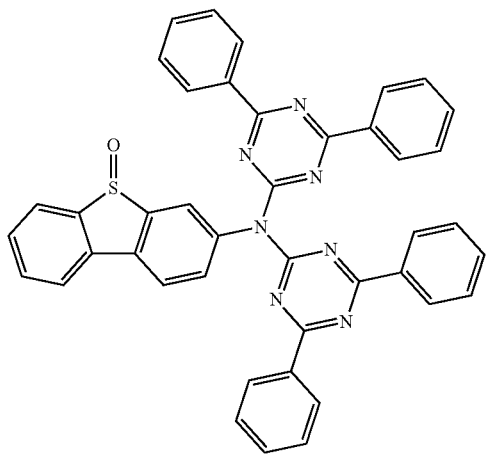
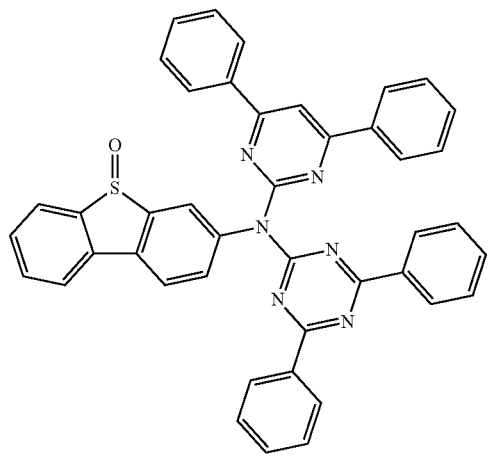
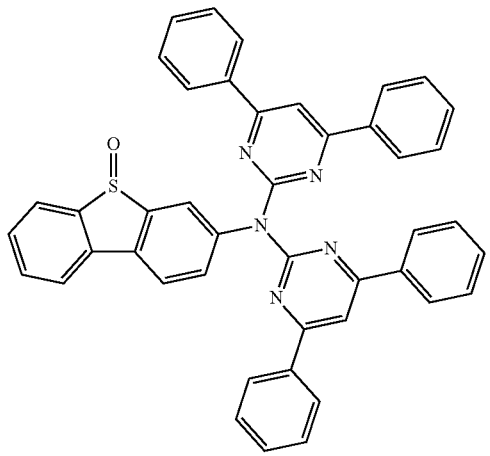
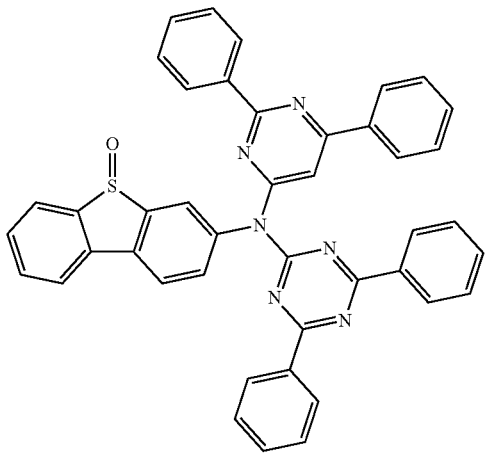

-continued
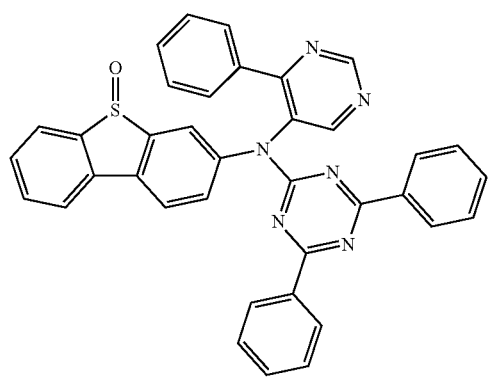
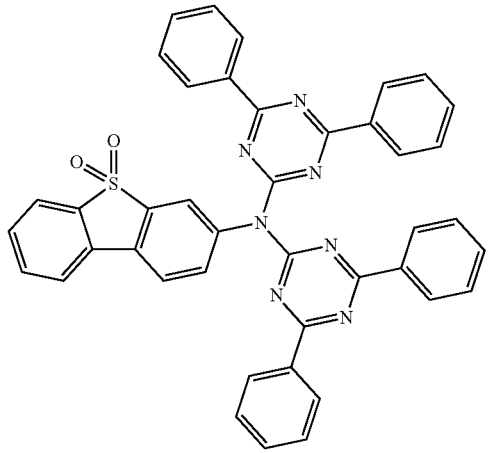
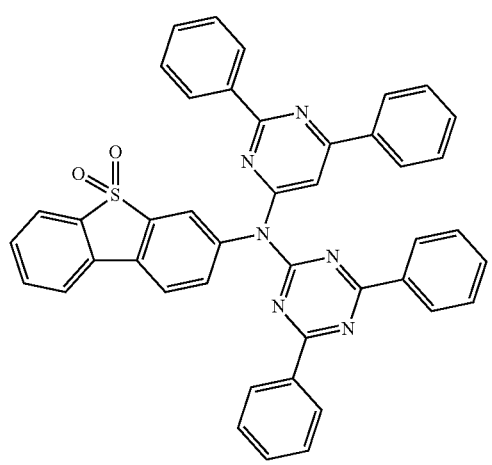
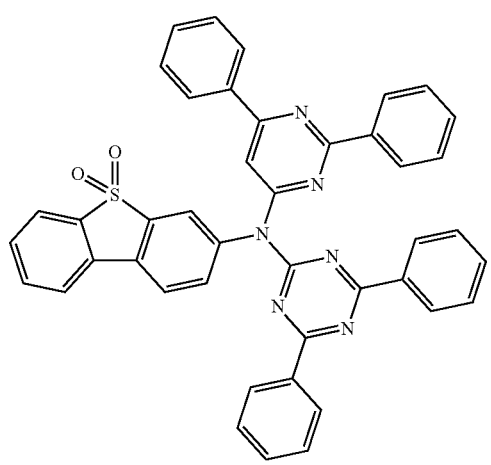
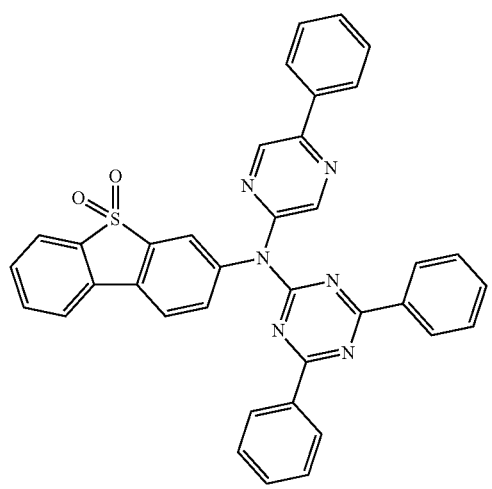
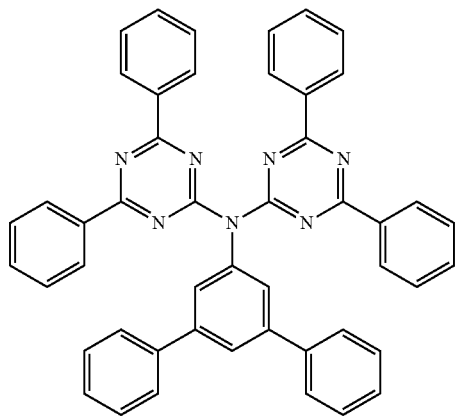

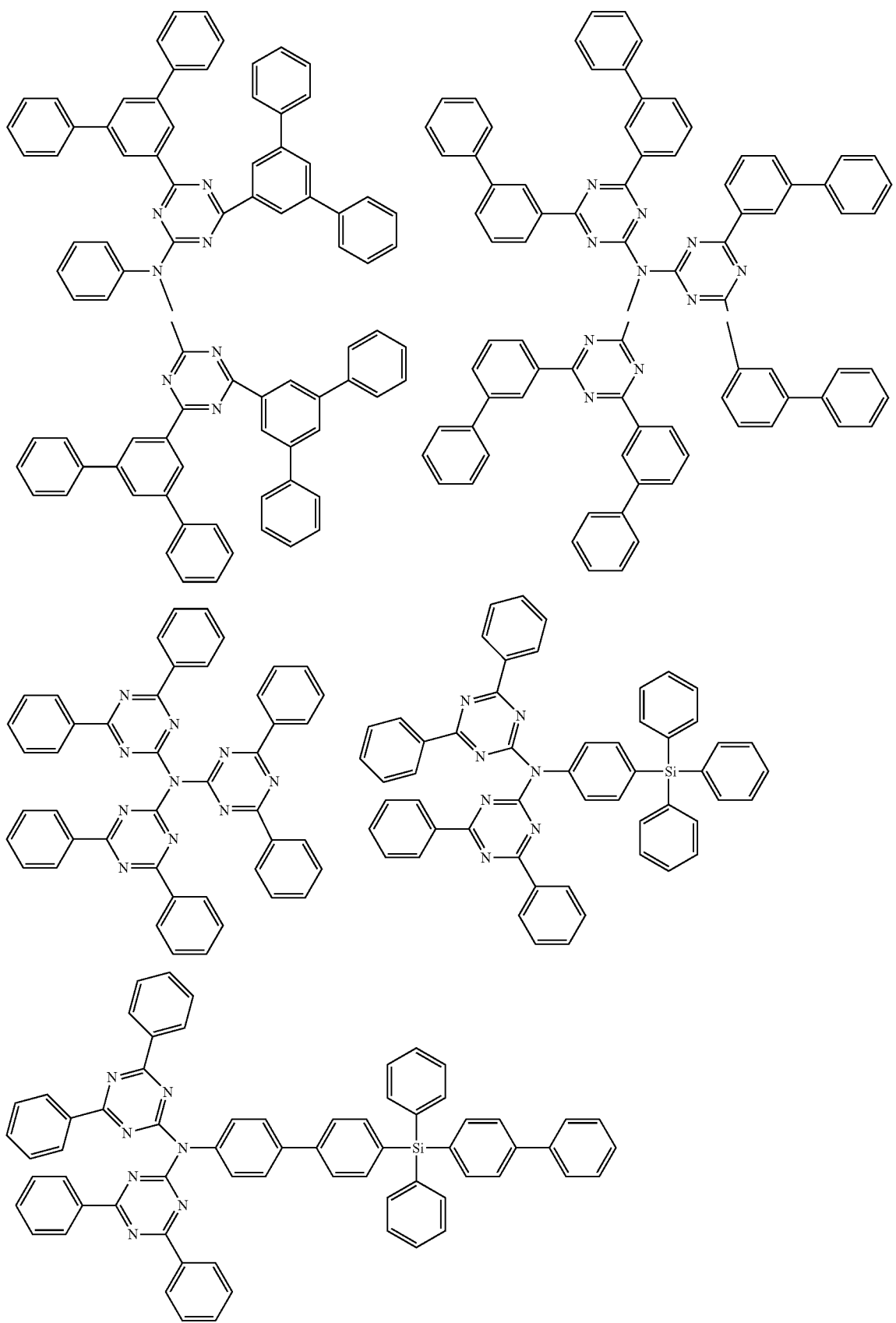

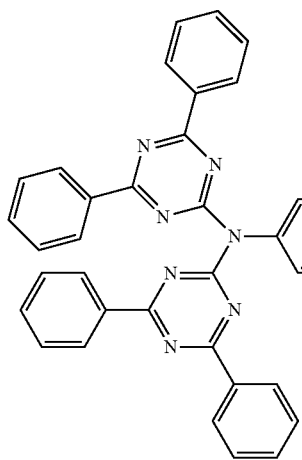
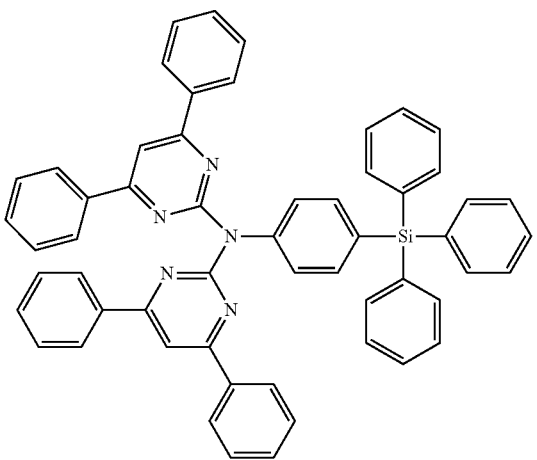
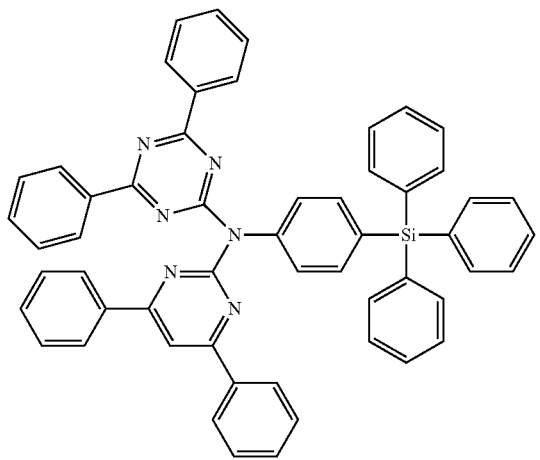
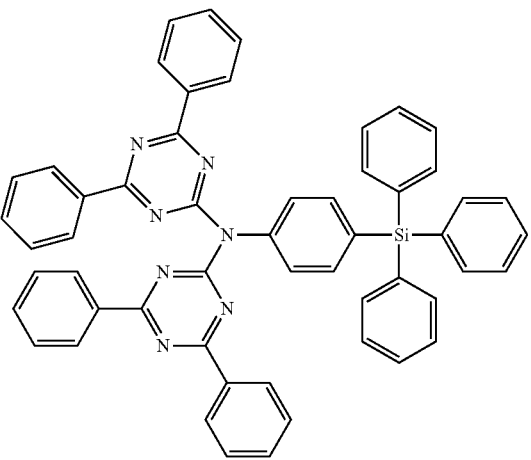
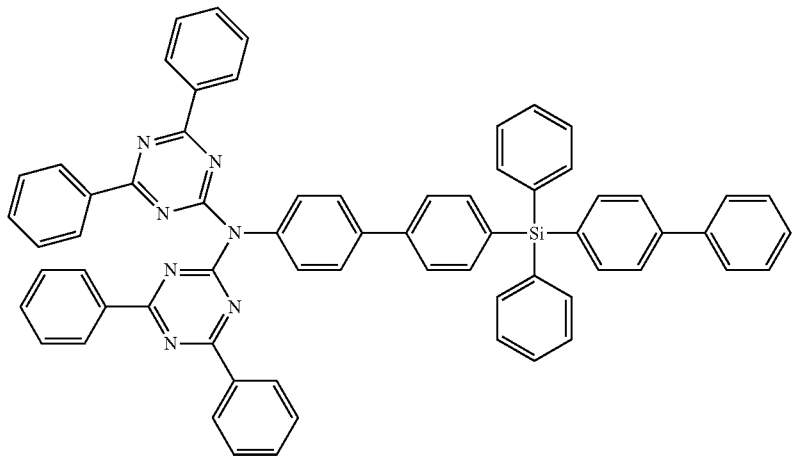

-continued
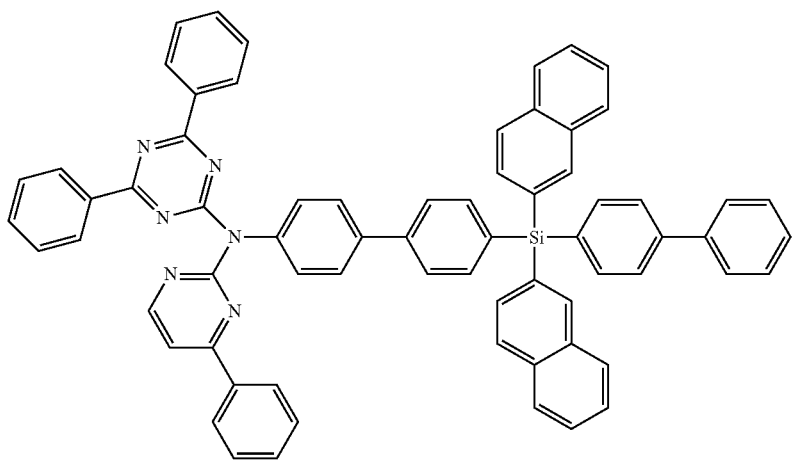
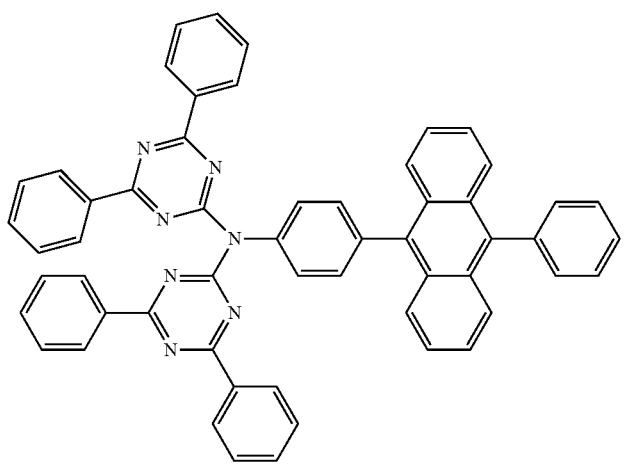
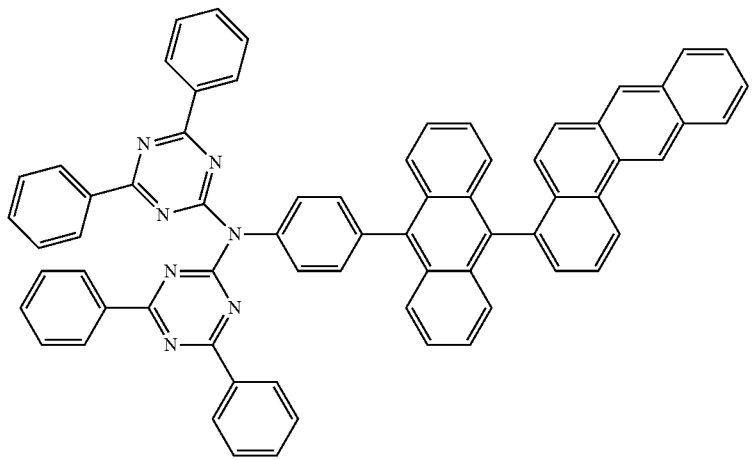

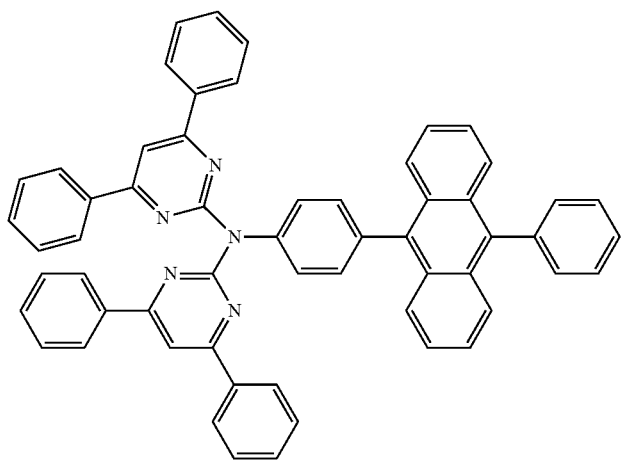
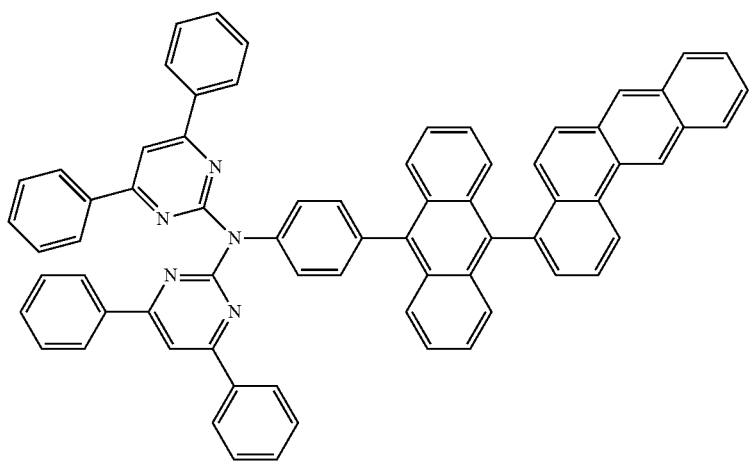
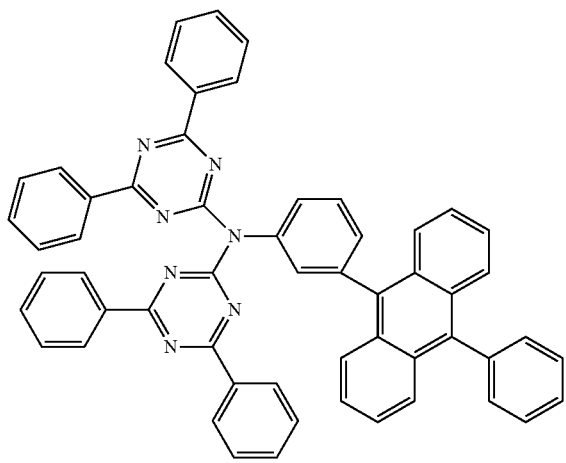

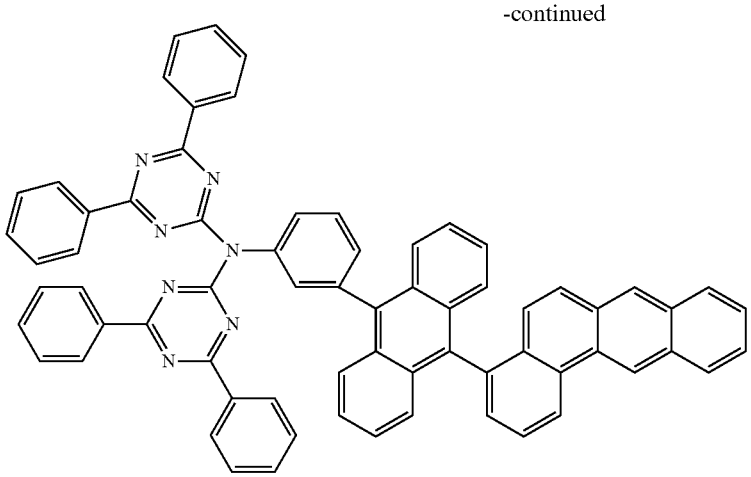

The compounds according to the invention can be prepared by synthetic steps known to the person skilled in the art, such as, for example, bromination, Ullmann arylation, Hartwig-Buchwald coupling, etc., as depicted in Scheme 1 for an illustrative compound. Further derivatives of the compounds according to the invention can be prepared entirely analogously. a suitable reactive group for the coupling reaction is, for example, a boronic acid or a boronic acid ester. Suitable coupling reactions are, for example, Suzuki coupling or Stille coupling.

Scheme 1

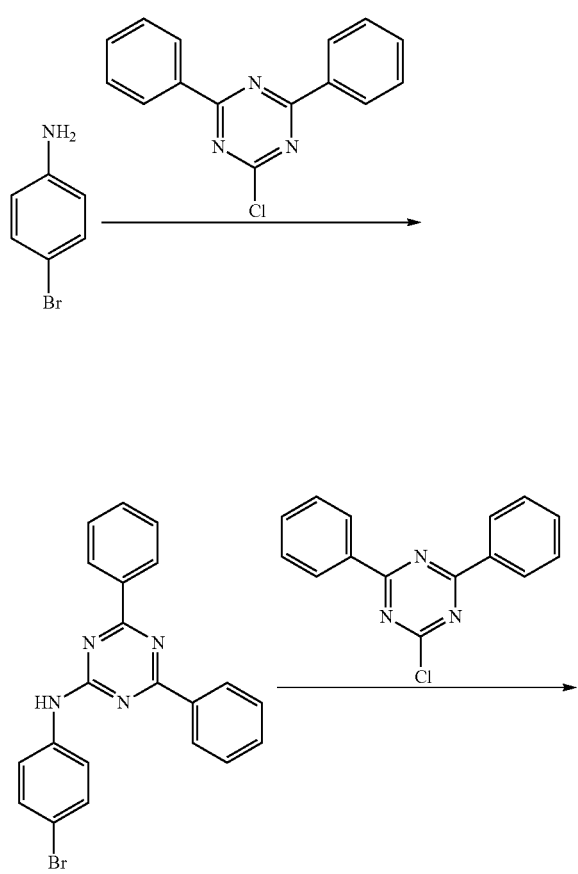

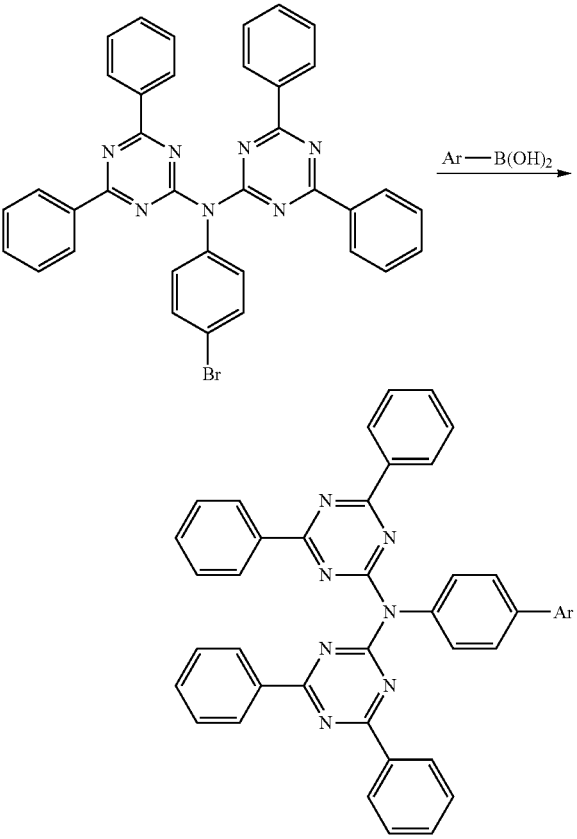

The present invention therefore furthermore relates to a process for the preparation of a compound of the formula (1), comprising the reaction steps:

a) synthesis of a compound G-L-Ar$^3$—NAr$^1$Ar$^2$ by reaction of a compound G-L-Ar$^3$—NH$_2$ with a compound G-Ar$^1$ and G-Ar$^2$, optionally with addition of a base and/or a catalyst, where G stands for a reactive leaving group, in particular fluorine, chlorine, bromine or iodine; and b) introduction of the group Ar$^4$ or R by coupling a group R-Ar$^4$-G or R-G to Ar$^3$ or L, for example by Suzuki coupling.

The reactive leaving group in step b) is preferably selected from Cl, Br, I, boronic acid or boronic acid derivatives, in particular boronic acid esters, triflate or tosylate.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the preparation of corresponding oligomers, dendrimers or polymers. The oligomerisation or polymerisation here is preferably carried out via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers comprising one or more of the compounds according to the invention mentioned above, where one or more bonds are present from the compound according to the invention to the polymer, oligomer or dendrimer.

Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers, where the units of the formula (1) are present in a proportion of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/22026), spirobifluorenes (for example in accordance with EP 707020, EP 894107 or WO 2006/061181), para-phenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers may also comprise further units, for example hole-transport units, in particular those based on triarylamines, and/or electron-transport units. In addition, the polymers can either comprise triplet emitters in copolymerised form or mixed in as a blend. Precisely the combination of units of the formula (1) with triplet emitters gives particularly good results.

The compounds according to the invention are suitable for use in an electronic device. An electronic device here is taken to mean a device which comprises at least one layer which comprises at least one organic compound. However, the component here may also comprise inorganic materials or also layers built up entirely from inorganic materials.

The present invention therefore furthermore relates to the use of the compounds according to the invention in an electronic device, in particular in an organic electroluminescent device.

The present invention still furthermore relates to an electronic device comprising at least one of the compounds according to the invention. The preferences stated above likewise apply to the electronic devices.

The electronic device is preferably selected from the group consisting of organic electroluminescent devices (organic light-emitting diodes, OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells (ODSSCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., *Nature Photonics* 2008, 1-4), but preferably organic electroluminescent devices (OLEDs), particularly preferably phosphorescent OLEDs.

The organic electroluminescent devices and the light-emitting electrochemical cells can be used for various applications, for example for monochromatic or polychromatic displays, for lighting applications or for medical applications, for example in phototherapy.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present.

The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed in various layers, depending on the precise structure. Preference is given to an organic electroluminescent device comprising a compound of the formula (1) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a particularly preferred embodiment of the invention, the compound of the formula (1) is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1) is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this application, all luminescent complexes containing transition metals or lanthanoids, in particular all luminescent iridium, platinum and copper complexes, are to be regarded as phosphorescent compounds.

The mixture of the compound of the formula (1) and the emitting compound comprises between 99.9 and 1% by weight, preferably between 99 and 10% by weight, particularly preferably between 97 and 60% by weight, in particular between 95 and 80% by weight, of the compound of the formula (1), based on the entire mixture comprising emitter and matrix material. Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and matrix material. The limits indicated above apply, in particular, if the layer is applied from solution. If the layer is applied by vacuum evaporation, the same numerical values apply, where in this case the percentage is in each case indicated in vol.-%.

A further preferred embodiment of the present invention is the use of the compound of the formula (1) as matrix material for a phosphorescent emitter in combination with a further matrix material. Particularly suitable matrix materials which can be employed in combination with the compounds of the formulae (1) are aromatic ketones, aromatic phosphine oxides or aromatic sulfoxides or sulfones, for example in accordance with WO 2004/013080, WO 2004/093207, WO 2006/005627 or the unpublished application DE 102008033943.1, triarylamines, carbazole derivatives, for example CBP (N,N-biscarbazolylbiphenyl), m-CBP or the carbazole derivatives disclosed in WO 05/039246, US 2005/0069729, JP 2004/288381, EP 1205527 or WO 2008/086851, indolocarbazole derivatives, example in accordance with WO 2007/063754 or WO 2008/056746, indenocarbazole derivatives, for for example in accordance with WO 2010/136109 and WO 2011/000455, azacarbazole derivatives, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, fluorene derivatives, for example in accordance with WO 2009/124627, diazasilole or tetraazasilole derivatives, for example in accordance with WO 2010/054729, diazaphosphole derivatives, for example in accordance with WO 2010/054730, or bridged carbazole derivatives, for example in accordance with US 2009/0136779, WO 2010/050778 or in accordance with the unpublished applications DE 102009048791.3 and DE 102010005697.9. It is furthermore possible to use an electronically neutral co-host which has neither hole-transporting nor electron-transporting properties, as described, for example, in WO 2010/108579.

It is likewise possible to use two or more phosphorescent emitters in the mixture. The emitter, which emits at relatively short wavelength, is used here as co-host in the mixture.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 2000/70655, WO 2001/41512, WO 2002/02714, WO 2002/15645, EP 1191613, EP 1191612, EP 1191614, WO 2005/033244, WO 2005/019373, US 2005/0258742, WO 2009/146770, WO 2010/015307, WO 2010/031485, WO 2010/054731, WO 2010/054728, WO 2010/086089, WO 2010/099852 and WO 2010/102709. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

In a further embodiment of the invention, the organic electroluminescent device does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 2005/053051. It is furthermore possible to use a metal complex which is identical or similar to the metal complex in the emitting layer as hole-transport or hole-injection material directly adjacent to the emitting layer, as described, for example, in WO 2009/030981.

In a further preferred embodiment of the invention, the compound of the formula (1) is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, Liq (lithium hydroxyquinolinate). Also suitable is the combination of the compound according to the invention in an electron-transport layer with an electron-injection layer. Suitable materials for the electron-injection layer are, for eample, alkali or alkaline-earth metal fluorides, such as, for example, LiF.

In still a further preferred embodiment of the invention, the compound of the formula (1) is employed in a hole-blocking layer. A hole-blocking layer is taken to mean a layer which is directly adjacent to an emitting layer on the cathode side.

It is furthermore possible to use the compound of the formula (1) both in a hole-blocking layer or electron-transport layer and as matrix in an emitting layer.

In the further layers of the organic electroluminescent device according to the invention, it is possible to use all materials as usually employed in accordance with the prior art. The person skilled in the art will therefore be able, without an inventive step, to employ all materials known for organic electroluminescent devices in combination with the compounds of the formulae (1) according to the invention.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, LITI (light induced thermal imaging, thermal transfer printing), ink-jet printing, screen printing, flexographic printing or offset printing. Soluble compounds, which are obtained, for example, by suitable substitution, are necessary for this purpose. These processes are also suitable for oligomers, dendrimers and polymers. These processes are also particularly suitable for the compounds according to the invention, since they generally have very good solubility in organic solvents.

Also possible are hybrid processes, in which, for example, one or more layers are applied from solution and one or more further layers are applied by vapour deposition. Thus, for example, the emitting layer can be applied from solution and the electron-transport layer can be applied by vapour deposition.

These processes are generally known to the person skilled in the art and can be applied by him without inventive step to organic electroluminescent devices comprising the compounds according to the invention.

Formulations of the compounds according to the invention are necessary for the processing of the compounds according to the invention from the liquid phase, for example by spin coating or by printing processes. These formulations can be, for example, solutions, dispersions or mini emulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents.

The present invention therefore furthermore relates to a formulation, in particular a solution, dispersion or mini emulsion, comprising at least one compound of the formula (1) or a corresponding oligomer, polymer or dendrimer according to the invention and at least one solvent, in particular an organic solvent. The way in which such solutions can be prepared is known to the person skilled in the art and is described, for example, in WO 2002/072714, WO 2003/019694 and the literature cited therein.

The present invention furthermore relates to mixtures comprising at least one compound of the formula (1) or a corresponding oligomer, polymer or dendrimer according to the invention and at least one further compound. The further compound can be, for example, a fluorescent or phosphorescent dopant if the compound according to the invention is used as matrix material. Suitable fluorescent and phosphorescent dopants are mentioned above in connection with the organic electroluminescent devices and are also preferred for the mixtures according to the invention.

The compounds according to the invention and the organic electroluminescent devices according to the invention are distinguished by the following surprising advantages over the prior art:

1. The compounds according to the invention are very highly suitable for use in an electron-transport layer in an organic electroluminescent device.
2. The compounds according to the invention, employed as matrix material for fluorescent or phosphorescent emitters, result in very high efficiencies and in long lifetimes. This applies, in particular, if the compounds are employed as matrix material for a phosphorescent emitter.
3. The compounds according to the invention are suitable not only as matrix for red- and green-phosphorescent compounds, but also for blue-phosphorescent compounds.
4. The compounds according to the invention have a small separation between the $S_1$ level, i.e. the first excited singlet level, and the $T_1$ level, i.e. the first excited triplet level, and should therefore be used particularly well for use in phosphorescent OLEDs.
5. The compounds according to the invention, employed in organic electroluminescent devices, result in high efficiencies and in steep current/voltage curves with low use and operating voltages.

These above-mentioned advantages are not accompanied by an impairment of the other electronic properties.

The invention is explained in greater detail by the following examples, without wishing it to be restricted thereby. The person skilled in the art will be able to use the descriptions to carry out the invention throughout the range disclosed and prepare further compounds according to the invention without inventive step and use them in electronic devices or use the process according to the invention.

EXAMPLES

The following syntheses are carried out, unless indicated otherwise, in dried solvents under a protective-gas atmosphere. Unless mentioned otherwise, the starting materials can be purchased from ALDRICH or ABCR. The purities indicated are determined by HPLC (UV detection at 320 nm), the glass-transition temperatures and melting points are determined by DSC.

Example 1

Biphenyl-4-ylbis(4,6-diphenyl-1,3,5-triazin-2-yl)amine a) (4-Bromophenyl)-(4,6-diphenyl-1,3,5-triazin-2-yl)amine (1a)

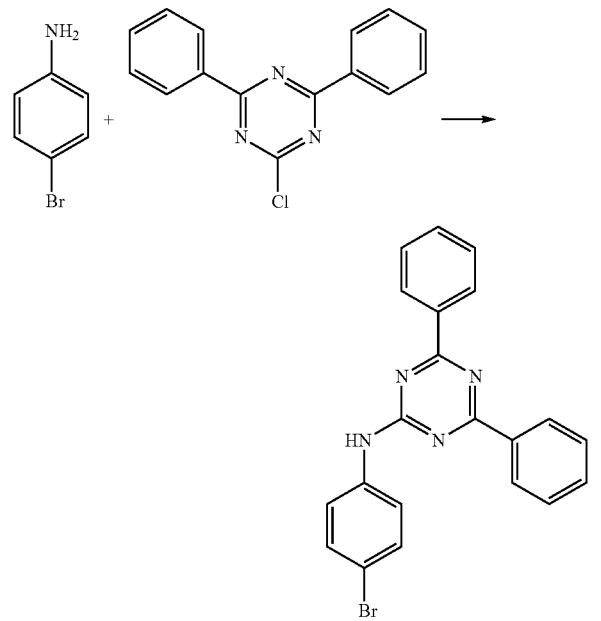

23.4 g (87.2 mmol) of 2-chloro-4,6-diphenyl-1,3,5-triazine in 400 ml of toluene are added to a vigorously stirred solution of 15.0 g (87.2 mmol) of 4-bromoaniline in 280 ml of pyridine and 400 ml of toluene, and the mixture is subsequently stirred at room temperature for 16 h. The solvent is subsequently removed in vacuo, and the residue is purified by chromatography (heptane/ethyl acetate 20:1). Yield: 21.1 g (52.3 mmol), 60%.

b) (4-Bromophenyl)bis(4,6-diphenyl-1,3,5-triazin-2-yl)amine (1b)

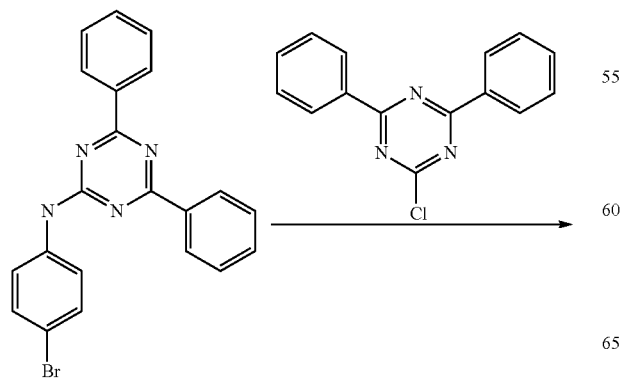

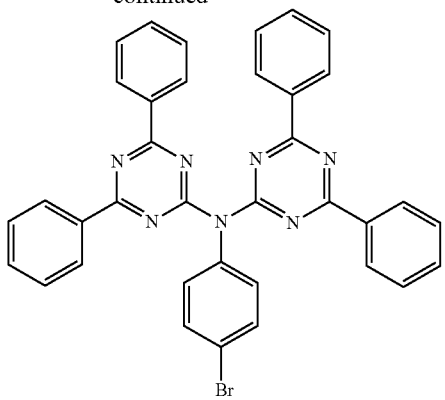

0.32 g (8 mmol) of NaH (60% in oil) are initially introduced in 100 ml of THF. A solution of 2.00 g (5 mmol) of 1a in 50 ml of THF is added dropwise thereto at room temperature. After 1 h, 1.35 g (5 mmol) of 2-chloro-4,6-diphenyl-1,3,5-triazine are added, the mixture is heated under reflux for 8 h and then stirred at room temperature for 12 h. The solvent is subsequently removed in vacuo, and the residue is purified by chromatography (heptane/ethyl acetate 20:1). Yield: 0.71 g (1.2 mmol), 22%.

c) Biphenyl-4-ylbis-(4,6-diphenyl-1,3,5-triazin-2-yl)amine

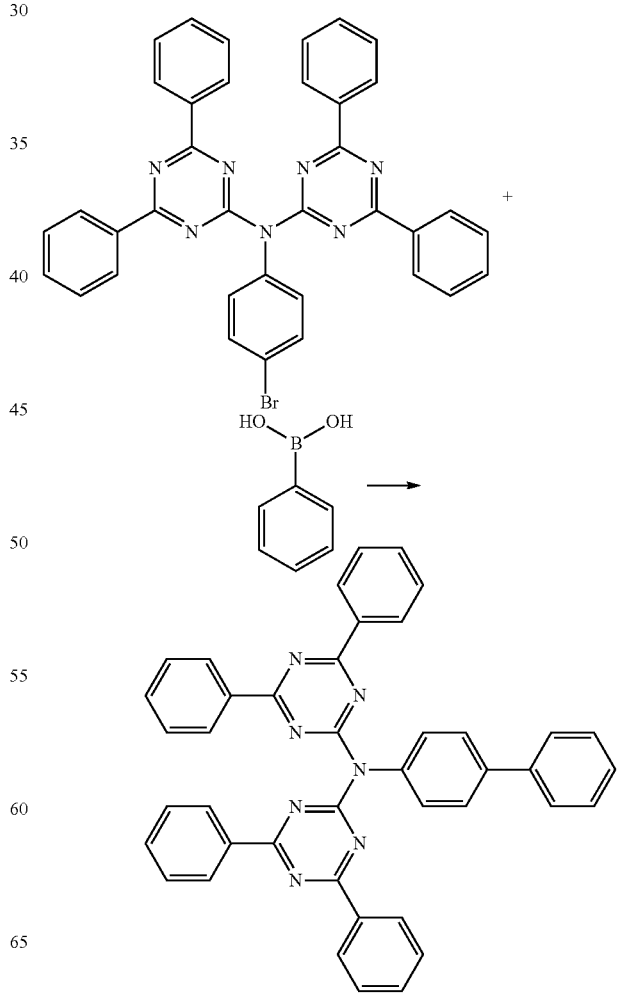

2.85 g (4.5 mmol) of 1b, 0.63 g (5.1 mmol) of phenylboronic acid (Optima Chemical Group LLC) and 2.40 g (10.5 mmol) of tripotassium phosphate are suspended in 100 ml of toluene, 100 ml of dioxane and 100 ml of water. 45.6 mg (0.15 mmol) of tri-o-tolylphosphine and then 17 mg (0.075 mmol) of palladium(II) acetate are added to this suspension, and the reaction mixture is heated under reflux for 16 h. After cooling, the organic phase is separated off, filtered through silica gel, washed three times with 20 ml of water and subsequently evaporated to dryness. The residue is recrystallised three times from toluene and sublimed in vacuo ($10^{-5}$ mbar, 340° C.). The yield is 1.11 g (1.76 mmol), corresponding to 39% of theory. Tg (DSC) 117° C., Tm (DSC) 301° C., purity>99.95%.

Example 2

Bis-(4,6-diphenyl-1,3,5-triazin-2-yl)-[4-(10-phenyl-anthracen-9-yl)phenyl]amine (2)

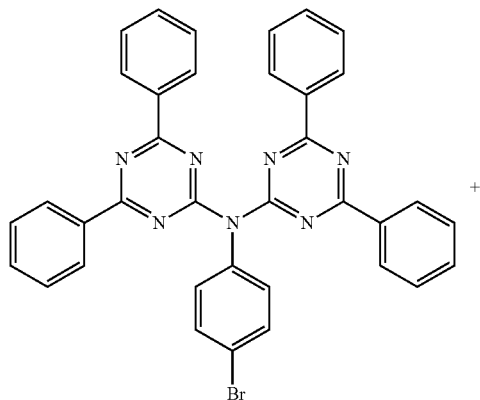

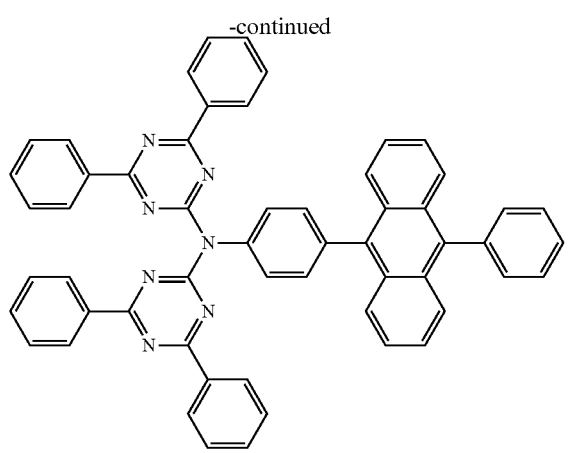

2.85 g (4.5 mmol) of 1b, 1.94 g (5.1 mmol) of (10-phenyl-9-anthracenyl)-boronic acid pinacol ester (Atomax Chemicals Co., Ltd) and 2.40 g (10.5 mmol) of tripotassium phosphate are suspended in 100 ml of toluene, 100 ml of dioxane and 100 ml of water. 45.6 mg (0.15 mmol) of tri-o-tolylphosphine and then 17 mg (0.075 mmol) of palladium(II) acetate are added to this suspension, and the reaction mixture is heated under reflux for 10 h. A further 0.64 g (1.7 mmol) of (10-phenyl-9-anthracenyl)boronic acid pinacol ester is then added, and the mixture is heated for a further 16 h. After cooling, the organic phase is separated off, filtered through silica gel, washed three times with 20 ml of water and subsequently evaporated to dryness. The residue is recrystallised three times from dioxane and sublimed in vacuo ($10^{-5}$ mbar, 370° C.). The yield is 1.64 g (2.03 mmol), corresponding to 45% of theory. Tg (DSC) 139° C., Tm (DSC) 323° C., purity>99.95%.

Example 3

Bis-(4,6-diphenyl-1,3,5-triazin-2-yl)-(9H-spirobifluoren-2-yl)amine (3)

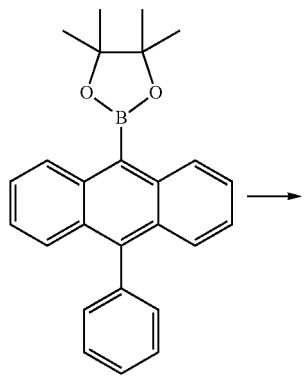

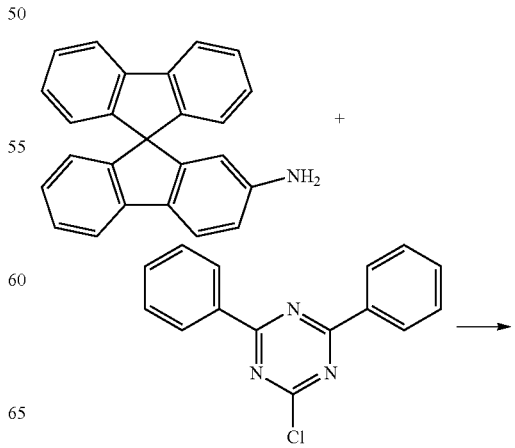

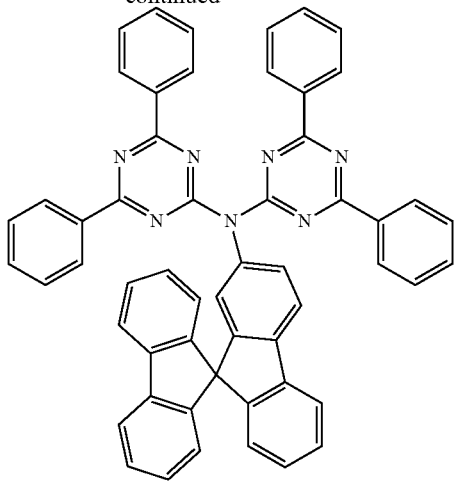

26.8 g (100 mmol) of 2-chloro-4,6-diphenyl-1,3,5-triazine in 200 ml of toluene are added to a vigorously stirred solution of 33.14 g (100 mmol) of 2-aminospirobifluorene (preparation in accordance with *J. Am. Chem. Soc.* 1950, 72, 4253) in 250 ml of pyridine and 400 ml of toluene, and the mixture is subsequently stirred at room temperature for 16 h. The solvent is subsequently evaporated in vacuo. The residue is taken up in 300 ml of THF, and 4.00 g (100 mmol) of NaH (60% in oil) are added. After 1 h at 50° C., 26.8 g (100 mmol) of 2-chloro-4,6-diphenyl-1,3,5-triazine are added, and the mixture is heated under reflux for 48 h. The solvent is subsequently evaporated in vacuo, and the residue is purified by chromatography (heptane/ethyl acetate 30:1). The product is recrystallised three times from dioxane/toluene 1:1 and sublimed in vacuo ($10^{-5}$ mbar, 360° C.). The yield is 28.5 g (36 mmol), corresponding to 36% of theory. Tg (DSC) 156° C., Tm (DSC) 355° C., purity>99.9%.

Example 4

Biphenyl-3-ylbis-(4,6-diphenylpyrimidin-2-yl)amine (4)

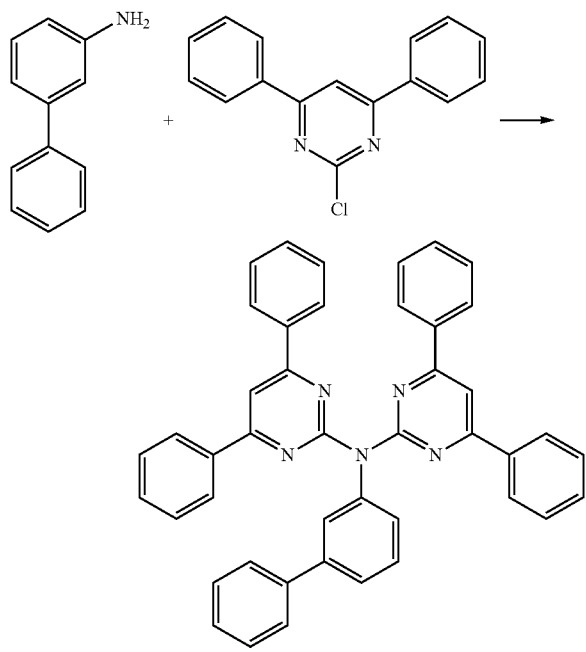

26.7 g (100 mmol) of 2-chloro-4,6-diphenylpyrimidine (BOC-Sciences) in 200 ml of toluene are added to a vigorously stirred solution of 16.9 g (100 mmol) of 2-aminobiphenyl (VWR-Chemicals) in 250 ml of pyridine and 400 ml of toluene, and the mixture is subsequently stirred at room temperature for 16 h. The solvent is subsequently evaporated in vacuo. The residue is taken up in 300 ml of THF, and 4.00 g (100 mmol) of NaH (60% in oil) are added. After 1 h at 50° C., 26.8 g (100 mmol) of 2-chloro-4,6-diphenylpyrimidine are added, and the mixture is heated under reflux for 48 h. The solvent is subsequently evaporated in vacuo, and the residue is purified by chromatography (heptane/ethyl acetate 30:1). The material is recrystallised five times from ethyl acetate and sublimed in vacuo ($10^{-5}$ mbar, 365° C.). The yield is 24.5 g (39 mmol), corresponding to 39% of theory. Tg (DSC) 125° C., Tm (DSC) 302° C., purity>99.95%.

Example 5

Production of OLEDs

OLEDs according to the invention and OLEDs in accordance with the prior art are produced by a general process in accordance with WO 2004/058911, which is adapted to the circumstances described here (layer-thickness variation, materials used).

The results for various OLEDs are presented in Device Examples 1 to 22 below (see Tables 1 and 2). Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as H1:SEB1 (95%: 5%) here means that material H1 is present in the layer in a proportion by volume of 95% and SEB1 is present in the layer in a proportion by volume of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in per cent) as a function of the luminous density, calculated from current/voltage/luminance characteristic lines (IUL characteristic lines), and the lifetime are determined. The lifetime is defined as the time after which the luminous density has dropped to a certain proportion from a certain initial luminous density $I_0$. The expression LD50 means that the said lifetime is the time at which the luminous density has dropped to $0.5 \cdot I_0$ (to 50%), i.e. from, for example, 6000 cd/m² to 3000 cd/m².

The compounds according to the invention can be employed, inter alia, as matrix materials (host materials) for fluorescent dopants. Compounds H3 according to the invention is used here. Compound H1 is used as comparison in accordance with the prior art. OLEDs comprising the blue-emitting dopant SEB1 are shown. The results for the OLEDs are summarised in Table 2. Examples 1 to 4 show OLEDs comprising materials in accordance with the prior art and serve as comparative examples. The fluorescent OLEDs according to the invention from Examples 7 to 10 exhibit the advantages on use of compounds of the formula (1), in particular higher efficiency and a longer lifetime.

Compounds of the formula (1) can also be used as electron-transport material in an electron-transport layer (Examples 11 to 16). The use of these compounds enables the operating voltage to be significantly reduced at the same time as higher efficiency and a longer lifetime.

Compounds of the formula (1) can also be employed in phosphorescent OLEDs. The matrix materials used here were H4-H6. The use of these materials exhibits significant advantages with respect to efficiency, operating voltage and operative lifetime (Examples 17 to 22 and as comparison Examples 5 and 6).

The use of the compounds according to the invention enables, compared with the prior art, improvements to be achieved in the processing and the material stability. The electrical performance is at least comparable or better than the reference.

TABLE 1

Structure of the OLEDs

| Ex. | HTL Thickness | IL Thickness | EBL Thickness | EML Thickness | ETL Thickness | EIL Thickness |
|---|---|---|---|---|---|---|
| 1 (comp.) | HTM1 140 nm | HIL1 5 nm | NPB 20 nm | H1:SEB1 (95%:5%) 20 nm | ETM1:LiQ (50:50) 30 nm | |
| 2 (comp.) | HTM1 140 nm | HIL1 5 nm | NPB 20 nm | H1:SEB1 (95%:5%) 20 nm | ETM1:LiQ (25:75) 30 nm | |
| 3 (comp.) | HTM1 140 nm | HIL1 5 nm | NPB 20 nm | H1:SEB1 (95%:5%) 20 nm | ETM1 30 nm | LiQ 3 nm |
| 4 (comp.) | HTM1 140 nm | HIL1 5 nm | NPB 20 nm | H1:SEB1 (95%:5%) 20 nm | Alq 30 nm | LiF 1 nm |
| 5 (comp.) | HTM1 20 nm | | NPB 20 nm | H2:TER1 (85%:15%) 30 nm | Alq 20 nm | LiF 1 nm |
| 6 (comp.) | HTM1 160 nm | | EBM1 20 nm | H2:TEG1 (90%:10%) 30 nm | ETM1:LiQ (50%:50%) 40 nm | |
| 7 | HTM1 140 nm | HIL1 5 nm | NPB 20 nm | H3:SEB1 (95%:5%) 20 nm | ETM1:LiQ (50:50) 30 nm | |
| 8 | HTM1 140 nm | HIL1 5 nm | NPB 20 nm | H3:SEB1 (95%:5%) 20 nm | ETM1:LiQ (25:75) 30 nm | |
| 9 | HTM1 140 nm | HIL1 5 nm | NPB 20 nm | H3:SEB1 (95%:5%) 20 nm | ETM1 30 nm | LiQ 3 nm |
| 10 | HTM1 140 nm | HIL1 5 nm | NPB 20 nm | H3:SEB1 (95%:5%) 20 nm | Alq 30 nm | LiF 1 nm |
| 11 | HTM1 140 nm | HIL1 5 nm | NPB 20 nm | H1:SEB1 (95%:5%) 20 nm | ETM2:LiQ (50:50) 30 nm | |
| 12 | HTM1 140 nm | HIL1 5 nm | NPB 20 nm | H1:SEB1 (95%:5%) 20 nm | ETM2:LiQ (25:75) 30 nm | |
| 13 | HTM1 140 nm | HIL1 5 nm | NPB 20 nm | H1:SEB1 (95%:5%) 20 nm | ETM2 30 nm | LiQ 3 nm |
| 14 | HTM1 140 nm | HIL1 5 nm | NPB 20 nm | H1:SEB1 (95%:5%) 20 nm | ETM3:LiQ (50:50) 30 nm | |
| 15 | HTM1 140 nm | HIL1 5 nm | NPB 20 nm | H1:SEB1 (95%:5%) 20 nm | ETM3:LiQ (25:75) 30 nm | |
| 16 | HTM1 140 nm | HIL1 5 nm | NPB 20 nm | H1:SEB1 (95%:5%) 20 nm | ETM3 30 nm | LiQ 3 nm |
| 17 | HTM1 20 nm | | NPB 20 nm | H4:TER1 (85%:15%) 30 nm | Alq 20 nm | LiF 1 nm |
| 18 | HTM1 160 nm | | EBM1 20 nm | H4:TEG1 (90%:10%) 30 nm | ETM1:LiQ (50%:50%) 40 nm | |
| 19 | HTM1 20 nm | | NPB 20 nm | H5:TER1 (85%:15%) 30 nm | Alq 20 nm | LiF 1 nm |

TABLE 1-continued

| | | Structure of the OLEDs | | | | |
|---|---|---|---|---|---|---|
| Ex. | HTL Thickness | IL Thickness | EBL Thickness | EML Thickness | ETL Thickness | EIL Thickness |
| 20 | HTM1 160 nm | | EBM1 20 nm | H5:TEG1 (90%:10%) 30 nm | ETM1:LiQ (50%:50%) 40 nm | |
| 21 | HTM1 20 nm | | NPB 20 nm | H6:TER1 (85%:15%) 30 nm | Alq 20 nm | LiF 1 nm |
| 22 | HTM1 160 nm | | EBM1 20 nm | H6:TEG1 (90%:10%) 30 nm | ETM1:LiQ (50%:50%) 40 nm | |

TABLE 2

Results for the OLEDs

| Ex. | Voltage [V] for 1000 cd/m$^2$ | Efficiency [cd/A] at 1000 cd/m$^2$ | Efficiency [lm/W] at 1000 cd/m$^2$ | CIE x/y at 1000 cd/m$^2$ | | LT50 I = 6000 cd/m$^2$ |
|---|---|---|---|---|---|---|
| 1 (comp.) | 4.2 | 9.6 | 7.3 | 0.142 | 0.145 | 180 |
| 2 (comp.) | 5.1 | 7.3 | 4.5 | 0.142 | 0.147 | 490 |
| 3 (comp.) | 3.6 | 7.9 | 6.8 | 0.142 | 0.150 | 80 |
| 4 (comp.) | 5.7 | 5.4 | 3.0 | 0.149 | 0.169 | 240 |
| 5 (comp.) | 4.7 | 7.1 | 4.7 | 0.69 | 0.31 | 420 |
| 6 (comp.) | 4.6 | 54 | 37 | 0.37 | 0.60 | 400* |
| 7 | 3.9 | 9.9 | 8.0 | 0.142 | 0.145 | 250 |
| 8 | 4.2 | 7.4 | 5.6 | 0.142 | 0.146 | 610 |
| 9 | 3.3 | 7.9 | 7.5 | 0.143 | 0.147 | 160 |
| 10 | 5.1 | 5.5 | 3.4 | 0.148 | 0.163 | 280 |
| 11 | 4.0 | 8.1 | 6.4 | 0.143 | 0.141 | 340 |
| 12 | 4.0 | 7.5 | 5.9 | 0.143 | 0.142 | 660 |
| 13 | 3.2 | 6.3 | 6.1 | 0.143 | 0.147 | 170 |
| 14 | 3.6 | 9.3 | 8.1 | 0.143 | 0.141 | 540 |
| 15 | 3.5 | 8.0 | 7.2 | 0.143 | 0.144 | 860 |
| 16 | 3.2 | 8.3 | 8.1 | 0.143 | 0.146 | 370 |
| 17 | 4.3 | 8.2 | 6.0 | 0.69 | 0.31 | 540 |
| 18 | 4.2 | 56 | 42 | 0.37 | 0.60 | 490* |
| 19 | 4.7 | 7.2 | 4.8 | 0.69 | 0.31 | 770 |
| 20 | 4.6 | 54 | 37 | 0.37 | 0.60 | 680* |
| 21 | 3.8 | 7.8 | 6.5 | 0.69 | 0.31 | 490 |
| 22 | 3.6 | 58 | 51 | 0.37 | 0.60 | 450* |

*For these components, the lifetime LT80 from 4000 cd/m$^2$ is determined.

TABLE 3

Structural formulae of the materials used

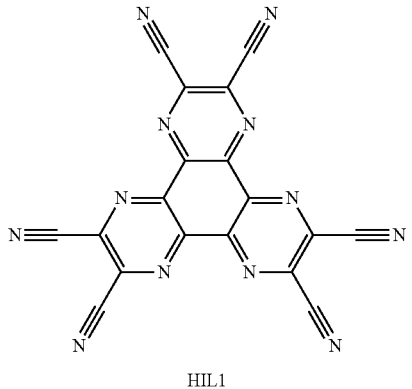 [SMILES: N#Cc1nc2c3nc(C#N)c(C#N)nc3c3nc(C#N)c(C#N)nc3c2nc1C#N]

HIL1

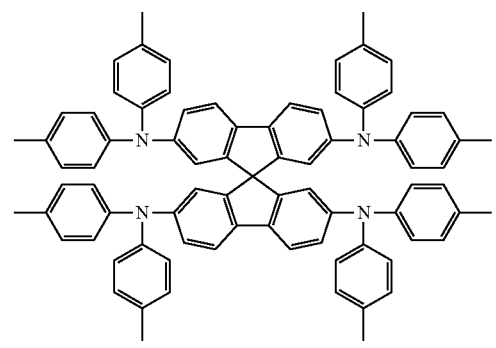

HTM1

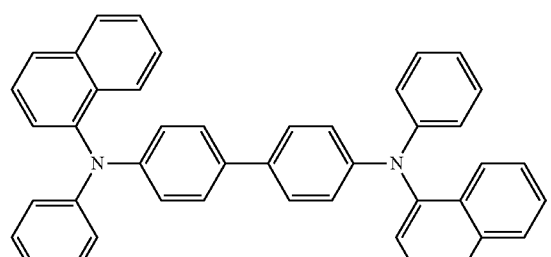

NPB

TABLE 3-continued
Structural formulae of the materials used
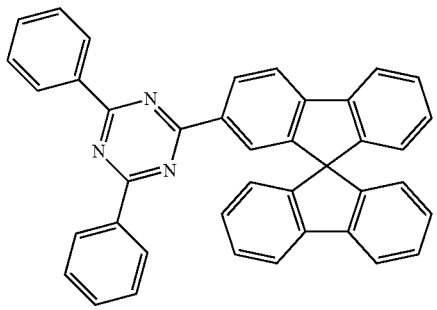
ETM1/H2
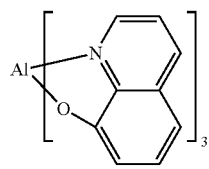
Alq3
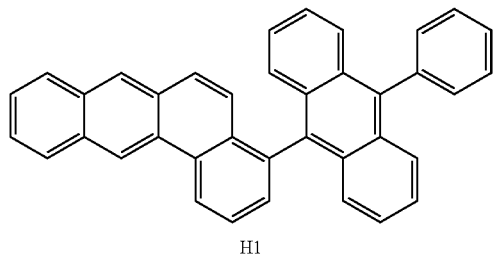
H1
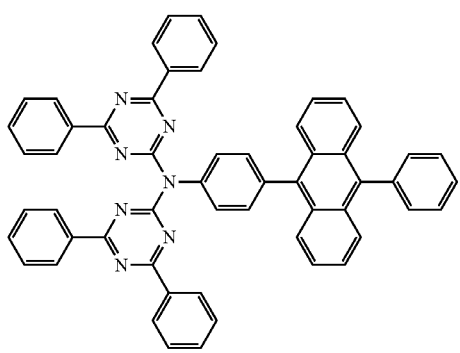
H3
TABLE 3-continued
Structural formulae of the materials used
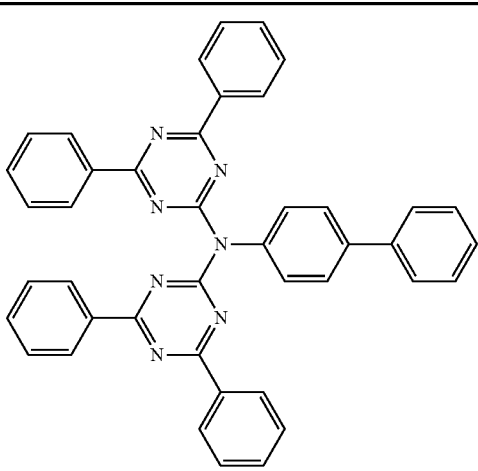
H4
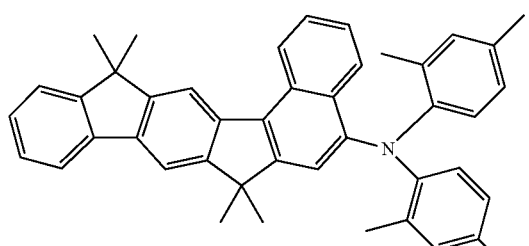
SEB1
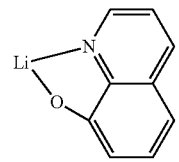
LiQ
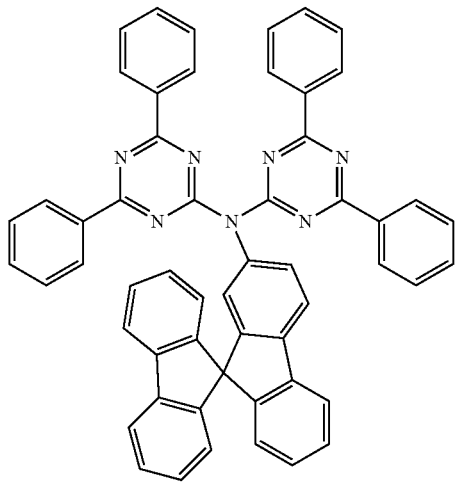
ETM2/H5

TABLE 3-continued

Structural formulae of the materials used

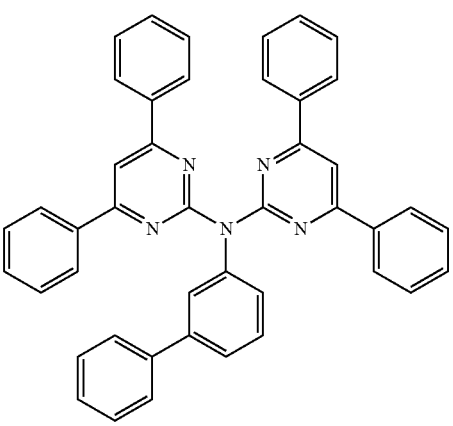

ETM3/H6

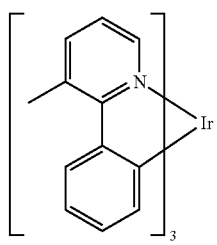

TEG1

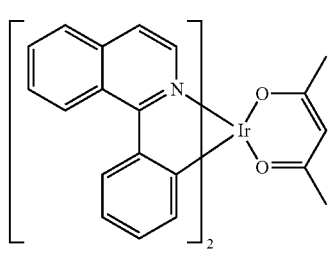

TER1

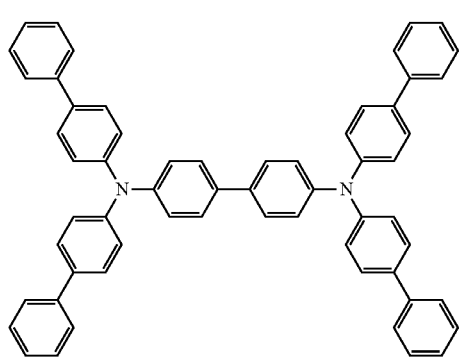

EBM1

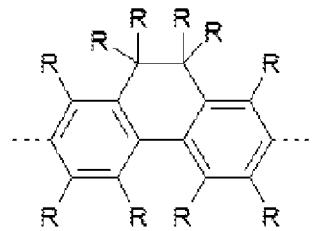

The invention claimed is:

1. A compound of the formula (1),

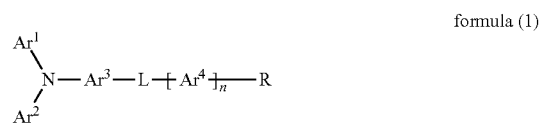
formula (1)

where the following applies to the symbols and indices used:

$Ar^1$ and $Ar^2$ are identically or differently on each occurrence, a group of the following formula(3)-formula(8) or formula(10)-formula(12)

formula (3)

formula (4)

formula (5)

formula (6)

formula (7)

formula (8)

formula (10)

-continued

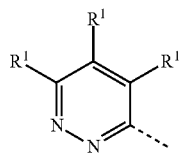

formula (11)

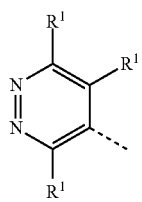

formula (12)

where the dashed bond indicates the bond to the nitrogen;
Ar³ and Ar⁴ are on each occurrence, identically or differently, an aromatic or heteroaromatic ring system having 5 to 30 aromatic ring atoms, which is optionally substituted by one or more radicals R; with the proviso that Ar³ and Ar⁴ contain no amino groups and no carbazole groups bonded via N;

L is a single bond or a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which is optionally substituted by in each case one or more radicals R, where one or more CH₂ groups, is optionally replaced by Si(R)₂, Ge(R)₂, Sn(R)₂, C=O, C=S, C=Se, C=NR, P(=O)R, S=O, SO₂, —O—, —S— or —CONR— and where one or more H atoms is optionally replaced by D, F, Cl, Br, I, CN or NO₂, or a divalent aromatic or heteroaromatic ring system having 5 to 30 aromatic ring atoms, which is optionally substituted by one or more radicals R and which contains no amino groups and no carbazole groups bonded via N, or Si(R)₂, Ge(R)₂, O, S, C(=O), S(=O), SO₂, PR, P(=O)(R), P(=S)(R) or a combination of two, three, four or five of these systems;

R is selected on each occurrence, identically or differently, from the group consisting of H, D, F, Cl, Br, I, CN, NO₂, C(=O)Ar, C(=O)R², P(=O)(Ar)₂, B(R²)₂, B(OR²)₂, Si(R²)₃, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R², where one or more non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by D, F, Cl, Br, I, CN or NO₂, an aromatic or heteroaromatic ring system having 5 to 60 aromatic ring atoms, which may in each case be substituted by one or more radicals R² and which contains no amino groups and no carbazole groups bonded via N, an aryloxy or heteroaryloxy group having 5 to 60 aromatic ring atoms, which is optionally substituted by one or more radicals R², or an aralkyl or heteroaralkyl group having 5 to 60 aromatic ring atoms, which may in each case be substituted by one or more radicals R², where two or more adjacent substituents R may optionally form a mono- or polycyclic, aliphatic, aromatic or heteroaromatic ring system, which is optionally substituted by one or more radicals R²;

R¹ is selected on each occurrence, identically or differently, from the group consisting of D, F, Br, I, CN, NO₂, C(=O)Ar, C(=O)R², P(=O)(Ar)₂, B(R²)₂, B(OR²)₂, Si(R²)₃, a straight-chain alkyl or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R², where one or more non-adjacent CH₂ groups is optionally replaced by R²C=CR², C≡C, Si(R²)₂, Ge(R²)₂, Sn(R²)₂, C=O, C=S, C=Se, C=NR², P(=O)(R²), SO, SO₂, NR², O, S or CONR² and where one or more H atoms is optionally replaced by D, F, Cl, Br, I, CN or NO₂, an aromatic or heteroaromatic ring system having 5 to 60 aromatic ring atoms, which may in each case be substituted by one or more radicals R² and which contains no amino groups and no carbazole groups bonded via N, an aryloxy or heteroaryloxy group having 5 to 60 aromatic ring atoms, which is optionally substituted by one or more radicals R², or an aralkyl or heteroaralkyl group having 5 to 60 aromatic ring atoms, which may in each case be substituted by one or more radicals R², where two or more adjacent substituents R may optionally form a mono- or polycyclic, aliphatic, aromatic or heteroaromatic ring system, which is optionally substituted by one or more radicals R²;

with the proviso that R¹ contains no condensed aryl groups;

R² is selected on each occurrence, identically or differently, from the group consisting of H, D, F, Cl, Br, I, CN, NO₂, C(=O)Ar, C(=O)R³, P(=O)(Ar)₂, B(R³)₂, B(OR³)₂, Si(R³)₃, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R³, where one or more non-adjacent CH₂ groups is optionally replaced by R³C=CR³, C≡C, Si(R³)₂, Ge(R³)₂, Sn(R³)₂, C=O, C=S, C=Se, C=NR³, P(=O)(R³), SO, SO₂, NR³, O, S or CONR³ and where one or more H atoms is optionally replaced by D, F, Cl, Br, I, CN or NO₂, an aromatic or heteroaromatic ring system having 5 to 60 aromatic ring atoms, which may in each case be substituted by one or more radicals R³ and which contains no amino groups and no carbazole groups bonded via N, an aryloxy or heteroaryloxy group having 5 to 60 aromatic ring atoms, which is optionally substituted by one or more radicals R³, or an aralkyl or heteroaralkyl group having 5 to 60 aromatic ring atoms, which is optionally substituted by one or more radicals R³, where two or more adjacent substituents R² may optionally form a mono- or polycyclic, aliphatic, aromatic or heteroaromatic ring system, which is optionally substituted by one or more radicals R³;

Ar is on each occurrence, identically or differently, an aromatic or heteroaromatic ring system having 5-30 aromatic ring atoms, which is optionally substituted by one or more non-aro-matic radicals R³; two radicals Ar which are bonded to the same P atom may also be bridged to one another here by a single bond or a bridge selected from N(R³), C(R³)₂, O or S;

R³ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents R³ may form a mono- or polycyclic, aliphatic, aromatic or heteroaromatic ring system with one another;

n is 0 or 1;

wherein at least one radical R¹ stands for an aromatic or heteroaromatic ring system and/or in that Ar³ represents an aromatic or heteroaromatic ring system having at least two aryl or heteroaryl groups and/or in that n=1 and thus one group Ar⁴ is present;

the following compounds are excluded from the invention:

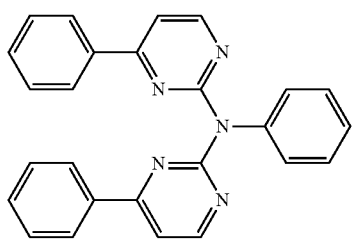

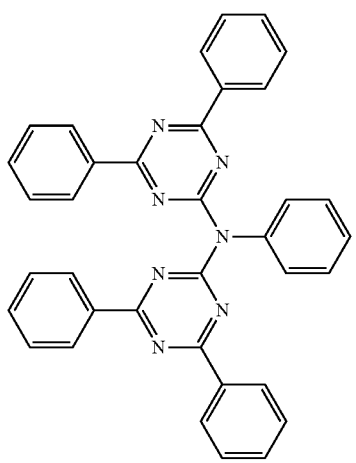

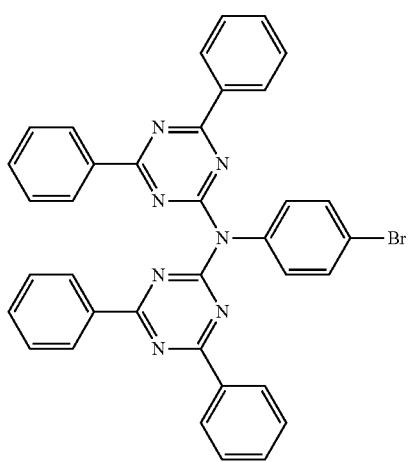

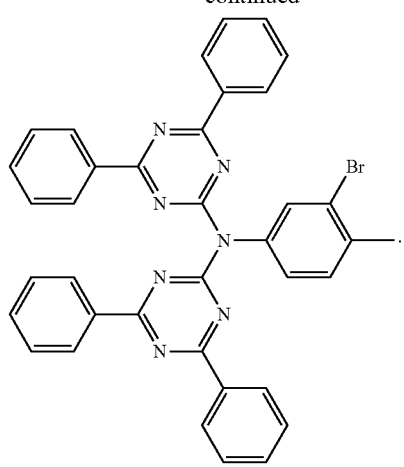

2. The compound according to claim 1, wherein the group —NAr¹Ar² is selected from the formulae (13) to (17):

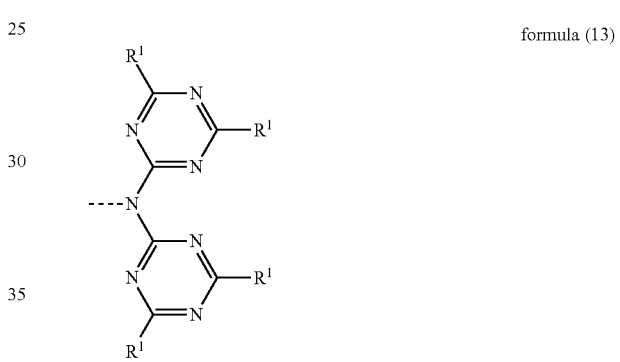

formula (13)

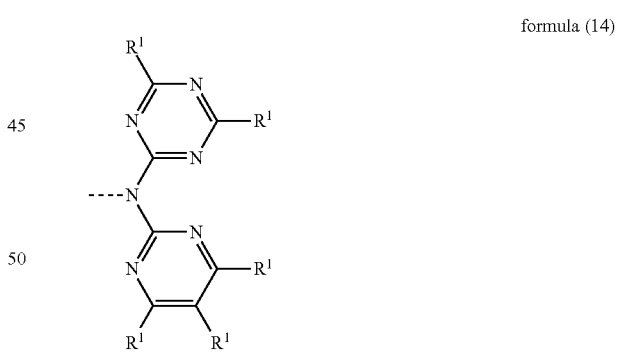

formula (14)

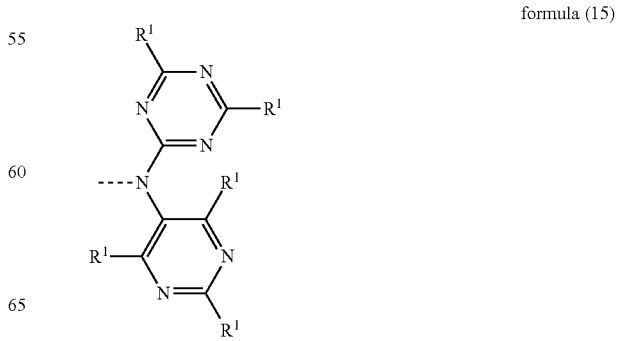

formula (15)

-continued formula (16)

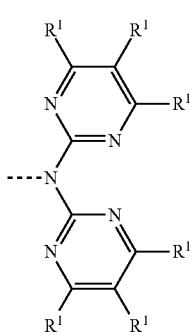

formula (17)

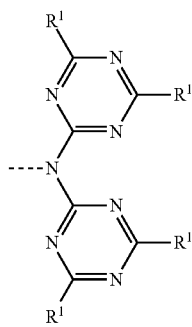

where the symbols used have the meanings given in claim 1 and the dashed bond indicates the bond from this group to Ar³.

3. The compound according to claim 1, wherein L is a single bond, a divalent straight-chain alkylene or alkylidene group having 1 to 10 C atoms, or a branched or cyclic alkylene or alkylidene group having 3 to 10 C atoms, which is optionally substituted by in each case one or more radicals R, where one or more CH₂ groups, is optionally replaced by Si(R)₂, C=O, P(=O)R, S=O, SO₂, —O—, —S— or —CONR— and where one or more H atoms is optionally replaced by D or F, or a divalent aromatic or heteroaromatic ring system having 5 to 24 aromatic ring atoms, which may also be substituted by one or more radicals R, or Si(R)₂, C(=O), S(=O), SO₂, P(=O)R, O or S.

4. The compound according to claim 1, wherein L is a single bond, a divalent straight-chain alkylene or alkylidene group having 1 to 5 C atoms, or a branched or cyclic alkylene or alkylidene group having 3 to 6 C atoms, which is optionally substituted by in each case one or more radicals R, where one or more CH₂ groups, which are not bonded directly to N and are not adjacent, is optionally replaced by Si(R)₂, C=O, P(=O)R, S=O, SO₂, —O—, —S— or —CONR— and where one or more H atoms is optionally replaced by D or F, or a divalent aromatic or heteroaromatic ring system having 5 to 24 aromatic ring atoms, which may also be substituted by one or more radicals R, or Si(R)₂, C(=O), S(=O), SO₂, P(=O)R, O or S.

5. The compound according to claim 4, wherein —NAr¹Ar² is selected from the groups of the above-mentioned formulae (13) to (17)

formula (13)

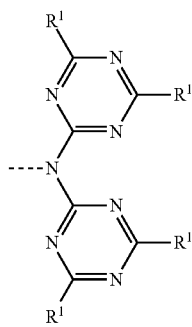

formula (14)

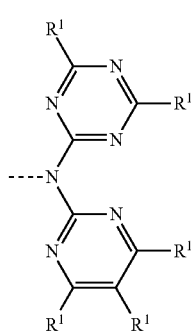

formula (15)

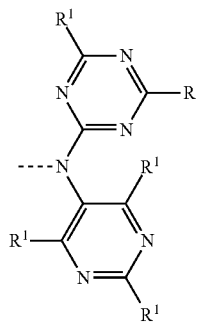

formula (16)

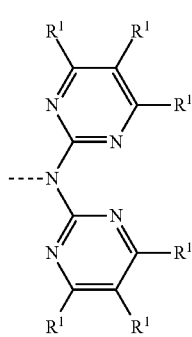

formula (17)

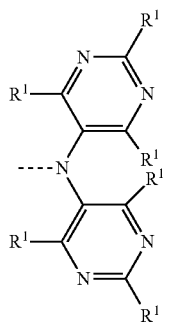

where the dashed bond indicates the bond from this group to $Ar^3$;

L is a single bond, a divalent aromatic or heteroaromatic ring system having 6 to 24 aromatic ring atoms, which is optionally substituted by one or more radicals R, or $Si(R)_2$ or $C(=O)$; L here, if L stands for an aromatic or heteroaromatic ring system;

$Ar^3$ and $Ar^4$ is selected, identically or differently on each occurrence, from structures of the above-mentioned formulae (18) to (116)

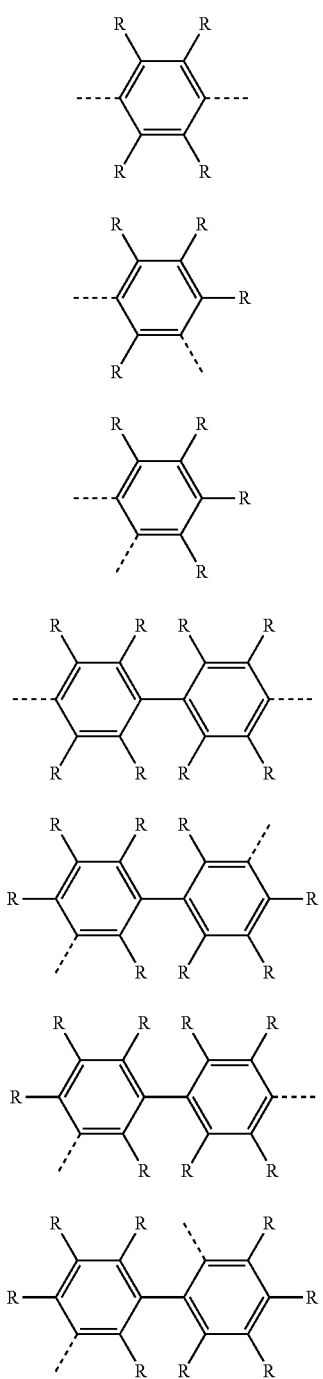

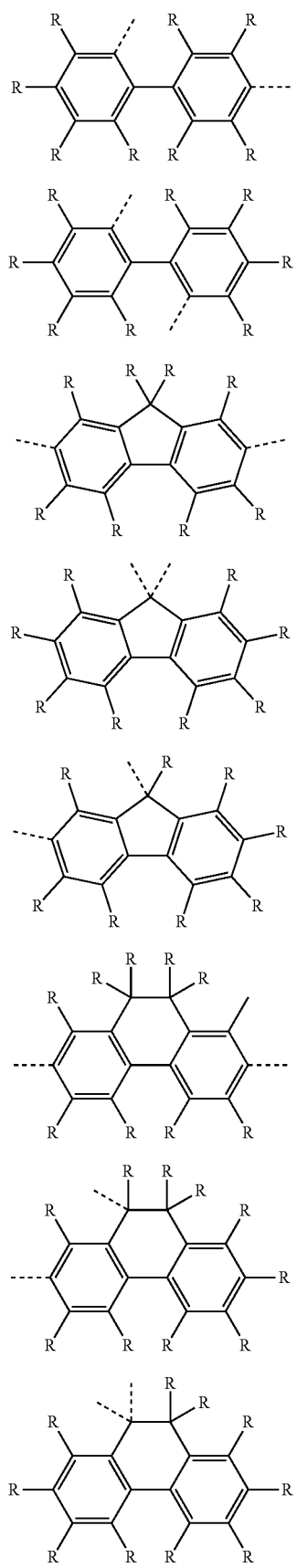

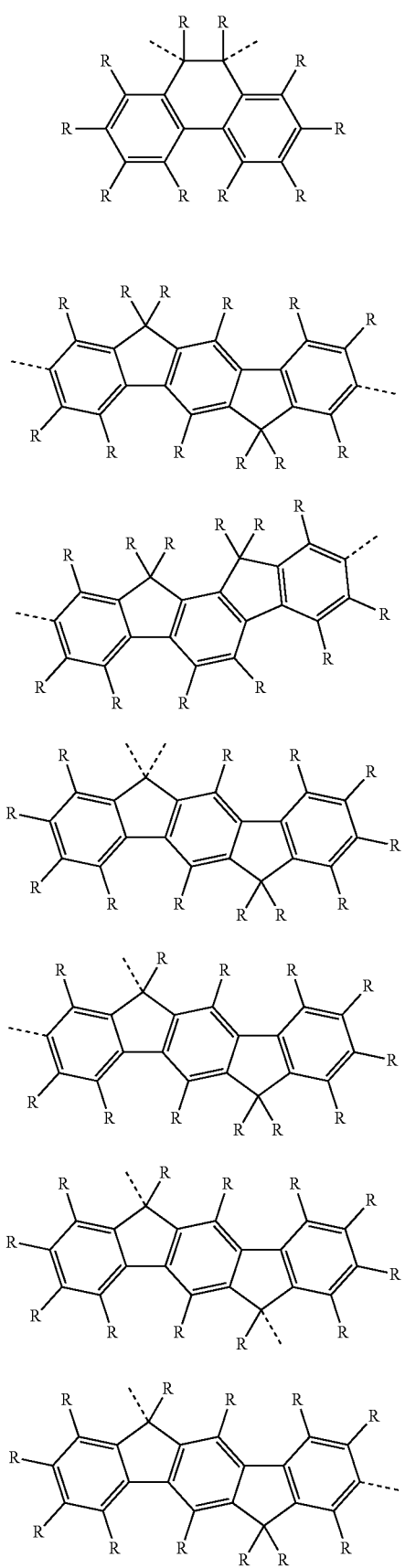
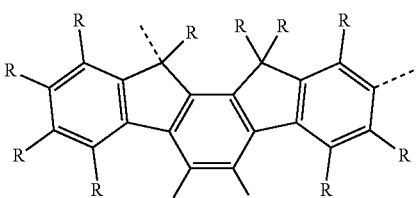

formula (46)
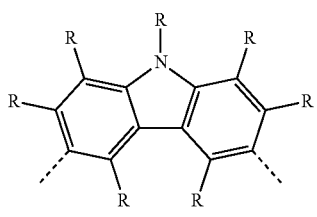
formula (47)
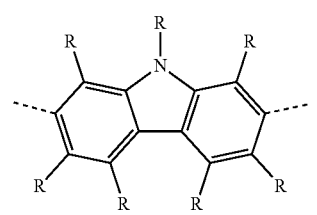
formula (48)
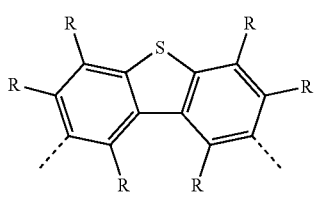
formula (49)
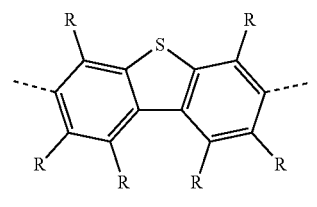
formula (50)
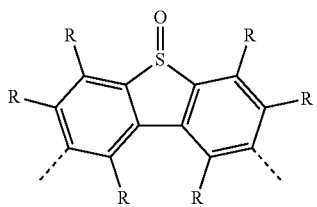
formula (51)
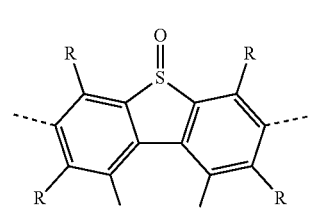
formula (52)
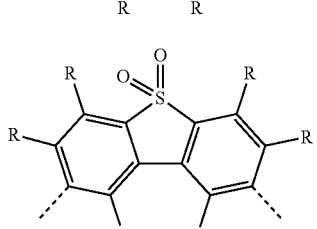
formula (53)
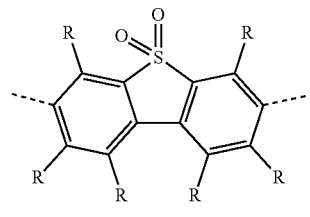
formula (54)
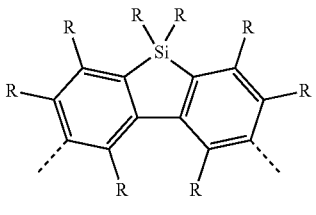
formula (55)
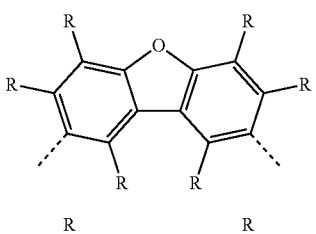
formula (56)
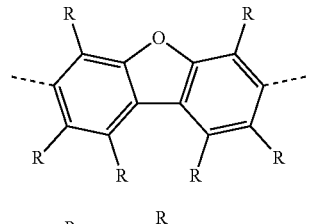
formula (57)
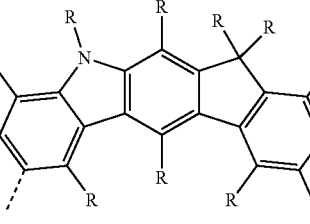
formula (58)
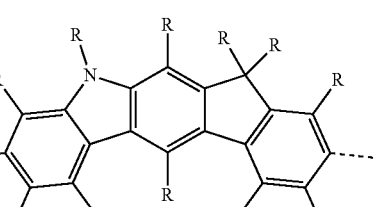
formula (59)
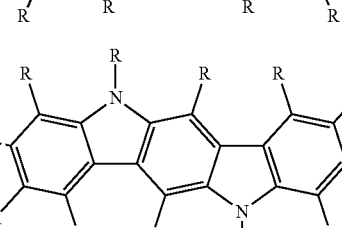

formula (60)
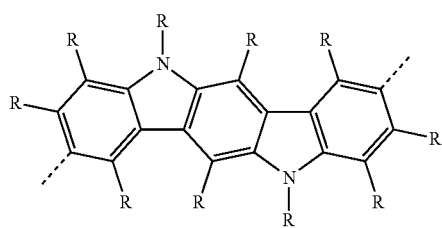
formula (61)
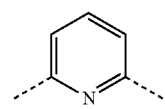
formula (62)
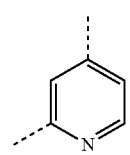
formula (63)
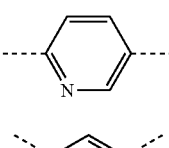
formula (64)
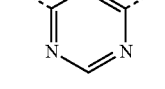
formula (65)
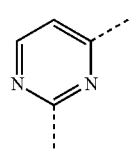
formula (66)
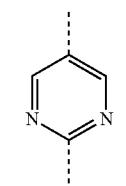
formula (67)
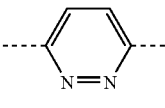
formula (68)
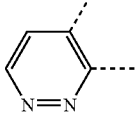
formula (69)
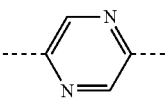
formula (70)
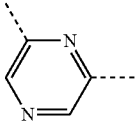
formula (71)
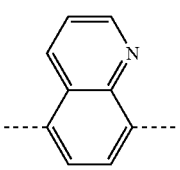
formula (72)
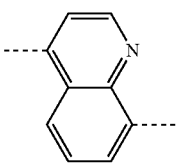
formula (73)
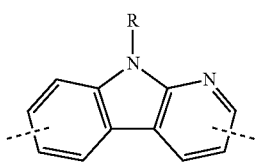
formula (74)
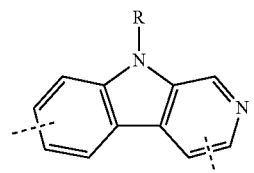
formula (75)
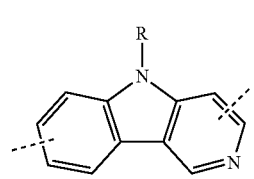
formula (76)
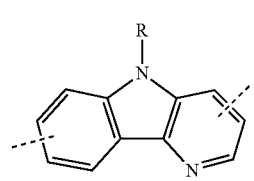
formula (77)
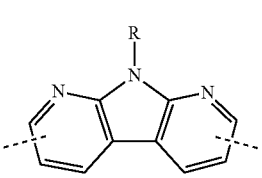
formula (78)
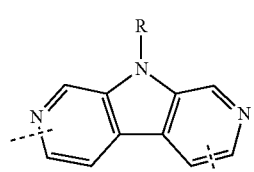
formula (79)
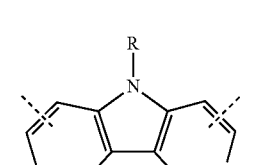

formula (80)
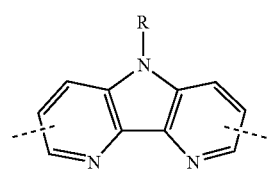
formula (81)
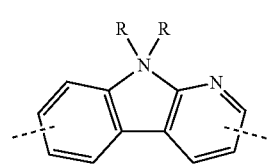
formula (82)
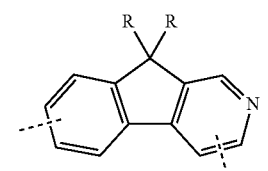
formula (83)
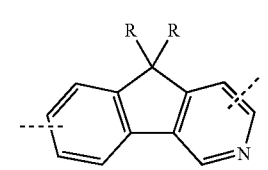
formula (84)
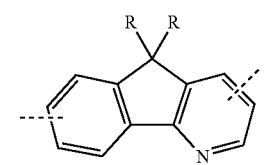
formula (85)
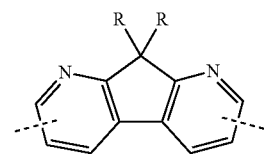
formula (86)
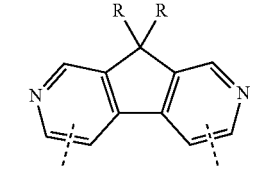
formula (87)
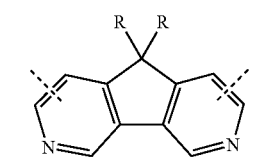
formula (88)
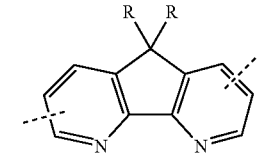
formula (89)
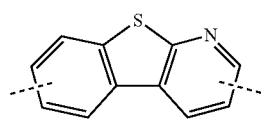
formula (90)
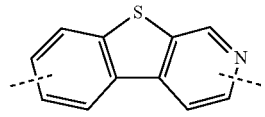
formula (91)
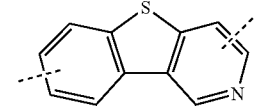
formula (92)
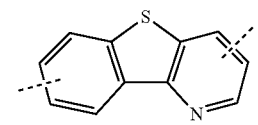
formula (93)
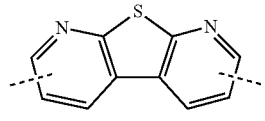
formula (94)
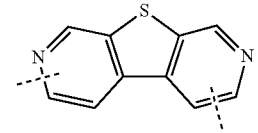
formula (95)
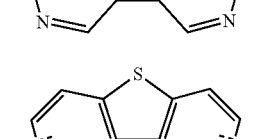
formula (96)
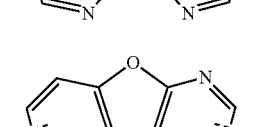
formula (97)
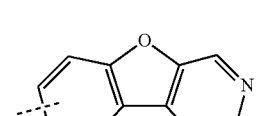
formula (98)
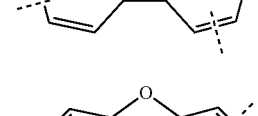
formula (99)
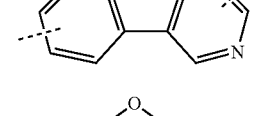
formula (100)
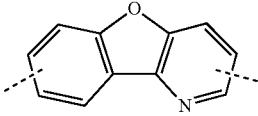

-continued formula (101)
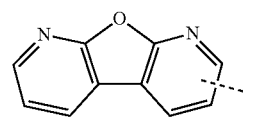

formula (102)
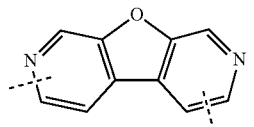

formula (103)
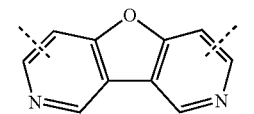

formula (104)
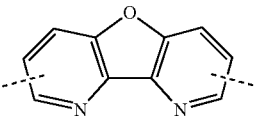

formula (105)
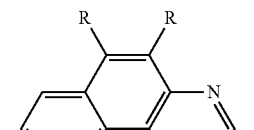

formula (106)
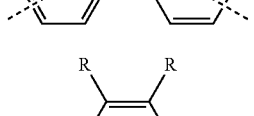

formula (107)
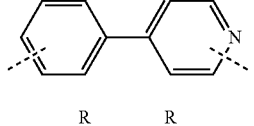

formula (108)
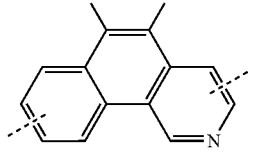

formula (109)
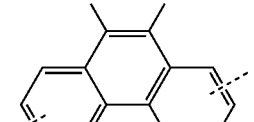

formula (110)
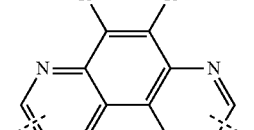

-continued formula (111)
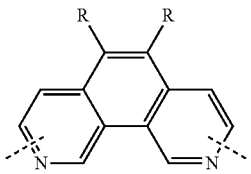

formula (112)
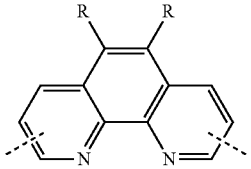

formula (113)
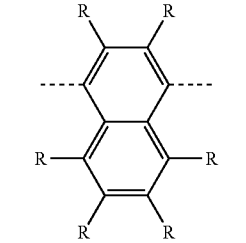

formula (114)
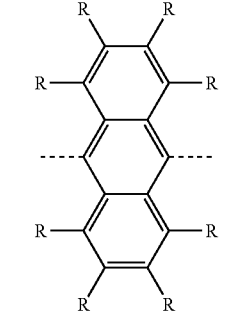

formula (115)
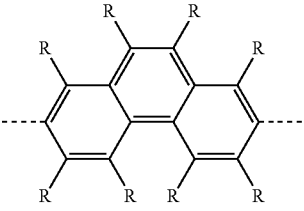

formula (116)
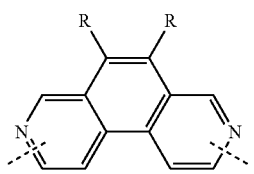

R is selected, identically or differently on each occurrence, from the group consisting of H, D, F, CN, a straight-chain alkyl group having 1 to 10 C atoms or a branched or cyclic alkyl group having 3 to 10 C atoms, each of which is optionally substituted by one or more radicals $R^2$, where one or more H atoms is optionally replaced by D or F, or an aromatic or heteroaromatic ring system having 5 to 18 aromatic ring atoms, which may in each case be substituted by one or more radicals $R^2$;

R[1] identically or differently on each occurrence, is selected from the group consisting of D, phenyl, ortho-, meta- or para-biphenyl, ortho-, meta-, para- or branched terphenyl and quaterphenyl; and R[2] identically or differently on each occurrence, is selected from the group consisting of H, D, F, CN, a straight-chain alkyl group having 1 to 5 C atoms or a branched or cyclic alkyl group having 3 to 5 C atoms, or an aromatic or heteroaromatic ring system having 5 to 18 aromatic ring atoms.

6. The compound according to claim 5, wherein L is selected from the formulae (18) to (116).

7. The compound according to claim 1, wherein Ar[3], Ar[4] and L, if it stands for an aromatic or heteroaromatic ring system, are selected, identically or differently on each occurrence, from structures of the following formulae (18) to (116),

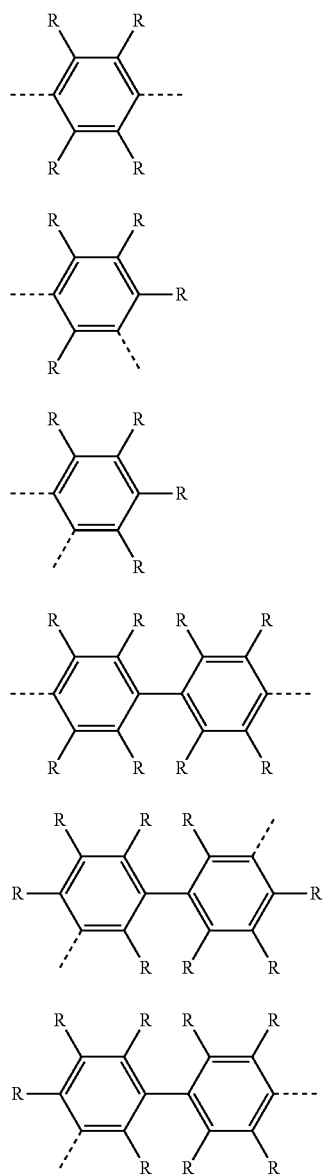

formula (18)

formula (19)

formula (20)

formula (21)

formula (22)

formula (23)

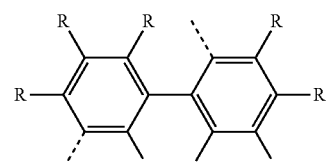

formula (24)

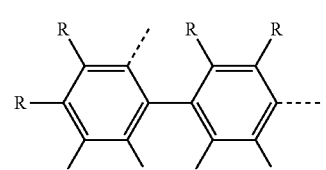

formula (25)

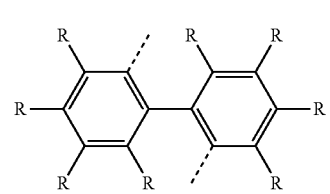

formula (26)

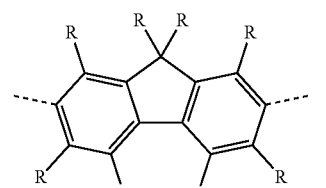

formula (27)

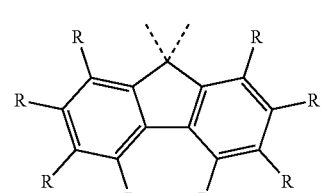

formula (28)

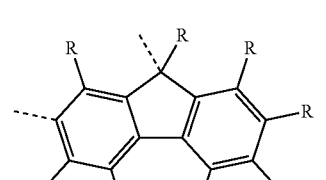

formula (29)

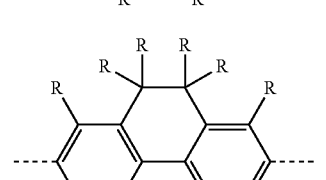

formula (30)

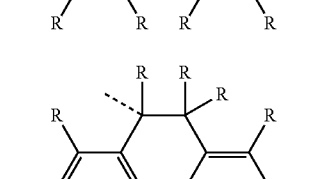

formula (31)

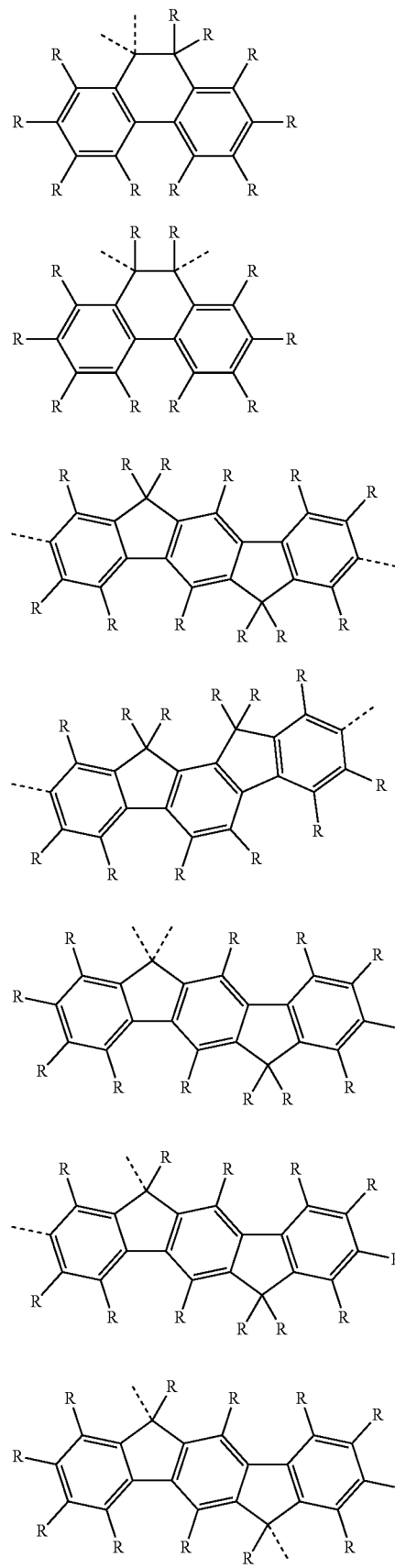
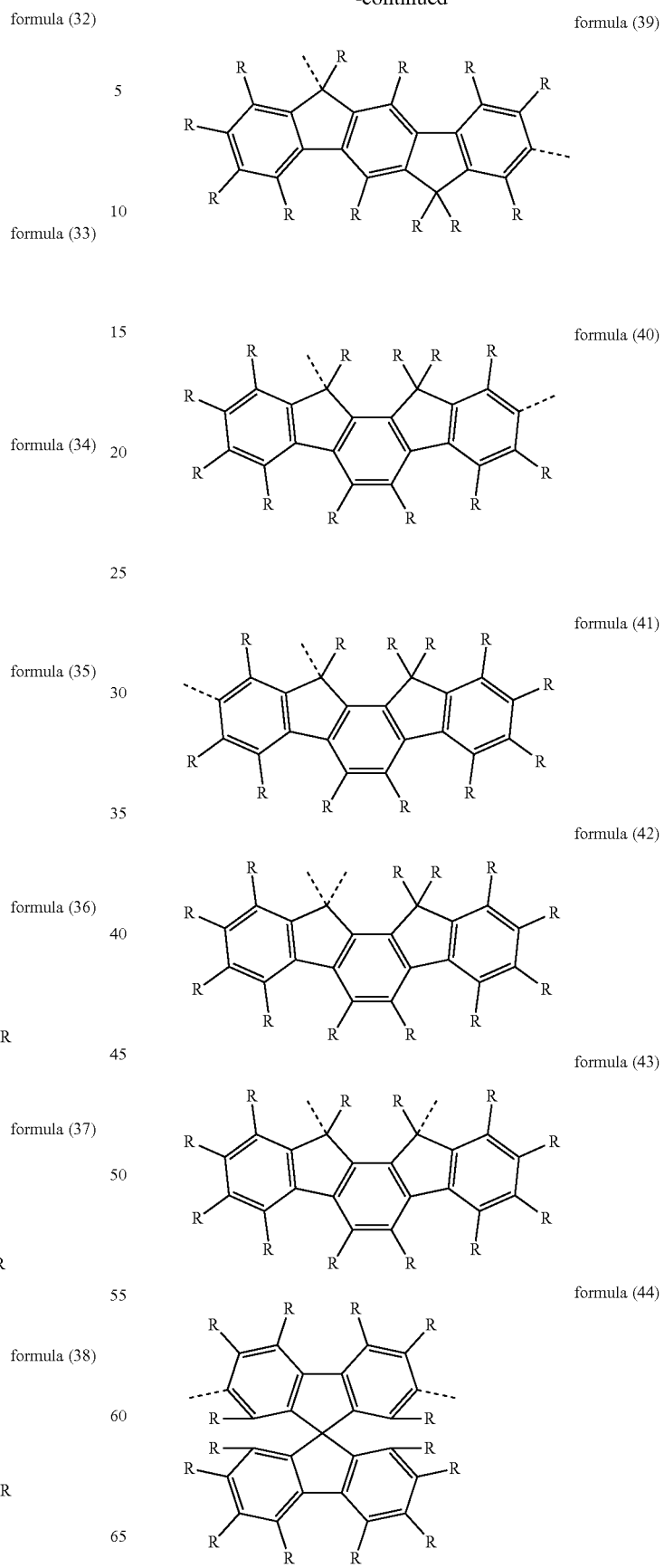

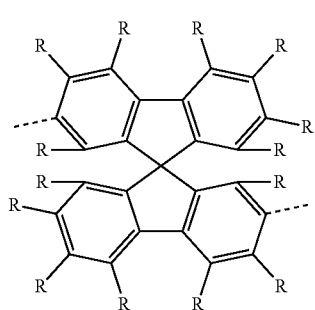
formula (45)
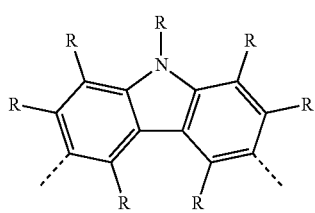
formula (46)
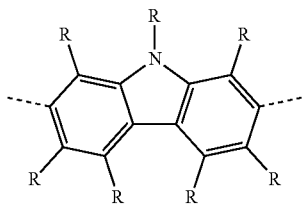
formula (47)
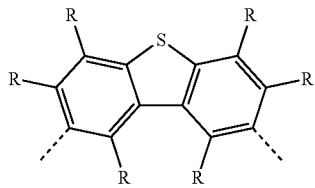
formula (48)
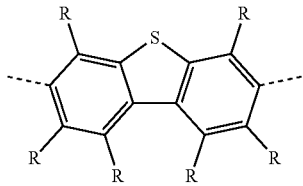
formula (49)
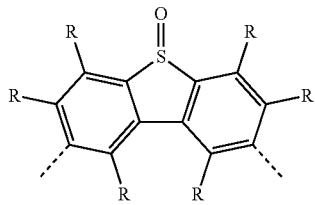
formula (50)
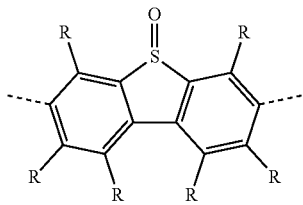
formula (51)
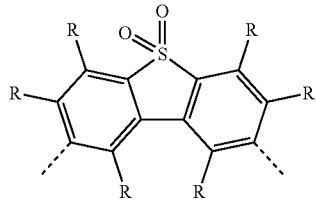
formula (52)
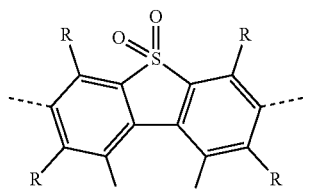
formula (53)
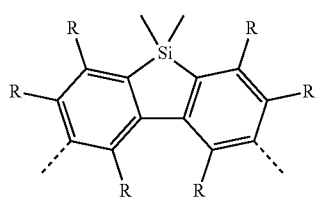
formula (54)
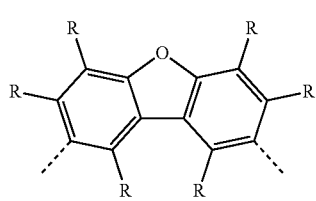
formula (55)
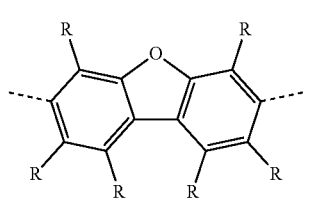
formula (56)
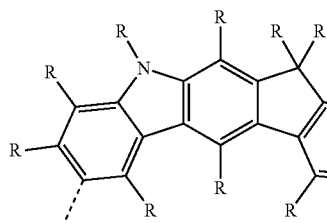
formula (57)
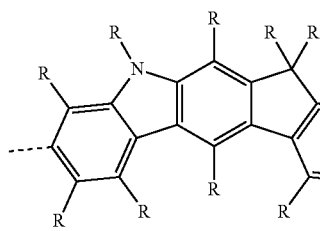
formula (58)

formula (59)
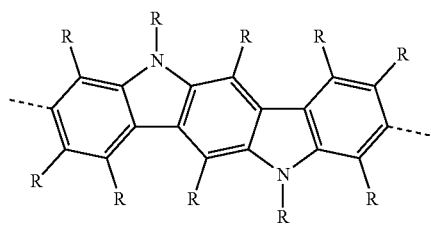
formula (60)
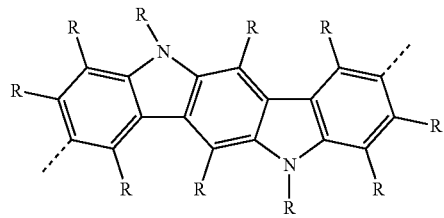
formula (61)
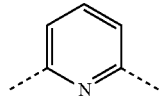
formula (62)
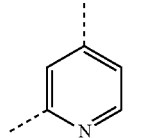
formula (63)
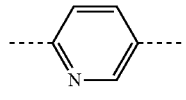
formula (64)
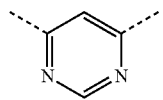
formula (65)
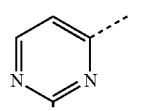
formula (66)
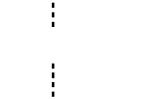
formula (67)
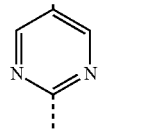
formula (68)
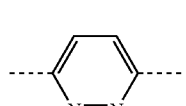
formula (69)
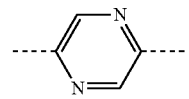
formula (70)
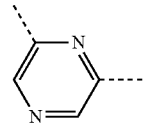
formula (71)
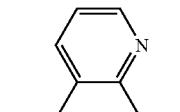
formula (72)
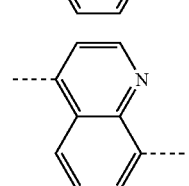
formula (73)
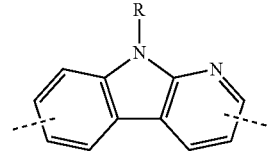
formula (74)
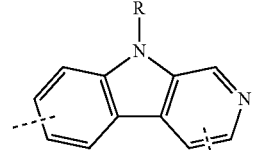
formula (75)
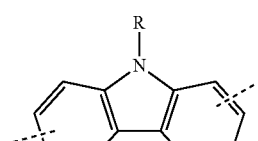
formula (76)
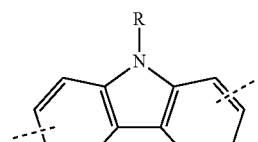
formula (77)
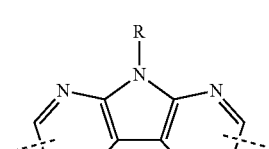
formula (78)
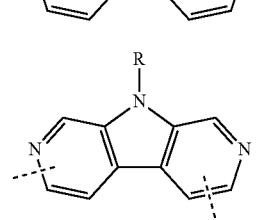

-continued
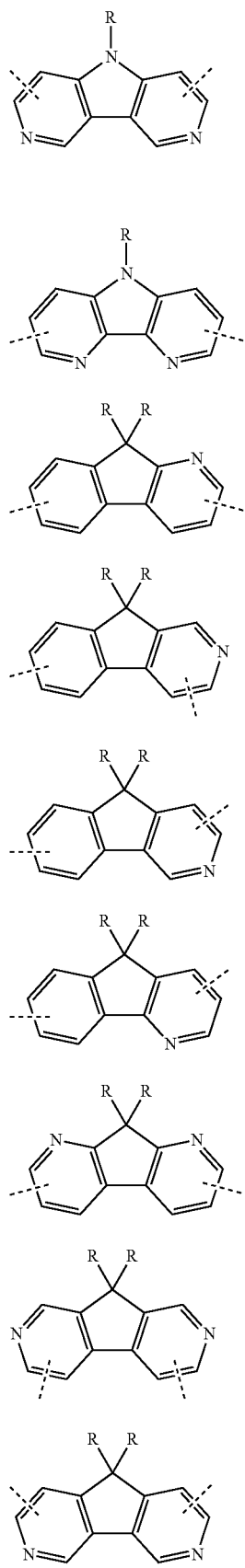
formula (79)
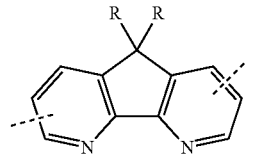
formula (80)
formula (81)
formula (82)
formula (83)
formula (84)
formula (85)
formula (86)
formula (87)
-continued
formula (88)
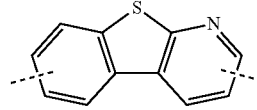
formula (89)
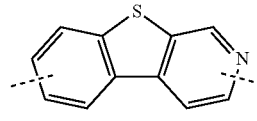
formula (90)
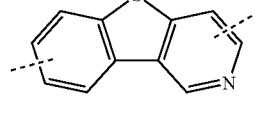
formula (91)
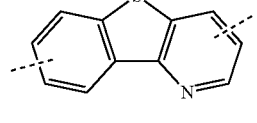
formula (92)
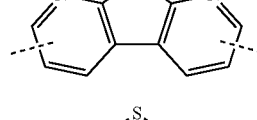
formula (93)
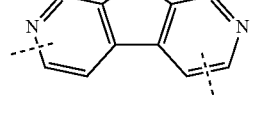
formula (94)
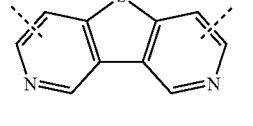
formula (95)
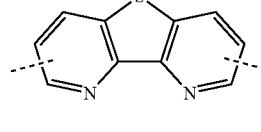
formula (96)
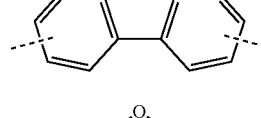
formula (97)
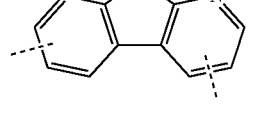
formula (98)
formula (99)

-continued formula (100)

formula (101)

formula (102)

formula (103)

formula (104)

formula (105)

formula (106)

formula (107)

formula (108)

formula (109)

-continued formula (110)

formula (111)

formula (112)

formula (113)

formula (114)

formula (115)

formula (116)

where symbols used have the meanings given in claim 1 and the dashed bonds indicate the positions at which the groups are bonded to the adjacent groups;

or wherein the index n=1 and L has a structure of the following formula (117):

   formula(117)

where:
Y is, identically or differently on each occurrence, $CR_2$, $SiR_2$, $GeR_2$, S or O;
p is 0, 1, 2, 3, 4, 5 or 6;
q is 0, 1, 2, 3 or 4;
p+q>0;
with the proviso that a plurality of heteroatoms are not bonded directly to one another.

8. The compound according to claim 7, wherein
p is 0, 1 or 2; and
q is 0, 1 or 2.

9. The compound according to claim 1, wherein $R^1$ is selected, identically or differently on each occurrence, from the group consisting of D or an aromatic or heteroaromatic ring system having 6 to 18 aromatic ring atoms which contains no condensed aryl groups, where the aromatic or heteroaromatic ring system is selected from the group consisting of phenyl, ortho-, meta- or para-biphenyl, ortho-, meta-, para- or branched terphenyl and quaterphenyl.

10. The compound according to claim 1,
wherein
L is a single bond, a divalent straight-chain alkylene or alkylidene group having 1 to 10 C atoms or a branched or cyclic alkylene or alkylidene group having 3 to 10 C atoms, which is optionally substituted by in each case one or more radicals R, where one or more $CH_2$ groups, which are not bonded directly to N and are not adjacent, is optionally replaced by $Si(R)_2$, C=O, P(=O)R, S=O, $SO_2$, —O—, —S— or —CONR— and where one or more H atoms is optionally replaced by D or F, or a divalent aromatic or heteroaromatic ring system having 5 to 24 aromatic ring atoms, which may also be substituted by one or more radicals R, or $Si(R)_2$, C(=O), S(=O), $SO_2$, P(=O)R, O or S;
R is selected, identically or differently on each occurrence, from the group consisting of H, D, F, Cl, Br, CN, C(=O)Ar, a straight-chain alkyl or alkoxy group having 1 to 10 C atoms or a branched or cyclic alkyl or alkoxy group having 3 to 10 C atoms, each of which is optionally substituted by one or more radicals $R^2$, where one or more non-adjacent $CH_2$ groups is optionally replaced by O and where one or more H atoms is optionally replaced by D or F, an aromatic or heteroaromatic ring system having 5 to 30 aromatic ring atoms, which may in each case be substituted by one or more radicals $R^2$, or an aryloxy or heteroaryloxy group having 5 to 30 aromatic ring atoms, which is optionally substituted by one or more radicals $R^2$;
$R^1$ is selected, identically or differently on each occurrence, from the group consisting of D or an aromatic or heteroaromatic ring system having 6 to 18 aromatic ring atoms which contains no condensed aryl groups;
$R^2$ is selected, identically or differently on each occurrence, from the group consisting of H, D, F, CN, a straight-chain alkyl group having 1 to 10 C atoms or a branched or cyclic alkyl group having 3 to 10 C atoms, where one or more H atoms is optionally replaced by D or F, or an aromatic or heteroaromatic ring system having 5 to 30 aromatic ring atoms, which may in each case be substituted by one or more radicals $R^3$.

11. The compound according to claim 1, wherein L is a single bond or a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which is optionally substituted by in each case one or more radicals R, where one or more $CH_2$ groups, which are not adjacent.

12. A compound of the formula (1),

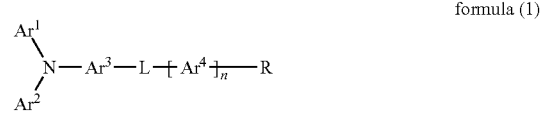   formula (1)

where the following applies to the symbols and indices used:

$Ar^1$ and $Ar^2$ are identically or differently on each occurrence, a group of the following formula (2),

   formula (2)

where the dashed bond indicates the bond to the nitrogen;

$Ar^3$ is selected from structures of the following formulae (18) to (116),

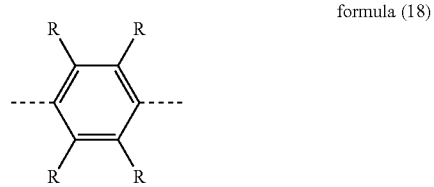   formula (18)

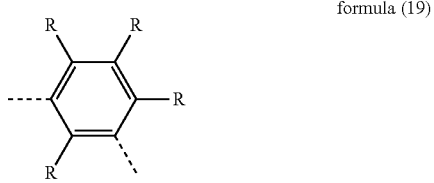   formula (19)

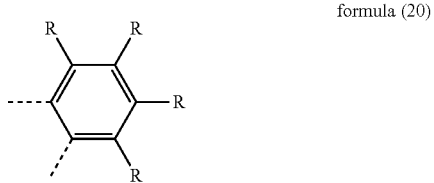   formula (20)

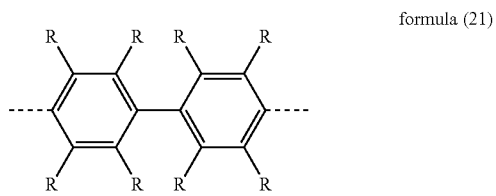   formula (21)

-continued
formula (22)
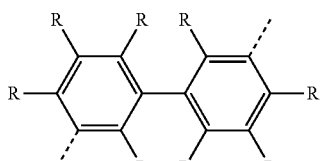
formula (23)
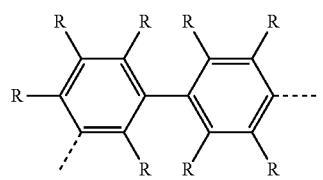
formula (24)
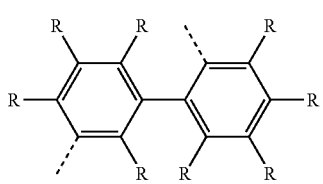
formula (25)
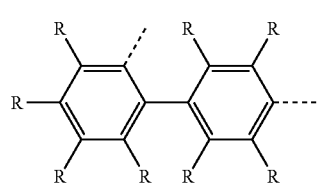
formula (26)
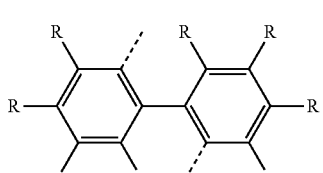
formula (27)
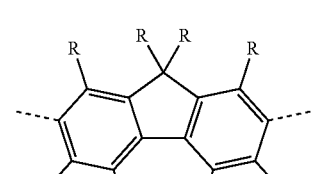
formula (28)
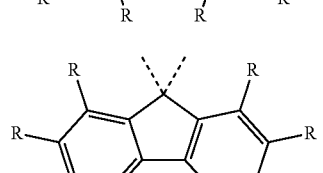
formula (29)
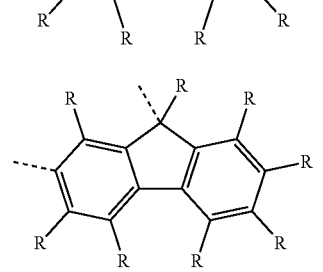
-continued
formula (30)
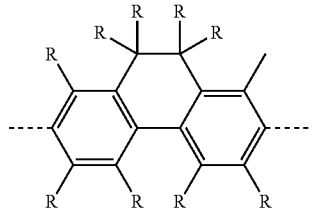
formula (31)
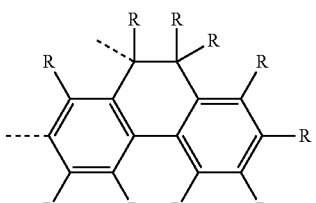
formula (32)
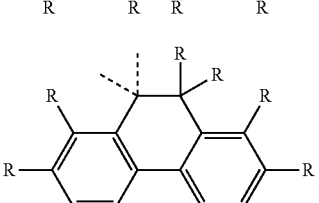
formula (33)
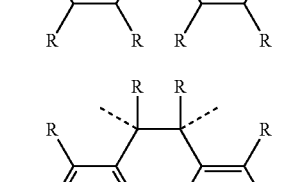
formula (34)
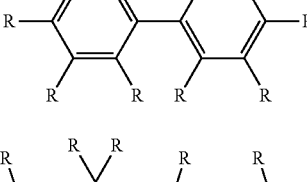
formula (35)
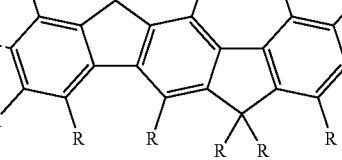
formula (36)
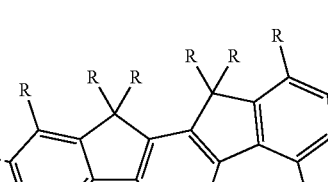
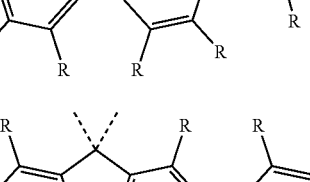

105
-continued
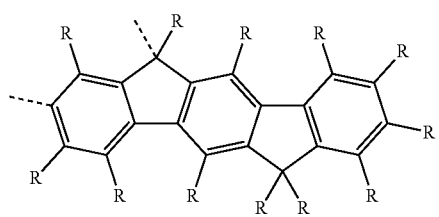
formula (37)
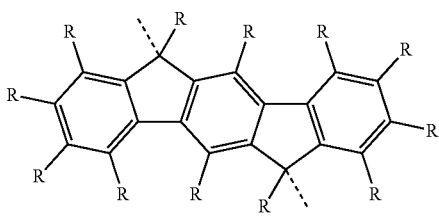
formula (38)
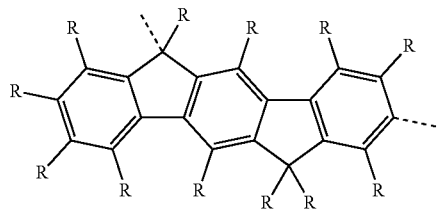
formula (39)
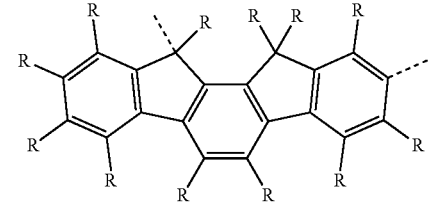
formula (40)
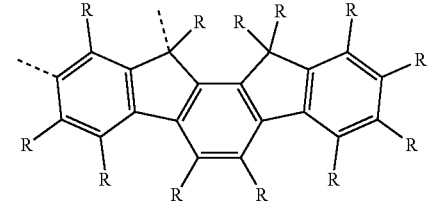
formula (41)
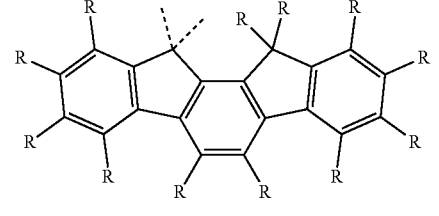
formula (42)
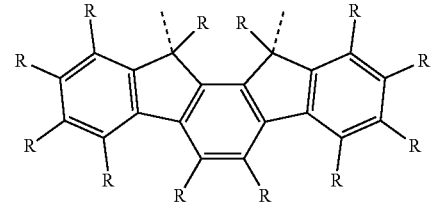
formula (43)
106
-continued
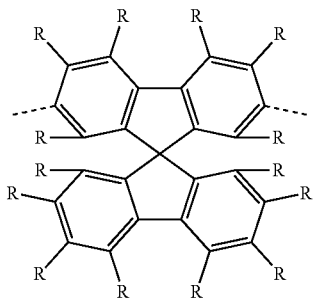
formula (44)
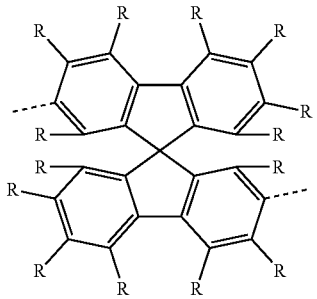
formula (45)
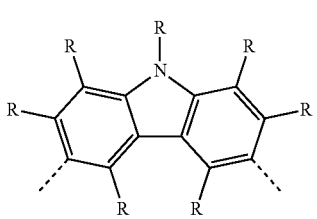
formula (46)
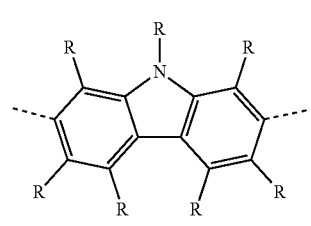
formula (47)
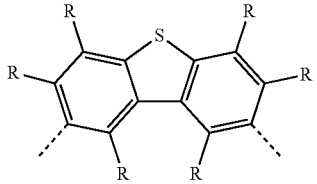
formula (48)
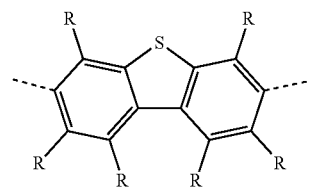
formula (49)
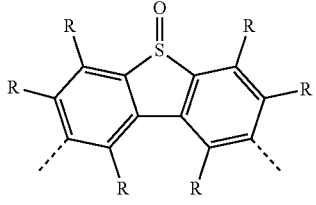
formula (50)

107
-continued
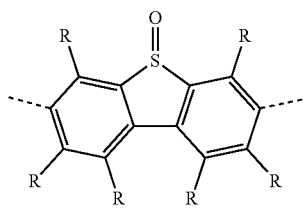
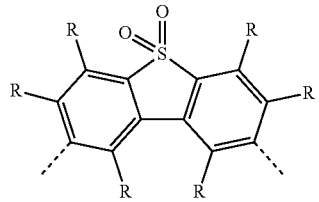
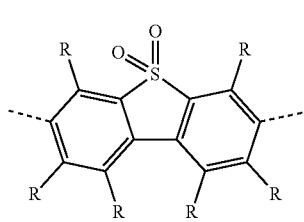
formula (54)
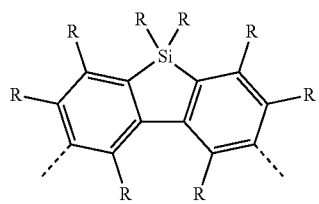
formula (55)
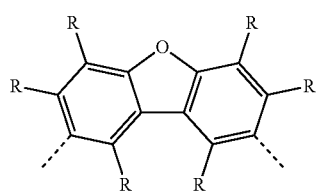
formula (56)
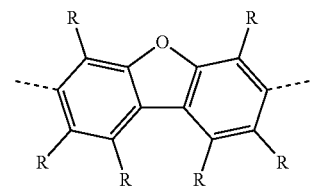
formula (57)
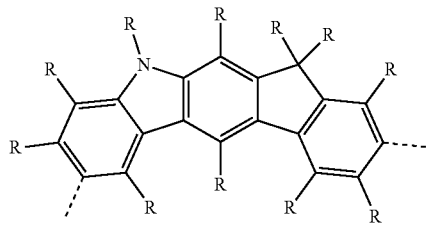
108
-continued
formula (58)
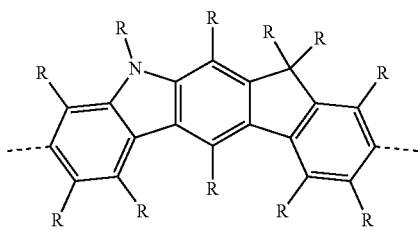
formula (59)
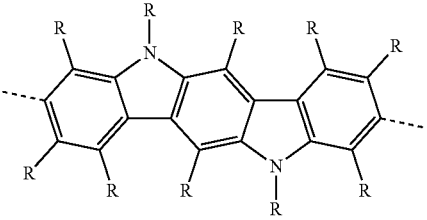
formula (60)
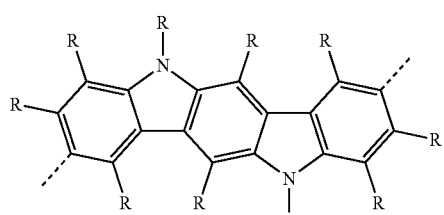
formula (61)
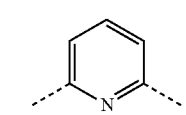
formula (62)
formula (63)
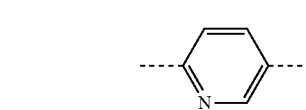
formula (64)
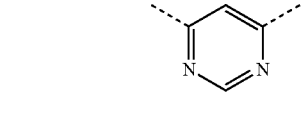
formula (65)
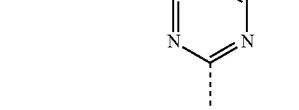
formula (66)
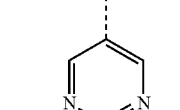
formula (67)

formula (68)
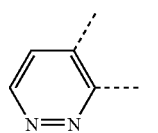
formula (69)
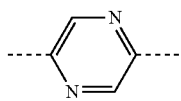
formula (70)
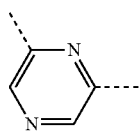
formula (71)
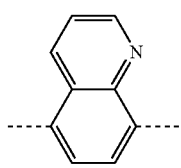
formula (72)
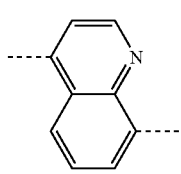
formula (73)
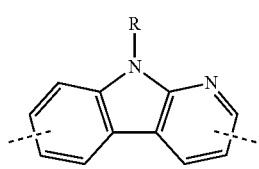
formula (74)
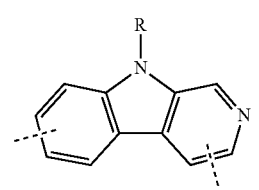
formula (75)
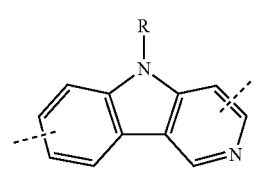
formula (76)
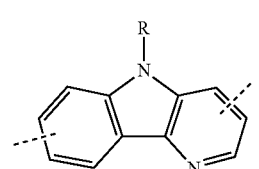
formula (77)
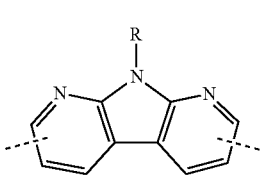
formula (78)
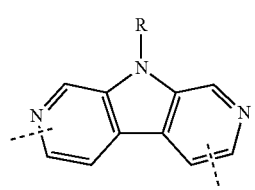
formula (79)
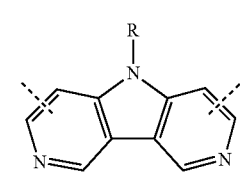
formula (80)
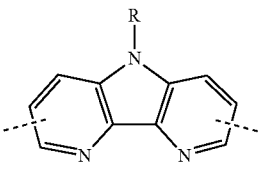
formula (81)
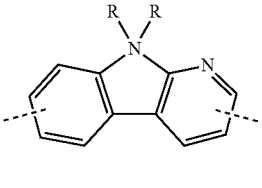
formula (82)
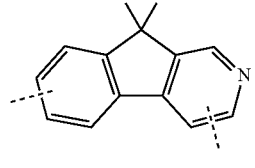
formula (83)
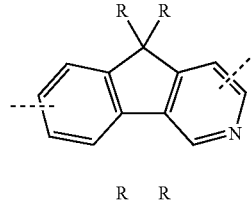
formula (84)
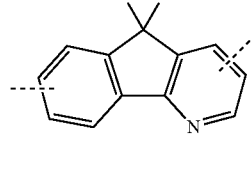
formula (85)
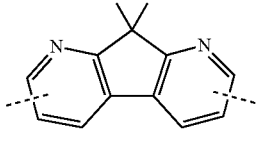
formula (86)
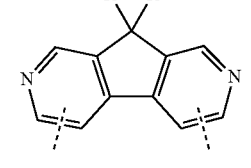

-continued
formula (87)
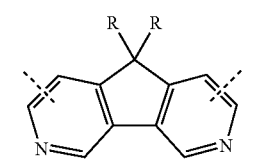
formula (88)
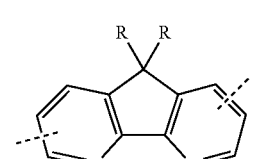
formula (89)
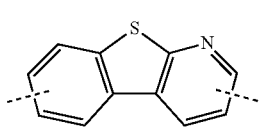
formula (90)
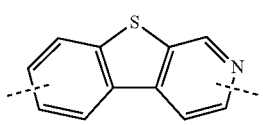
formula (91)
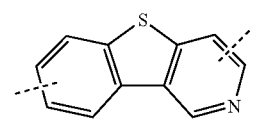
formula (92)
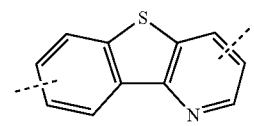
formula (93)
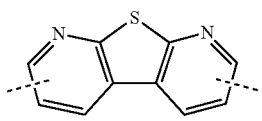
formula (94)
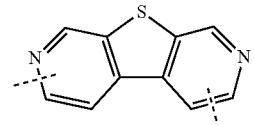
formula (95)
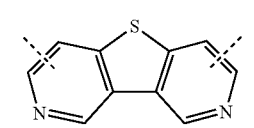
formula (96)
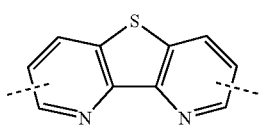
forumula (97)
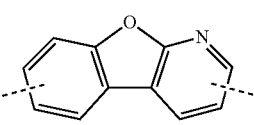
-continued
formula (98)
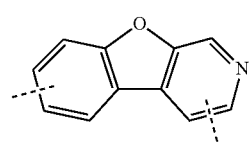
formula (99)
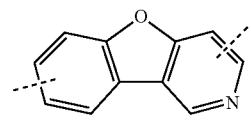
formula (100)
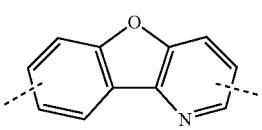
formula (101)
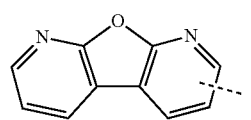
formula (102)
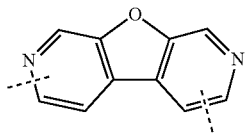
formula (103)
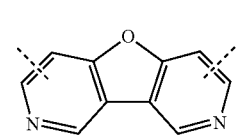
formula (104)
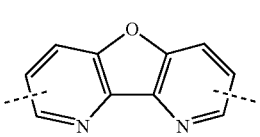
formula (105)
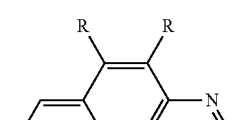
formula (106)
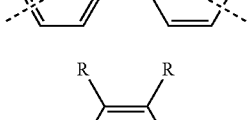
formula (107)
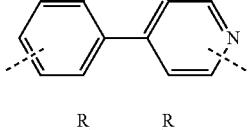
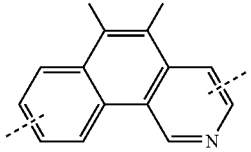

formula (108)

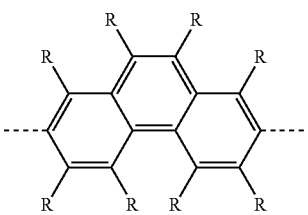

formula (109)

formula (110)

formula (111)

formula (112)

formula (113)

formula (114)

-continued

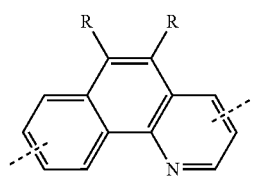

formula (115)

formula (116)

Ar⁴ is on each occurrence, identically or differently, an aromatic or heteroaromatic ring system having 5 to 30 aromatic ring atoms, which is optionally substituted by one or more radicals R; with the proviso that $Ar^3$ and $Ar^4$ contain no amino groups and no carbazole groups bonded via N;

X is on each occurrence, identically or differently, $CR^1$ or N, with the proviso that at least two groups X and a maximum of three groups X in each group of the formula (2) stand for N;

L is a single bond or a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which is optionally substituted by in each case one or more radicals R, where one or more $CH_2$ groups, is optionally replaced by $Si(R)_2$, $Ge(R)_2$, $Sn(R)_2$, C=O, C=S, C=Se, C=NR, P(=O)R, S=O, $SO_2$, —O—, —S— or —CONR— and where one or more H atoms is optionally replaced by D, F, Cl, Br, I, CN or $NO_2$, or a divalent aromatic or heteroaromatic ring system having 5 to 30 aromatic ring atoms, which is optionally substituted by one or more radicals R and which contains no amino groups and no carbazole groups bonded via N, or $Si(R)_2$, $Ge(R)_2$, O, S, C(=O), S(=O), $SO_2$, PR, P(=O)(R), P(=S)(R) or a combination of two, three, four or five of these systems;

R is selected on each occurrence, identically or differently, from the group consisting of H, D, F, Cl, Br, I, CN, $NO_2$, C(=O)Ar, C(=O)$R^2$, P(=O)(Ar)$_2$, B($R^2$)$_2$, B(O$R^2$)$_2$, Si($R^2$)$_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, C≡C, Si($R^2$)$_2$, Ge($R^2$)$_2$, Sn($R^2$)$_2$, C=O, C=S, C=Se, C=N$R^2$, P(=O)($R^2$), SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$ and which contains no amino groups and no carbazole groups bonded via N, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which may in each case be substituted by one or more radicals $R^2$, where two or more adjacent substituents R may optionally form a mono- or polycyclic, aliphatic, aromatic or heteroaromatic ring system, which is optionally substituted by one or more radicals $R^2$;

$R^1$ is selected on each occurrence, identically or differently, from the group consisting of D, F, Br, I, CN, $NO_2$, C(=O)Ar, C(=O)$R^2$, P(=O)(Ar)$_2$, B($R^2$)$_2$, B(O$R^2$)$_2$, Si($R^2$)$_3$, a straight-chain alkyl, or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, C≡C, Si($R^2$)$_2$, Ge($R^2$)$_2$, Sn($R^2$)$_2$, C=O, C=S, C=Se, C=N$R^2$, P(=O)($R^2$), SO, $SO_2$, N$R^2$, O, S or CON$R^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$ and which contains no amino groups and no carbazole groups bonded via N, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which may in each case be substituted by one or more radicals $R^2$, where two or more adjacent substituents R may optionally form a mono- or polycyclic, aliphatic, aromatic or heteroaromatic ring system, which is optionally substituted by one or more radicals $R^2$;

with the proviso that $R^1$ contains no condensed aryl groups;

$R^2$ is selected on each occurrence, identically or differently, from the group consisting of H, D, F, Cl, Br, I, CN, $NO_2$, C(=O)Ar, C(=O)$R^3$, P(=O)(Ar)$_2$, B($R^3$)$_2$, B(O$R^3$)$_2$, Si($R^3$)$_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, where one or more non-adjacent $CH_2$ groups is optionally replaced by $R^3C=CR^3$, C≡C, Si($R^3$)$_2$, Ge($R^3$)$_2$, Sn($R^3$)$_2$, C=O, C=S, C=Se, C=N$R^3$, P(=O)($R^3$), SO, $SO_2$, N$R^3$, O, S or CON$R^3$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^3$ and which contains no amino groups and no carbazole groups bonded via N, an aryloxy or heteroaryloxy group having 5 to 60 aromatic ring atoms, which is optionally substituted by one or more radicals $R^3$, or an aralkyl or heteroaralkyl group having 5 to 60 aromatic ring atoms, which is optionally substituted by one or more radicals $R^3$, where two or more adjacent substituents $R^2$ may optionally form a mono- or polycyclic, aliphatic, aromatic or heteroaromatic ring system, which is optionally substituted by one or more radicals $R^3$;

Ar is on each occurrence, identically or differently, an aromatic or heteroaromatic ring system having 5-30 aromatic ring atoms, which is optionally substituted by one or more non-aromatic radicals $R^3$; two radicals Ar which are bonded to the same P atom may also be bridged to one another here by a single bond or a bridge selected from N($R^3$), C($R^3$)$_2$, O or S;

$R^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^3$ may form a mono- or polycyclic, aliphatic, aromatic or heteroaromatic ring system with one another;

n is 0 or 1;

wherein at least one radical $R^1$ stands for an aromatic or heteroaromatic ring system and/or in that $Ar^3$ represents an aromatic or heteroaromatic ring system having at least two aryl or heteroaryl groups and/or in that n=1 and thus one group $Ar^4$ is present;

the following compounds are excluded from the invention:

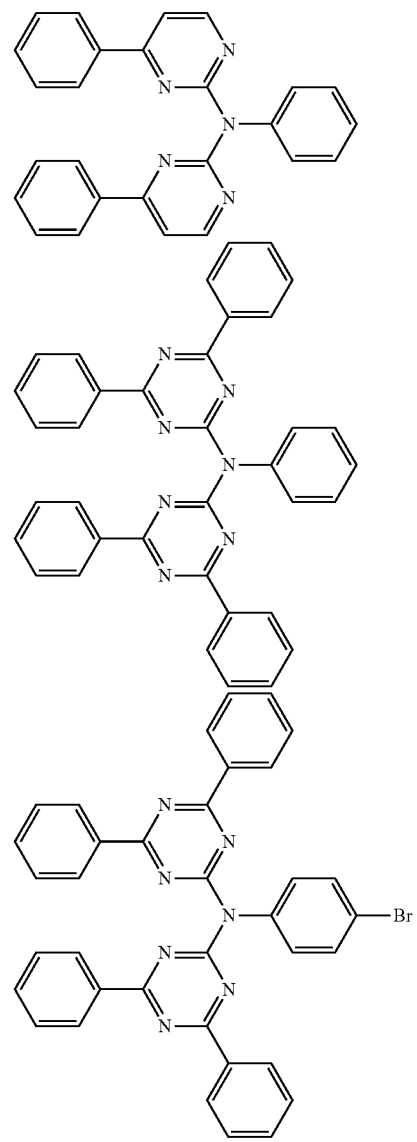

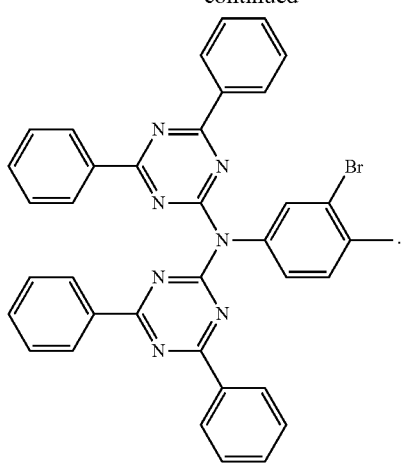

13. An electronic device which comprises a compound of the formula (1),

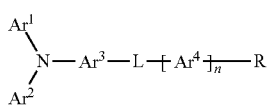

formula (1)

where the following applies to the symbols and indices used:

Ar¹ and Ar² are identically or differently on each occurrence, a group of the following formula (3)-formula (8) or formula (10)-formula (12)

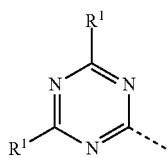

formula (3)

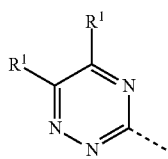

formula (4)

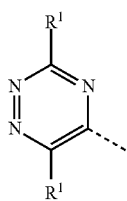

formula (5)

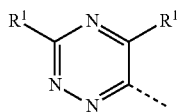

formula (6)

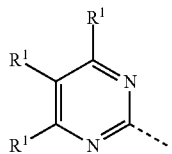

formula (7)

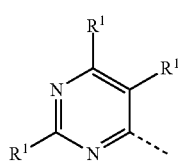

formula (8)

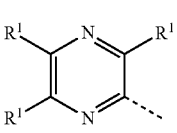

formula (10)

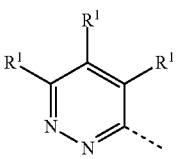

formula (11)

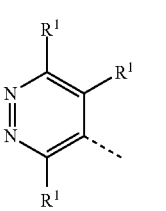

formula (12)

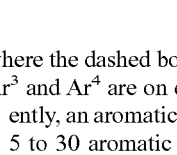

where the dashed bond indicates the bond to the nitrogen;

Ar³ and Ar⁴ are on each occurrence, identically or differently, an aromatic or heteroaromatic ring system having 5 to 30 aromatic ring atoms, which is optionally substituted by one or more radicals R; with the proviso that Ar³ and Ar⁴ contain no amino groups and no carbazole groups bonded via N;

L is a single bond or a divalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms, which is optionally substituted by in each case one or more radicals R, where one or more $CH_2$ groups, is optionally replaced by $Si(R)_2$, $Ge(R)_2$, $Sn(R)_2$, C=O, C=S, C=Se, C=NR, P(=O)R, S=O, $SO_2$, —O—, —S— or —CONR— and where one or more H atoms is optionally replaced by D, F, Cl, Br, I, CN or $NO_2$, or a divalent aromatic or heteroaromatic ring system having 5 to 30 aromatic ring atoms, which is optionally substituted by one or more radicals R and which contains no amino groups and no carbazole groups bonded via N, or $Si(R)_2$, $Ge(R)_2$, O, S, C(=O), S(=O), $SO_2$, PR, P(=O)(R), P(=S)(R) or a combination of two, three, four or five of these systems;

R is selected on each occurrence, identically or differently, from the group consisting of H, D, F, Cl, Br, I, CN, $NO_2$, C(=O)Ar, C(=O)$R^2$, P(=O)(Ar)$_2$, $B(R^2)_2$, $B(OR^2)_2$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40

C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$ and which contains no amino groups and no carbazole groups bonded via N, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which may in each case be substituted by one or more radicals $R^2$, where two or more adjacent substituents R may optionally form a mono- or polycyclic, aliphatic, aromatic or heteroaromatic ring system, which is optionally substituted by one or more radicals $R^2$;

$R^1$ is selected on each occurrence, identically or differently, from the group consisting of D, F, Cl, Br, I, CN, $NO_2$, C(=O)Ar, $C(=O)R^2$, $P(=O)(Ar)_2$, $B(R^2)_2$, $B(OR^2)_2$, $Si(R^2)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$, groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^2$ and which contains no amino groups and no carbazole groups bonded via N, an aryloxy or heteroaryloxy group having 5 to 60 aromatic ring atoms, which is optionally substituted by one or more radicals $R^2$, or an aralkyl or heteroaralkyl group having 5 to 60 aromatic ring atoms, which may in each case be substituted by one or more radicals $R^2$, where two or more adjacent substituents R may optionally form a mono- or polycyclic, aliphatic, aromatic or heteroaromatic ring system, which is optionally substituted by one or more radicals $R^2$;

with the proviso that $R^1$ contains no condensed aryl groups;

$R^2$ is selected on each occurrence, identically or differently, from the group consisting of H, D, F, Cl, Br, I, CN, $NO_2$, C(=O)Ar, $C(=O)R^3$, $P(=O)(Ar)_2$, $B(R^3)_2$, $B(OR^3)_2$, $Si(R^3)_3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^3$, where one or more non-adjacent $CH_2$ groups is optionally replaced by $R^3C=CR^3$, $C\equiv C$, $Si(R^3)_2$, $Ge(R^3)_2$, $Sn(R^3)_2$, $C=O$, $C=S$, $C=Se$, $C=NR^3$, $P(=O)(R^3)$, SO, $SO_2$, $NR^3$, O, S or $CONR^3$ and where one or more H atoms is optionally replaced by D, F, Cl, Br, I, CN or $NO_2$, an aromatic or heteroaromatic ring system having 5 to 60 aromatic ring atoms, which may in each case be substituted by one or more radicals $R^3$ and which contains no amino groups and no carbazole groups bonded via N, an aryloxy or heteroaryloxy group having 5 to 60 aromatic ring atoms, which is optionally substituted by one or more radicals $R^3$, or an aralkyl or heteroaralkyl group having 5 to 60 aromatic ring atoms, which is optionally substituted by one or more radicals $R^3$, where two or more adjacent substituents $R^2$ may optionally form a mono- or polycyclic, aliphatic, aromatic or heteroaromatic ring system, which is optionally substituted by one or more radicals $R^3$;

Ar is on each occurrence, identically or differently, an aromatic or heteroaromatic ring system having 5-30 aromatic ring atoms, which is optionally substituted by one or more non-aromatic radicals $R^3$; two radicals Ar which are bonded to the same P atom may also be bridged to one another here by a single bond or a bridge selected from $N(R^3)$, $C(R^3)_2$, O or S;

$R^3$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^3$ may form a mono- or polycyclic, aliphatic, aromatic or heteroaromatic ring system with one another;

n is 0 or 1;

wherein at least one radical $R^1$ stands for an aromatic or heteroaromatic ring system and/or in that $Ar^3$ represents an aromatic or heteroaromatic ring system having at least two aryl or heteroaryl groups and/or in that n=1 and thus one group $Ar^4$ is present;

the following compounds are excluded from the invention:

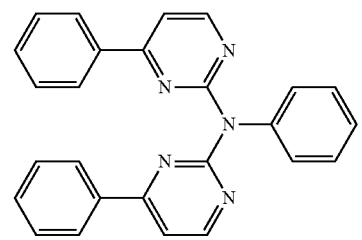

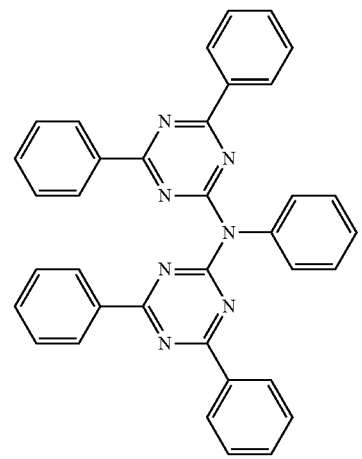

-continued

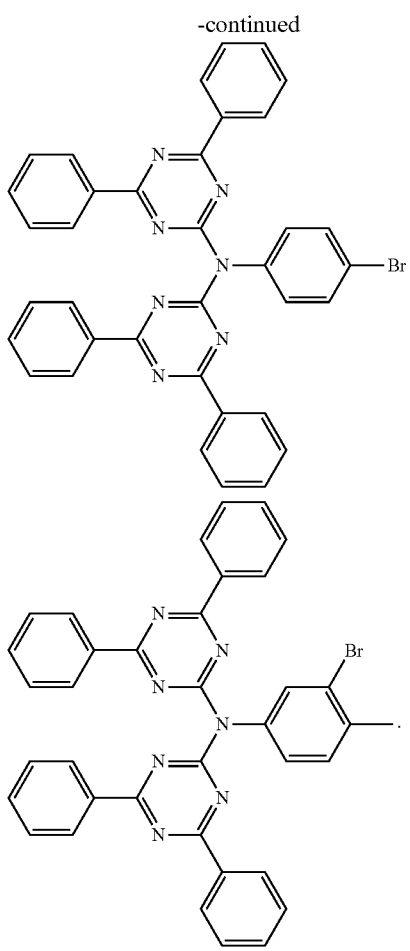

14. The device as claimed in claim 13, wherein the device is an organic electroluminescent device.

15. The electronic device as claimed in claim 13, wherein the device is an organic electroluminescent devices, an organic integrated circuit, an organic field-effect transistor, an organic thin-film transistor, an organic light-emitting transistor, an organic solar cell, a dye-sensitised organic solar cell, an organic optical detector, an organic photoreceptor, an organic field-quench device, a light-emitting electrochemical cell, an organic laser diode or an organic plasmon emitting device.

16. The electronic device as claimed in claim 13, wherein the device is an organic electroluminescent device and wherein the compound of the formula (1) is employed as matrix material for fluorescent or phosphorescent emitters and/or in a hole-blocking layer and/or in an electron-transport layer and/or in an electron-blocking or exciton-blocking layer and/or in a hole-transport layer.

17. An oligomer, polymer or dendrimer comprising one or more compounds according to claim 1, where one or more bonds are present from the compound according to claim 1 to the polymer, oligomer or dendrimer.

18. A formulation comprising at least one compound according to claim 1 and at least one solvent.

19. A mixture comprising at least one compound according to claim 1 and at least one further compound.

20. A process for the preparation of the compound according to claim 1, comprising the reaction steps:
   a) synthesis of a compound $G-L-Ar^3-NAr^1Ar^2$ by reaction of a compound $G-L-Ar^3-NH_2$ with a compound $G-Ar^1$ and $G-Ar^2$, optionally with addition of a base and/or a catalyst, where G stands for a reactive leaving group, in particular fluorine, chlorine, bromine or iodine; and
   b) introduction of the group $Ar^4$ or R by coupling a group $R-Ar^4-G$ or R-G to $Ar^3$ or L, for example by Suzuki coupling.

* * * * *

UNITED STATES PATENT AND TRADEMARK OFFICE
CERTIFICATE OF CORRECTION

PATENT NO. : 9,593,087 B2
APPLICATION NO. : 13/805943
DATED : March 14, 2017
INVENTOR(S) : Esther Breuning et al.

Page 1 of 2

It is certified that error appears in the above-identified patent and that said Letters Patent is hereby corrected as shown below:

In the Claims

In Claim 7, Column 94, formula 54, please delete the following formula:

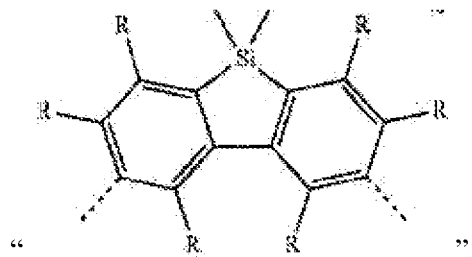

And replace the formula with the following formula:

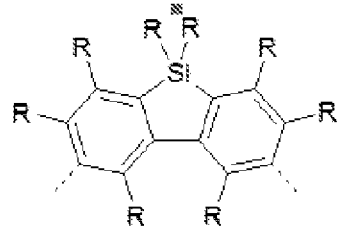

In Claim 7, Column 98, formula 98, please delete the following formula:

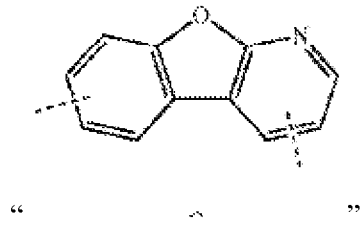

Signed and Sealed this
First Day of August, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,593,087 B2

And replace the formula with the following formula:

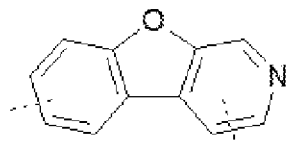

In Claim 12, Column 104, formula 30, please delete the following formula:

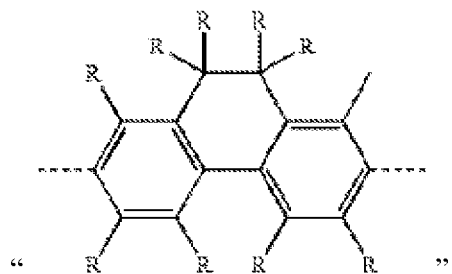

And replace the formula with the following formula: